(12) United States Patent
Brandt et al.

(10) Patent No.: US 7,960,374 B2
(45) Date of Patent: Jun. 14, 2011

(54) TRICYCLIC COMPOUNDS, COMPOSITIONS, AND METHODS USEFUL IN THE TREATMENT OR PROPHYLAXIS OF 5-$HT_6$ RECEPTOR-RELATED DISORDERS

(75) Inventors: Peter Brandt, Uppsala (SE); Erik Ringberg, Uppsala (SE); Berts Wei, Uppsala (SE); Rune Ringom, Uppsala (SE); Kristin Hammer, Sollentuna (SE); Sofia Henriksson, Solna (SE); Bengt Lindqvist, Uppsala (SE)

(73) Assignee: Proximagen Limited, London (GB)

( * ) Notice: Subject to any disclaimer, the term of this patent is extended or adjusted under 35 U.S.C. 154(b) by 587 days.

(21) Appl. No.: 11/980,114

(22) Filed: Oct. 30, 2007

(65) Prior Publication Data

US 2008/0176829 A1    Jul. 24, 2008

Related U.S. Application Data

(60) Provisional application No. 60/872,209, filed on Dec. 1, 2006.

(30) Foreign Application Priority Data

Oct. 30, 2006 (SE) .................... 0602283-4

(51) Int. Cl.
*A61K 31/55* (2006.01)
*C07D 491/00* (2006.01)
*C07D 487/00* (2006.01)

(52) U.S. Cl. ......... 514/215; 514/220; 540/557; 540/580
(58) Field of Classification Search .................. None
See application file for complete search history.

(56) References Cited

U.S. PATENT DOCUMENTS 7,056,942 B2 * 6/2006 Hildesheim et al. .......... 514/411

FOREIGN PATENT DOCUMENTS

| WO | WO-01/32646 | 5/2001 |
|---|---|---|
| WO | WO-01/32660 | 5/2001 |
| WO | WO-2005/037834 | 4/2005 |
| WO | WO-2005/047252 | 5/2005 |

OTHER PUBLICATIONS

Jantzen and Robinson, Modern Pharmaceutics, p. 596.*
Guo et al. Journal of Nuclear Medicine, 2009, 50(10), pp. 1715-1723.*
Zhou et al., "4-(2-Aminoethoxy)-N-(phenylsulfonyl)indoles as novel 5-$HT_6$ receptor ligands", Bioorganic & Medicinal Chem. Letters, vol. 15, No. 5, 2005, pp. 1393-1396.
Cole et al., "$N_1$-arylsulfonyl-3-(1,2,3,6-tetrahydropyridin-4-yl)-1H-indole derivatives are potent and selective 5-$HT_6$ receptor antagonists", Bioorganic & Medicinal Chem. Letters, vol. 15, 2005, pp. 379-383.

* cited by examiner

*Primary Examiner* — Noble Jarrell
(74) *Attorney, Agent, or Firm* — Edwards Angell Palmer & Dodge LLP; Jeffrey D. Hsi; Weiying Yang

(57) ABSTRACT

The present invention relates to compounds of the formula (I)

(I)

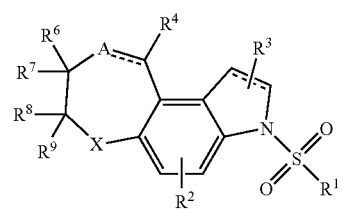

wherein A, X and $R^1$ to $R^9$ are as described herein; to pharmaceutical compositions comprising the said compounds; to processes for their preparation; and to the use of the compounds as medicaments against 5-$HT_6$ receptor-related disorders.

14 Claims, No Drawings

TRICYCLIC COMPOUNDS, COMPOSITIONS, AND METHODS USEFUL IN THE TREATMENT OR PROPHYLAXIS OF 5-HT$_6$ RECEPTOR-RELATED DISORDERS

CROSS-REFERENCE TO RELATED APPLICATIONS

This application claims benefit of Swedish application No. 0602283-4 filed Oct. 30, 2006 and U.S. application 60/872,209 filed Dec. 1, 2006; the entire contents of each of these applications is herein incorporated by reference.

TECHNICAL FIELD

The present invention relates to novel compounds, to pharmaceutical compositions comprising the compounds, to processes for their preparation, as well as to the use of the compounds for the preparation of a medicament against 5-HT$_6$ receptor-related disorders.

BACKGROUND OF THE INVENTION

Obesity is a condition characterized by an increase in body fat content resulting in excess body weight above accepted norms. Obesity is the most important nutritional disorder in the western world and represents a major health problem in all industrialized countries. This disorder leads to increased mortality due to increased incidences of diseases such as cardiovascular disease, digestive disease, respiratory disease, cancer and type 2 diabetes. Searching for compounds that reduce body weight has been going on for many decades. One line of research has been activation of serotoninergic systems, either by direct activation of serotonin receptor subtypes or by inhibiting serotonin reuptake. The exact receptor subtype profile required is however not known.

Serotonin (5-hydroxytryptamine or 5-HT), a key transmitter of the peripheral and central nervous system, modulates a wide range of physiological and pathological functions, including anxiety, sleep regulation, aggression, feeding and depression. Multiple serotonin receptor subtypes have been identified and cloned. One of these, the 5-HT$_6$ receptor, was cloned by several groups in 1993 (Ruat, M. et al. (1993) Biochem. Biophys. Res. Commun. 193: 268-276; Sebben, M. et al. (1994) NeuroReport 5: 2553-2557). This receptor is positively coupled to adenylyl cyclase and displays affinity for antidepressants such as clozapine. Recently, the effect of 5-HT$_6$ antagonist and 5-HT$_6$ antisense oligonucleotides to reduce food intake in rats has been reported (Bentley, J. C. et al. (1999) Br J Pharmacol. Suppl. 126, P66; Bentley, J. C. et al. (1997) J. Psychopharmacol. Suppl. A64, 255; Woolley M. L. et al. (2001) Neuropharmacology 41: 210-219).

Compounds with enhanced affinity and selectivity for the 5-HT$_6$ receptor have been identified, e.g. in WO 00/34242 and by Isaac, M. et al. (2000) *6-Bicyclopiperazinyl-1-arylsulphonylindoles and 6-Bicyclopiperidinyl-1-arylsulphonylindoles derivatives as novel, potent and selective 5-HT$_6$ receptor antagonists*. Bioorganic & Medicinal Chemistry Letters 10: 1719-1721 (2000), Bioorganic & Medicinal Chemistry Letters 13: 3355-3359 (2003), Expert Opinion Therapeutic Patents 12(4) 513-527 (2002).

DISCLOSURE OF THE INVENTION

It has surprisingly been found that the compounds according to the present invention show affinity for the 5-HT$_6$ receptor at nanomolar range. Compounds according to the present invention and their pharmaceutically acceptable salts have 5-HT$_6$ receptor antagonist, agonist and partial agonist activity, preferably antagonist activity, and are believed to be of potential use in the treatment or prophylaxis of obesity and type 2 diabetes, to achieve reduction of body weight and of body weight gain, as well as in the treatment or prophylaxis of disorders of the central nervous system such as anxiety, depression, panic attacks, memory disorders, cognitive disorders, epilepsy, sleep disorders, migraine, anorexia, bulimia, binge eating disorders, obsessive compulsive disorders, psychoses, Alzheimer's disease, Parkinson's disease, Huntington's chorea and/or schizophrenia, panic attacks, Attention Deficit Hyperactive Disorder (ADHD), withdrawal from drug abuse (e.g. abuse of amphetamine, cocain abuse and/or nicotine), neurodegenerative diseases characterized by impaired neuronal growth, and pain. The reduction of body weight and of body weight gain (e.g. treating body-weight disorders) is achieved inter alia by reduction of food intake. As used herein, the term "body weight disorders" refers to the disorders caused by an imbalance between energy intake and energy expenditure, resulting in abnormal (e.g., excessive) body weight. Such body weight disorders include but are not limited to, obesity, overweight, anorexia, cachexia, insulin resistance, and diabetes.

One object of the present invention is a compound of the formula (I)

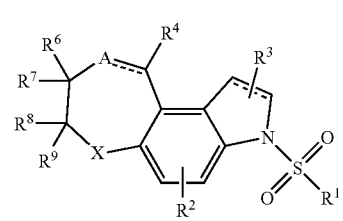

(I)

wherein:
⁓ represents a single bond or a double bond;
A is N or NR$^5$;
X is O, S, N—H or N—C$_{1-6}$-alkyl;
R$^1$ is a group selected from:
  (a) C$_{1-6}$-alkyl,
  (b) C$_{3-7}$-cycloalkyl,
  (c) C$_{3-6}$-alkenyl,
  (d) aryl,
  (e) aryl-C$_{2-6}$-alkenyl,
  (f) aryl-C$_{1-6}$-alkyl,
  (g) heteroaryl,
  (h) heteroaryl-C$_{2-6}$-alkenyl, and
  (i) heteroaryl-C$_{1-6}$-alkyl,
wherein any heteroaryl or aryl residue, alone or as part of another group, is optionally independently substituted in one or more positions with a substituent selected from:
  (a) halogen,
  (b) C$_{1-6}$-alkyl,
  (c) fluoro-C$_{1-6}$-alkyl,
  (d) C$_{3-7}$-cycloalkyl,
  (e) methyl-C$_{3-7}$-cycloalkyl,
  (f) fluoro-C$_{3-7}$-cycloalkyl,
  (g) C$_{2-6}$-alkenyl,
  (h) fluoro-C$_{2-6}$-alkenyl,
  (i) ethynyl;
  (j) hydroxy-C$_{1-4}$-alkyl,
  (k) hydroxy,
  (l) C$_{1-6}$-alkoxy (m) fluoro-$C_{1-6}$-alkoxy
(n) $C_{3-7}$-cycloalkoxy
(o) methyl-$C_{3-7}$-cycloalkoxy
(p) fluoro-$C_{3-7}$-cycloalkoxy
(q) —$SCF_3$,
(r) —$SCF_2H$,
(s) —$SO_2NR^{10}R^{10}$,
(t) —$S(O)_eR^{11}$, wherein e is 0, 1, 2 or 3,
(u) —CN,
(v) —$NR^{10}R^{10}$,
(w) —$NHSO_2R^{11}$,
(x) —$NR^{12}COR^{11}$,
(y) —$NO_2$,
(z) —$CONR^{10}R^{10}$,
(aa) —CO—$R^{11}$,
(bb) —COOH,
(cc) $C_{1-6}$-alkoxycarbonyl,
(dd) aryl,
(ee) heteroaryl,
(ff) aryloxy, and
(gg) heteroaryloxy,
wherein any (dd) aryl or (ee) heteroaryl, alone or as part of another group, is optionally substituted in one or more positions with a substituent selected from:
(a) halogen,
(b) $C_{1-4}$-alkyl,
(c) $C_{1-4}$-alkylthio,
(d) $C_{1-4}$-alkoxy,
(e) —$CF_3$,
(f) —CN, and
(g) hydroxymethyl;
$R^2$ is a group selected from:
(a) hydrogen
(b) halogen,
(c) $C_{1-6}$-alkyl,
(d) fluoro-$C_{1-6}$-alkyl,
(e) $C_{3-7}$-cycloalkyl,
(f) methyl-$C_{3-7}$-cycloalkyl,
(g) fluoro-$C_{3-7}$-cycloalkyl,
(h) $C_{2-6}$-alkenyl,
(i) fluoro-$C_{2-6}$-alkenyl,
(j) ethynyl,
(k) hydroxy-$C_{1-4}$-alkyl,
(l) hydroxy,
(m) $C_{1-6}$-alkoxy,
(n) fluoro-$C_{1-6}$-alkoxy,
(o) $C_{3-7}$-cycloalkoxy,
(p) methyl-$C_{3-7}$-cycloalkoxy,
(q) fluoro-$C_{3-7}$-cycloalkoxy,
(r) —$SCF_3$,
(s) —$SCF_2H$,
(t) —$SO_2NR^{10}R^{10}$,
(u) —$S(O)_eR^{11}$, wherein e is 0, 1, 2 or 3,
(v) —CN,
(w) —$NR^{10}R^{10}$,
(x) —$NR^{12}SO_2R^{11}$,
(y) —$NR^{12}COR^{11}$,
(z) —$NO_2$,
(aa) —$CONR^{10}R^{10}$,
(bb) —$OCONR^{10}R^{10}$,
(cc) —CO—$R^{11}$,
(dd) —COOH, and
(ee) $C_{1-6}$-alkoxycarbonyl;
$R^3$ is a group selected from:
(a) hydrogen,
(b) halogen,
(c) $C_{1-6}$-alkyl,
(d) $C_{3-7}$-cycloalkyl,
(e) hydroxy-$C_{1-4}$-alkyl,
(f) $C_{3-7}$-cycloalkyl-hydroxy-$C_{1-4}$-alkyl
(g) $C_{1-2}$-alkoxy-$C_{1-4}$-alkyl
(h) —$COOR^{12}$,
(i) —$CONR^{10}R^{10}$,
(j) —CO—$R^{11}$,
(k) —CN,
(l) aryl, and
(m) heteroaryl,
wherein any heteroaryl or aryl residue is optionally independently substituted in one or more positions with a substituent selected from:
(a) halogen,
(b) $C_{1-4}$-alkyl,
(c) $C_{1-4}$-alkylthio,
(d) $C_{1-4}$-alkoxy,
(e) —$CF_3$,
(f) —CN, and
(g) hydroxymethyl;
$R^4$ is a group selected from:
(a) hydrogen,
(b) $C_{1-4}$-alkyl,
(c) fluoro-$C_{1-4}$-alkyl,
(d) $C_{3-5}$-cycloalkyl,
(e) fluoro-$C_{3-5}$-cycloalkyl,
(f) hydroxy-$C_{1-4}$-alkyl, and
(g) cyano;
$R^5$ is a group selected from:
(a) hydrogen,
(b) $C_{1-4}$-alkyl,
(c) fluoro-$C_{1-4}$-alkyl,
(d) 2-cyanoethyl,
(e) hydroxy-$C_{2-4}$-alkyl,
(f) $C_{3-4}$-alkenyl,
(g) $C_{3-4}$-alkynyl,
(h) $C_{3-7}$-cycloalkyl,
(i) methyl-$C_{3-7}$-cycloalkyl
(j) fluoro-$C_{3-7}$-cycloalkyl,
(k) $C_{3-4}$-cycloalkyl-$C_{1-4}$-alkyl, and
(l) $C_{1-4}$-alkoxy-$C_{2-4}$-alkyl, or
$R^5$ and one of $R^6$, $R^7$, $R^8$, or $R^9$ groups together with the atoms to which they are attached form a heterocyclic ring and the other three of $R^6$, $R^7$, $R^8$ or $R^9$ are hydrogen;
$R^6$, $R^7$, $R^8$, and $R^9$ are each independently selected from:
(a) hydrogen,
(b) $C_{1-6}$-alkyl,
(c) fluoro-$C_{1-6}$-alkyl,
(d) $C_{3-7}$-cycloalkyl, and
(e) hydroxy-$C_{1-4}$-alkyl,
with the proviso that three of $R^6$, $R^7$, $R^8$ and $R^9$ are hydrogen unless at least two of $R^6$, $R^7$, $R^8$ and $R^9$ are methyl and the remainder of them are hydrogen,
two of the $R^6$, $R^7$, $R^8$, or $R^9$ groups together with the atoms to which they are attached form a carbocyclic or heterocyclic ring and the other two of $R^6$, $R^7$, $R^8$ or $R^9$ are hydrogen, or
one of $R^6$, $R^7$, $R^8$, or $R^9$ groups and $R^5$ together with the atoms to which they are attached form a heterocyclic ring and the other three of $R^6$, $R^7$, $R^8$ or $R^9$ are hydrogen;
$R^{10}$ is each independently a group selected from:
(a) hydrogen,
(b) $C_{1-6}$-alkyl,
(c) fluoro-$C_{2-6}$-alkyl, and
(d) $C_{3-7}$-cycloalkyl, or two $R^{10}$ groups together with the nitrogen to which they are attached form a heterocyclic ring optionally substituted with methyl;

$R^{11}$ is each independently a group selected from:
(a) hydrogen,
(b) $C_{1-6}$-alkyl,
(c) fluoro-$C_{1-6}$-alkyl,
(d) $C_{3-7}$-cycloalkyl,
(e) methyl-$C_{3-7}$-cycloalkyl,
(f) aryl, and
(g) heteroaryl,
wherein any heteroaryl or aryl residue is optionally independently substituted in one or more positions with a substituent selected from:
(a) halogen,
(b) $C_{1-4}$-alkyl,
(c) $C_{1-4}$-alkylthio,
(d) $C_{1-4}$-alkoxy,
(e) —$CF_3$,
(f) —CN, and
(g) hydroxymethyl, $R^{12}$ is each independently a group selected from:
(a) hydrogen,
(b) $C_{1-6}$-alkyl,
(c) fluoro-$C_{1-6}$-alkyl,
(d) $C_{3-7}$-cycloalkyl, and
(e) hydroxy-$C_{1-4}$-alkyl,
or $R^{11}$ and $R^{12}$ together with the atoms to which they are attached form a lactam ring when present in the group $NR^{12}COR^{11}$, or $R^{11}$ and $R^{12}$ together with the atoms to which they are attached form a sultam ring when present in the group $NR^{12}SO_2R^{11}$, and pharmaceutically acceptable salts, hydrates, solvates, geometrical isomers, tautomers, optical isomers, and prodrug forms thereof.

A preferred group are compounds of formula (II)

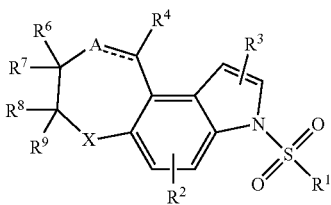

(II)

wherein:
⸺ represents a single bond or a double bond;
A, X, $R^1$, $R^2$, $R^3$, $R^4$, $R^5$, $R^6$, $R^7$, $R^8$, $R^9$, $R^{10}$, $R^{11}$ and $R^{12}$ are as defined for formula (I).

Another preferred group are compounds of formula (III)

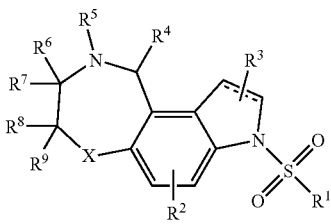

(III)

wherein:
⸺ represents a single bond or a double bond;
X is O, S, N—H, or N—$C_{1-6}$-alkyl;

$R^1$ is a group selected from:
(a) $C_{1-6}$-alkyl,
(b) $C_{3-7}$-cycloalkyl,
(c) $C_{3-6}$-alkenyl,
(d) aryl,
(e) aryl-$C_{2-6}$-alkenyl,
(f) aryl-$C_{1-6}$-alkyl,
(g) heteroaryl,
(h) heteroaryl-$C_{2-6}$-alkenyl, and
(i) heteroaryl-$C_{1-6}$-alkyl,
wherein any heteroaryl or aryl residue, alone or as part of another group, is optionally independently substituted in one or more positions with a substituent selected from:
(a) halogen,
(b) $C_{1-6}$-alkyl,
(c) fluoro-$C_{1-6}$-alkyl,
(d) $C_{3-7}$-cycloalkyl,
(e) methyl-$C_{3-7}$-cycloalkyl,
(f) fluoro-$C_{3-7}$-cycloalkyl,
(g) $C_{2-6}$-alkenyl,
(h) fluoro-$C_{2-6}$-alkenyl,
(i) ethynyl;
(j) hydroxy-$C_{1-4}$-alkyl,
(k) hydroxy,
(l) $C_{1-6}$-alkoxy
(m) fluoro-$C_{1-6}$-alkoxy
(n) $C_{3-7}$-cycloalkoxy
(o) methyl-$C_{3-7}$-cycloalkoxy
(p) fluoro-$C_{3-7}$-cycloalkoxy
(q) —$SCF_3$,
(r) —$SCF_2H$,
(s) —$SO_2NR^{10}R^{10}$,
(t) —$S(O)_eR^{11}$, wherein e is 0, 1, 2 or 3,
(u) —CN,
(v) —$NR^{10}R^{10}$,
(w) —$NHSO_2R^{11}$,
(x) —$NR^{12}COR^{11}$,
(y) —$NO_2$,
(z) —$CONR^{10}R^{10}$,
(aa) —CO—$R^{11}$,
(bb) —COOH,
(cc) $C_{1-6}$-alkoxycarbonyl,
(dd) aryl,
(ee) heteroaryl,
(ff) aryloxy, and
(gg) heteroaryloxy;
wherein any (dd) aryl or (ee) heteroaryl, alone or as part of another group, is optionally substituted in one or more positions with a substituent selected from:
(a) halogen,
(b) $C_{1-4}$-alkyl,
(c) $C_{1-4}$-alkylthio,
(d) $C_{1-4}$-alkoxy,
(e) —$CF_3$,
(f) —CN, and
(g) hydroxymethyl;

$R^2$ is a group selected from:
(a) hydrogen
(b) halogen,
(c) $C_{1-6}$-alkyl,
(d) fluoro-$C_{1-6}$-alkyl,
(e) $C_{3-7}$-cycloalkyl,
(f) methyl-$C_{3-7}$-cycloalkyl,
(g) fluoro-$C_{3-7}$-cycloalkyl,
(h) $C_{2-6}$-alkenyl,
(i) fluoro-$C_{2-6}$-alkenyl,
(j) ethynyl, (k) hydroxy-$C_{1-4}$-alkyl,
(l) hydroxy,
(m) $C_{1-6}$-alkoxy,
(n) fluoro-$C_{1-6}$-alkoxy,
(o) $C_{3-7}$-cycloalkoxy,
(p) methyl-$C_{3-7}$-cycloalkoxy,
(q) fluoro-$C_{3-7}$-cycloalkoxy,
(r) —$SCF_3$,
(s) —$SCF_2H$,
(t) —$SO_2NR^{10}R^{10}$,
(u) —$S(O)_eR^{11}$, wherein e is 0, 1, 2 or 3,
(v) —CN,
(w) —$NR^{10}R^{10}$,
(x) —$NR^{12}SO_2R^{11}$,
(y) —$NR^{12}COR^{11}$,
(z) —$NO_2$,
(aa) —$CONR^{10}R^{10}$,
(bb) —$OCONR^{10}R^{10}$,
(cc) —CO—$R^{11}$,
(dd) —COOH, and
(ee) $C_{1-6}$-alkoxycarbonyl;
$R^3$ is a group selected from:
  (a) hydrogen,
  (b) $C_{1-6}$-alkyl,
  (c) $C_{3-7}$-cycloalkyl,
  (d) hydroxy-$C_{1-4}$-alkyl,
  (e) $C_{1-2}$-alkoxy-$C_{1-4}$-alkyl
  (f) —$COOR^{12}$,
  (g) —$CONR^{10}R^{10}$,
  (h) —CO—$R^{11}$,
  (i) —CN,
  (j) aryl, and
  (k) heteroaryl,
wherein any heteroaryl or aryl residue is optionally independently substituted in one or more positions with a substituent selected from:
  (a) halogen,
  (b) $C_{1-4}$-alkyl,
  (c) $C_{1-4}$-alkylthio,
  (d) $C_{1-4}$-alkoxy,
  (e) —$CF_3$,
  (f) —CN, and
  (g) hydroxymethyl;
$R^4$ is a group selected from:
  (a) hydrogen,
  (b) $C_{1-4}$-alkyl,
  (c) fluoro-$C_{1-4}$-alkyl,
  (d) $C_{3-5}$-cycloalkyl,
  (e) fluoro-$C_{3-5}$-cycloalkyl,
  (f) hydroxy-$C_{1-4}$-alkyl, and
  (g) cyano;
$R^5$ is a group selected from:
  (a) hydrogen,
  (b) $C_{1-4}$-alkyl,
  (c) fluoro-$C_{1-4}$-alkyl,
  (d) 2-cyanoethyl,
  (e) hydroxy-$C_{2-4}$-alkyl,
  (f) $C_{3-4}$-alkenyl,
  (g) $C_{3-4}$-alkynyl,
  (h) $C_{3-7}$-cycloalkyl,
  (i) methyl-$C_{3-7}$-cycloalkyl
  (j) fluoro-$C_{3-7}$-cycloalkyl,
  (k) $C_{3-4}$-cycloalkyl-$C_{1-4}$-alkyl, and
  (l) $C_{1-4}$-alkoxy-$C_{2-4}$-alkyl, or $R^5$ and one of $R^6$, $R^7$, $R^8$, or $R^9$ groups together with the atoms to which they are attached form a heterocyclic ring and the other three of $R^6$, $R^7$, $R^8$ or $R^9$ are hydrogen;
$R^6$, $R^7$, $R^8$, and $R^9$ are each independently selected from:
  (a) hydrogen,
  (b) $C_{1-6}$-alkyl,
  (c) fluoro-$C_{1-6}$-alkyl,
  (d) $C_{3-7}$-cycloalkyl, and
  (e) hydroxy-$C_{1-4}$-alkyl,
  with the proviso that three of $R^6$, $R^7$, $R^8$ and $R^9$ are hydrogen unless at least two of $R^6$, $R^7$, $R^8$ and $R^9$ are methyl and the remainder of them are hydrogen,
  two of the $R^6$, $R^7$, $R^8$, or $R^9$ groups together with the atoms to which they are attached form a carbocyclic or heterocyclic ring and the other two of $R^6$, $R^7$, $R^8$ or $R^9$ are hydrogen, or
  one of $R^6$, $R^7$, $R^8$, or $R^9$ groups and $R^5$ together with the atoms to which they are attached form a heterocyclic ring and the other three of $R^6$, $R^7$, $R^8$ or $R^9$ are hydrogen;
$R^{10}$ is each independently a group selected from:
  (a) hydrogen,
  (b) $C_{1-6}$-alkyl,
  (c) fluoro-$C_{2-6}$-alkyl, and
  (d) $C_{3-7}$-cycloalkyl, or
  two $R^{10}$ groups together with the nitrogen to which they are attached form a heterocyclic ring optionally substituted with methyl;
$R^{11}$ is each independently a group selected from:
  (a) hydrogen,
  (b) $C_{1-6}$-alkyl,
  (c) fluoro-$C_{1-6}$-alkyl,
  (d) $C_{3-7}$-cycloalkyl,
  (e) methyl-$C_{3-7}$-cycloalkyl,
  (f) aryl, and
  (g) heteroaryl,
wherein any heteroaryl or aryl residue is optionally independently substituted in one or more positions with a substituent selected from:
  (a) halogen,
  (b) $C_{1-4}$-alkyl,
  (c) $C_{1-4}$-alkylthio,
  (d) $C_{1-4}$-alkoxy,
  (e) —$CF_3$,
  (f) —CN, and
  (g) hydroxymethyl,
$R^{12}$ is each independently a group selected from:
  (a) hydrogen,
  (b) $C_{1-6}$-alkyl,
  (c) fluoro-$C_{1-6}$-alkyl,
  (d) $C_{3-7}$-cycloalkyl, and
  (e) hydroxy-$C_{1-4}$-alkyl,
or $R^{11}$ and $R^{12}$ together with the atoms to which they are attached form a lactam ring when present in the group $NR^{12}COR^{11}$, or $R^{11}$ and $R^{12}$ together with the atoms to which they are attached form a sultam ring when present in the group $NR^{12}SO_2R^{11}$.

It is preferred in formula (II) that:
⸺ represents a single bond or a double bond;
X=O;
$R^1$ is a group selected from:
  (a) aryl,
  (b) heteroaryl,
wherein any heteroaryl or aryl residue, is optionally independently substituted in one or more positions with a substituent selected from:

(a) halogen,
(b) $C_{1-6}$-alkyl,
(c) fluoro-$C_{1-6}$-alkyl,
(d) $C_{3-7}$-cycloalkyl,
(e) fluoro-$C_{3-7}$-cycloalkyl,
(f) $C_{2-6}$-alkenyl,
(g) fluoro-$C_{2-6}$-alkenyl,
(h) ethynyl;
(i) hydroxy-$C_{1-4}$-alkyl,
(j) hydroxy,
(k) $C_{1-6}$-alkoxy
(l) fluoro-$C_{1-6}$-alkoxy
(m) $C_{3-7}$-cycloalkoxy
(n) fluoro-$C_{3-7}$-cycloalkoxy
(o) —$SCF_3$,
(p) —$SCF_2H$,
(q) —$SO_2NR^{10}R^{10}$,
(r) —$S(O)_eR^{11}$, wherein e is 0, 1, 2 or 3,
(s) —CN,
(t) —$NR^{10}R^{10}$,
(u) —$NHSO_2R^{11}$,
(v) —$NR^{12}COR^{11}$,
(w) —$NO_2$,
(x) —$CONR^{10}R^{10}$,
(y) —CO—$R^{11}$, and
(z) aryl,
$R^2$ is a group selected from:
(a) hydrogen
(b) halogen,
(c) $C_{1-6}$-alkyl,
(d) fluoro-$C_{1-6}$-alkyl,
(e) $C_{3-7}$-cycloalkyl,
(f) fluoro-$C_{3-7}$-cycloalkyl,
(j) hydroxy-$C_{1-4}$-alkyl,
(k) hydroxy,
(l) $C_{1-6}$-alkoxy,
(m) fluoro-$C_{1-6}$-alkoxy,
(n) $C_{3-7}$-cycloalkoxy,
(o) fluoro-$C_{3-7}$-cycloalkoxy,
(p) —$SCF_3$,
(q) —$SCF_2H$,
(r) —$SO_2NR^{10}R^{10}$,
(s) —$S(O)_eR^{11}$, wherein e is 0, 1, 2 or 3,
(t) —CN,
(u) —$NR^{10}R^{10}$,
(v) —$NR^{12}SO_2R^{11}$,
(w) —$NR^{12}COR^{11}$,
(x) —$CONR^{10}R^{10}$,
(y) —$OCONR^{10}R^{10}$,
(z) —CO—$R^{11}$;
$R^3$ is a group selected from:
(a) hydrogen,
(b) halogen,
(c) $C_{1-6}$-alkyl,
(d) $C_{3-7}$-cycloalkyl,
(e) hydroxy-$C_{1-4}$-alkyl,
(f) $C_{3-7}$-cycloalkyl-hydroxy-$C_{1-4}$-alkyl,
(g) —CO—$R^{11}$,
(h) —CN,
(i) aryl, and
(j) heteroaryl;
wherein any heteroaryl or aryl residue is optionally independently substituted in one or more positions with a substituent selected from:
(a) halogen,
(b) $C_{1-4}$-alkyl,
(c) $C_{1-4}$-alkylthio,
(d) $C_{1-4}$-alkoxy,
(e) —$CF_3$,
(f) —CN, and
(g) hydroxymethyl;
$R^4$ is a group selected from:
(a) hydrogen,
(b) $C_{1-4}$-alkyl,
(c) fluoro-$C_{1-4}$-alkyl,
(d) $C_{3-5}$-cycloalkyl,
(e) fluoro-$C_{3-5}$-cycloalkyl, and
(f) hydroxy-$C_{1-4}$-alkyl;
$R^5$ is a group selected from:
(a) hydrogen,
(b) $C_{1-4}$-alkyl,
(c) fluoro-$C_{1-4}$-alkyl,
(d) 2-cyanoethyl,
(e) hydroxy-$C_{2-4}$-alkyl,
(g) $C_{3-7}$-cycloalkyl,
(h) fluoro-$C_{3-7}$-cycloalkyl,
(i) $C_{3-4}$-cycloalkyl-$C_{1-4}$-alkyl, and
(j) $C_{1-4}$-alkoxy-$C_{2-4}$-alkyl, or
$R^5$ and one of $R^6$, $R^7$, $R^8$, or $R^9$ groups together with the atoms to which they are attached form a heterocyclic ring and the other three of $R^6$, $R^7$, $R^8$ or $R^9$ are hydrogen;
$R^6$, $R^7$, $R^8$, and $R^9$ are each independently selected from:
(a) hydrogen,
(b) $C_{1-6}$-alkyl,
(c) fluoro-$C_{1-6}$-alkyl,
(d) hydroxy-$C_{1-4}$-alkyl,
with the proviso that three of $R^6$, $R^7$, $R^8$ and $R^9$ are hydrogen unless at least two of $R^6$, $R^7$, $R^8$ and $R^9$ are methyl and the remainder of them are hydrogen,
two of the $R^6$, $R^7$, $R^8$, or $R^9$ groups together with the atoms to which they are attached form a carbocyclic or heterocyclic ring and the other two of $R^6$, $R^7$, $R^8$ or $R^9$ are hydrogen, or
one of $R^6$, $R^7$, $R^8$, or $R^9$ groups and $R^5$ together with the atoms to which they are attached form a heterocyclic ring and the other three of $R^6$, $R^7$, $R^8$ or $R^9$ are hydrogen;
$R^{10}$ is each independently selected from:
(a) hydrogen,
(b) $C_{1-6}$-alkyl,
(c) fluoro-$C_{2-6}$-alkyl, and
(d) $C_{3-7}$-cycloalkyl, or
two $R^{10}$ groups together with the nitrogen to which they are attached form a heterocyclic ring optionally substituted with methyl;
$R^{11}$ is each independently selected from:
(a) $C_{1-6}$-alkyl,
(b) fluoro-$C_{1-6}$-alkyl,
(c) $C_{3-7}$-cycloalkyl,
(d) methyl-$C_{3-7}$-cycloalkyl,
(e) aryl, and
(f) heteroaryl,
wherein any heteroaryl or aryl residue is optionally independently substituted in one or more positions with a substituent selected from:
(a) halogen,
(b) $C_{1-4}$-alkyl,
(c) $C_{1-4}$-alkylthio,
(d) $C_{1-4}$-alkoxy,
(e) —$CF_3$,
(f) —CN, and
(g) hydroxymethyl;

$R^{12}$ is each independently a group selected from:
(a) hydrogen,
(b) $C_{1-6}$-alkyl,
(c) fluoro-$C_{1-6}$-alkyl,
(d) $C_{3-7}$-cycloalkyl, and
(e) hydroxy-$C_{1-4}$-alkyl;
or $R^{11}$ and $R^{12}$ together with the atoms to which they are attached form a lactam ring when present in the group $NR^{12}COR^{11}$, or $R^{11}$ and $R^{12}$ together with the atoms to which they are attached form a sultam ring when present in the group $NR^{12}SO_2R^{11}$, and
pharmaceutically acceptable salts, hydrates, solvates, geometrical isomers, tautomers, optical isomers, and prodrug forms thereof.

A further preferred group of compounds of Formula (II) are those wherein:
⸺ represents a single bond or a double bond;
X=O;
$R^1$ is selected from aryl and heteroaryl, wherein any heteroaryl or aryl residue is optionally independently substituted in one or more positions with a substituent selected from:
(a) halogen,
(b) $C_{1-3}$-alkyl,
(c) trifluoromethyl,
(d) methoxy,
(e) trifluoromethoxy,
(f) methylsulfonyl,
(g) —CN, and
(h) phenyl;
$R^2$ is a group selected from:
(a) hydrogen
(b) halogen,
(c) $C_{1-6}$-alkyl, and
(d) $C_{1-6}$ alkoxy;
$R^3$ is a group selected from:
(a) hydrogen,
(b) halogen,
(c) $C_{1-6}$-alkyl,
(d) hydroxy-$C_{1-4}$-alkyl,
(e) $C_{3-7}$-cycloalkyl-hydroxy-$C_{1-4}$-alkyl, and
(f) —CO—$C_{1-6}$-alkyl;
$R^4$ is a group selected from hydrogen and $C_{1-4}$-alkyl;
$R^5$ is selected from hydrogen, $C_{1-3}$-alkyl and fluoro-$C_{1-3}$-alkyl; or
$R^5$ and one of $R^6$ and $R^8$ together with the nitrogen and carbon atoms to which they are attached form a pyrrolidine ring, provided that $R^7$ and $R^9$ both are hydrogen;
$R^6$ is hydrogen, or together with $R^5$ and the nitrogen and carbon atoms to which they are attached form a pyrrolidine ring, provided that $R^7$ and $R^9$ both are hydrogen;
$R^7$ is selected from hydrogen and methyl:
$R^8$ is hydrogen, or together with $R^5$ and the nitrogen and carbon atoms to which they are attached together form a pyrrolidine ring, provided that $R^7$ and $R^9$ both are hydrogen;
$R^9$ is selected from hydrogen and methyl.

A yet further preferred group of compounds of Formula (II) are those wherein:
⸺ represents a single bond or a double bond;
X=O;
$R^1$ is selected from phenyl, naphthyl, pyridinyl, isoxazolyl, imidazolyl, 1,4-benzodioxinyl, benzofuranyl, furanyl, 1,3-benzothiazolyl, chromanyl, thienyl and benzothienyl, each of which is optionally independently substituted in one or two positions with a substituent selected from
(a) halogen selected from fluorine and chlorine,
(b) $C_{1-3}$-alkyl,
(c) trifluoromethyl,
(d) methoxy,
(e) trifluoromethoxy,
(f) methylsulfonyl,
(g) —CN, and
(h) phenyl
$R^2$ is hydrogen, fluoro, methyl or methoxy;
$R^3$ is hydrogen, chloro, methyl, 1-hydroxy-ethyl, 1-hydroxy-1-methyl-ethyl, acetyl, isobutyryl or cyclopropyl-hydroxymethyl;
$R^4$ is selected from hydrogen, methyl and isopropyl;
$R^5$ is selected from hydrogen, methyl, ethyl, isopropyl, and 2-fluoroeth-1-yl; or
$R^5$ and one of $R^6$ and $R^8$ together with the nitrogen and carbon atoms to which they are attached form a pyrrolidine ring, provided that $R^7$ and $R^9$ both are hydrogen;
$R^6$ is hydrogen or $R^6$ together with $R^5$ and the nitrogen and carbon atoms to which they are attached form a pyrrolidine ring, provided that $R^7$ and $R^9$ both are hydrogen;
$R^7$ is selected from hydrogen and methyl;
$R^8$ is hydrogen or together with $R^5$ and the nitrogen and carbon atoms to which they are attached together form a pyrrolidine ring, provided that $R^7$ and $R^9$ both are hydrogen;
$R^9$ is selected from hydrogen and methyl.

A still yet further preferred group of compounds of Formula (II) are those wherein:
⸺ represents a single bond or a double bond;
X=O;
$R^1$ is selected from phenyl, 1-naphthyl, 2-naphthyl, 3-pyridinyl, 4-isoxazolyl, 4-imidazolyl, 1,4-benzodioxin-6-yl, 2-benzofuranyl, 3-furyl, 1,3-benzothiazol-6-yl, 6-chromenyl, 2-thienyl, 3-thienyl, 2-benzothienyl, and 3-benzothienyl each of which is optionally independently substituted in one or two positions with a substituent selected from
(a) fluorine,
(b) chlorine,
(c) methyl,
(d) propyl,
(e) isopropyl,
(f) trifluoromethyl,
(g) methoxy,
(h) trifluoromethoxy,
(i) methylsulfonyl,
(j) —CN, and
(k) phenyl;
$R^2$ is hydrogen, fluoro, methyl or methoxy;
$R^3$ is hydrogen, chloro, methyl, 1-hydroxy-ethyl, 1-hydroxy-1-methyl-ethyl, acetyl, isobutyryl or cyclopropyl-hydroxymethyl;
$R^4$ is selected from hydrogen, methyl and isopropyl
$R^5$ is selected from hydrogen, methyl, ethyl, isopropyl, and 2-fluoroeth-1-yl; or
$R^5$ and one of $R^6$ and $R^8$ together with the nitrogen and carbon atoms to which they are attached form a pyrrolidine ring, provided that $R^7$ and $R^9$ both are hydrogen;
$R^6$ is hydrogen, or $R^6$ together with $R^5$ and the nitrogen and carbon atoms to which they are attached form a pyrrolidine ring, provided that $R^7$ and $R^9$ both are hydrogen;

$R^7$ is selected from hydrogen and methyl;
$R^8$ is hydrogen or $R^8$ together with $R^5$ and the nitrogen and carbon atoms to which they are attached together form a pyrrolidine ring, provided that $R^7$ and $R^9$ both are hydrogen;
$R^9$ is selected from hydrogen and methyl.

Preferred compounds of the formula (I) include:

2,5-methylene-9-(phenylsulfonyl)-1,2,3,4,5,9-hexahydro [1,5]oxazocino[3,2-e]indole;
2,4-dimethyl-8-(phenylsulfonyl)-1,3,4,8-tetrahydro-2H-[1,4]oxazepino[6,7-e]indole;
2-isopropyl-8-(phenylsulfonyl)-1,3,4,8-tetrahydro-2H-[1,4]oxazepino[6,7-e]indole;
2-ethyl-8-(phenylsulfonyl)-1,3,4,8-tetrahydro-2H-[1,4]oxazepino[6,7-e]indole;
2-methyl-8-(phenylsulfonyl)-1,3,4,8-tetrahydro-2H-[1,4]oxazepino[6,7-e]indole;
8-(2,3-dihydro-1,4-benzodioxin-6-ylsulfonyl)-2-methyl-1,3,4,8-tetrahydro-2H-[1,4]oxazepino[6,7-e]indole;
8-[(3,4-dimethoxyphenyl)sulfonyl]-2-methyl-1,3,4,8-tetrahydro-2H-[1,4]oxazepino[6,7-e]indole;
8-(1-benzofuran-2-ylsulfonyl)-2-methyl-1,3,4,8-tetrahydro-2H-[1,4]oxazepino[6,7-e]indole;
8-[(2,5-dimethyl-3-furyl)sulfonyl]-2-methyl-1,3,4,8-tetrahydro-2H-[1,4]oxazepino[6,7-e]indole;
8-(1,3-benzothiazol-6-ylsulfonyl)-2-methyl-1,3,4,8-tetrahydro-2H-[1,4]oxazepino[6,7-e]indole;
2-methyl-8-{[4-(methylsulfonyl)phenyl]sulfonyl}-1,3,4,8-tetrahydro-2H-[1,4]oxazepino[6,7-e]indole;
8-[(4-isopropylphenyl)sulfonyl]-2-methyl-1,3,4,8-tetrahydro-2H-[1,4]oxazepino[6,7-e]indole;
8-[(2,2-dimethyl-3,4-dihydro-2H-chromen-6-yl)sulfonyl]-2-methyl-1,3,4,8-tetrahydro-2H-[1,4]oxazepino[6,7-e]indole;
8-[(2-chloro-4-fluorophenyl)sulfonyl]-2-methyl-1,3,4,8-tetrahydro-2H-[1,4]oxazepino[6,7-e]indole;
8-[(3,4-dichlorophenyl)sulfonyl]-2-methyl-1,3,4,8-tetrahydro-2H-[1,4]oxazepino[6,7-e]indole;
8-[(4-fluorophenyl)sulfonyl]-2-methyl-1,3,4,8-tetrahydro-2H-[1,4]oxazepino[6,7-e]indole;
8-[(2,6-difluorophenyl)sulfonyl]-2-methyl-1,3,4,8-tetrahydro-2H-[1,4]oxazepino[6,7-e]indole;
2-methyl-8-{[4-(trifluoromethoxy)phenyl]sulfonyl}-1,3,4,8-tetrahydro-2H-[1,4]oxazepino[6,7-e]indole;
2-methyl-8-(2-naphthylsulfonyl)-1,3,4,8-tetrahydro-2H-[1,4]oxazepino[6,7-e]indole;
8-[(3-chloro-4-methylphenyl)sulfonyl]-2-methyl-1,3,4,8-tetrahydro-2H-[1,4]oxazepino[6,7-e]indole;
8-[(4,5-dichloro-2-thienyl)sulfonyl]-2-methyl-1,3,4,8-tetrahydro-2H-[1,4]oxazepino[6,7-e]indole;
8-[(5-chloro-3-methyl-1-benzothien-2-yl)sulfonyl]-2-methyl-1,3,4,8-tetrahydro-2H-[1,4]oxazepino[6,7-e]indole;
8-[(2,4-dichlorophenyl)sulfonyl]-2-methyl-1,3,4,8-tetrahydro-2H-[1,4]oxazepino[6,7-e]indole;
8-{[4-fluoro-3-(trifluoromethyl)phenyl]sulfonyl}-2-methyl-1,3,4,8-tetrahydro-2H-[1,4]oxazepino[6,7-e]indole;
2-methyl-8-(2-thienylsulfonyl)-1,3,4,8-tetrahydro-2H-[1,4]oxazepino[6,7-e]indole;
2-methyl-8-[(4-methylphenyl)sulfonyl]-1,3,4,8-tetrahydro-2H-[1,4]oxazepino[6,7-e]indole;
8-[(2-methoxy-5-methylphenyl)sulfonyl]-2-methyl-1,3,4,8-tetrahydro-2H-[1,4]oxazepino[6,7-e]indole;
8-[(3-fluoro-4-methylphenyl)sulfonyl]-2-methyl-1,3,4,8-tetrahydro-2H-[1,4]oxazepino[6,7-e]indole;
8-(1-benzothien-3-ylsulfonyl)-2-methyl-1,3,4,8-tetrahydro-2H-[1,4]oxazepino[6,7-e]indole;
8-[(4-methoxyphenyl)sulfonyl]-2-methyl-1,3,4,8-tetrahydro-2H-[1,4]oxazepino[6,7-e]indole;
2-methyl-8-{[4-(trifluoromethyl)phenyl]sulfonyl}-1,3,4,8-tetrahydro-2H-[1,4]oxazepino[6,7-e]indole;
2-methyl-8-[(4-propylphenyl)sulfonyl]-1,3,4,8-tetrahydro-2H-[1,4]oxazepino[6,7-e]indole;
3-chloro-4-[(2-methyl-1,2,3,4-tetrahydro-8H-[1,4]oxazepino[6,7-e]indol-8-yl)sulfonyl]benzonitrile;
8-[(2,5-dimethyl-3-thienyl)sulfonyl]-2-methyl-1,3,4,8-tetrahydro-2H-[1,4]oxazepino[6,7-e]indole;
2-[(2-methyl-1,2,3,4-tetrahydro-8H-[1,4]oxazepino[6,7-e]indol-8-yl)sulfonyl]benzonitrile;
2-methyl-1-[2-methyl-8-(phenylsulfonyl)-1,3,4,8-tetrahydro-2H-[1,4]oxazepino[6,7-e]indol-9-yl]propan-1-one;
1-[2-methyl-8-(phenylsulfonyl)-1,3,4,8-tetrahydro-2H-[1,4]oxazepino[6,7-e]indol-9-yl]ethanone;
9-chloro-2-methyl-8-(phenylsulfonyl)-1,3,4,8-tetrahydro-2H-[1,4]oxazepino[6,7-e]indole;
2-[2-methyl-8-(phenylsulfonyl)-1,3,4,8-tetrahydro-2H-[1,4]oxazepino[6,7-e]indol-9-yl]propan-2-ol;
cyclopropyl[2-methyl-8-(phenylsulfonyl)-1,3,4,8-tetrahydro-2H-[1,4]oxazepino[6,7-e]indol-9-yl]methanol;
1-[2-methyl-8-(phenylsulfonyl)-1,3,4,8-tetrahydro-2H-[1,4]oxazepino[6,7-e]indol-9-yl]ethanol;
10-chloro-2-methyl-8-(phenylsulfonyl)-1,3,4,8-tetrahydro-2H-[1,4]oxazepino[6,7-e]indole;
(7aR)-3-(phenylsulfonyl)-3,7a,8,9,10,12-hexahydro-7H-pyrrolo[2',1':3,4][1,4]oxazepino[6,7-e]indole;
(7aS)-3-(phenylsulfonyl)-3,7a,8,9,10,12-hexahydro-7H-pyrrolo[2',1':3,4][1,4]oxazepino[6,7-e]indole;
(3S)-3-methyl-8-(phenylsulfonyl)-1,3,4,8-tetrahydro-2H-[1,4]oxazepino[6,7-e]indole;
(3S)-2,3-dimethyl-8-(phenylsulfonyl)-1,3,4,8-tetrahydro-2H-[1,4]oxazepino[6,7-e]indole;
2,7-dimethyl-8-(phenylsulfonyl)-1,3,4,8-tetrahydro-2H-[1,4]oxazepino[6,7-e]indole;
6-methoxy-2-methyl-8-(phenylsulfonyl)-1,3,4,8-tetrahydro-2H-[1,4]oxazepino[6,7-e]indole;
8-(phenylsulfonyl)-1,3,4,8-tetrahydro-2H-[1,4]oxazepino[6,7-e]indole;
2-(2-fluoroethyl)-8-(phenylsulfonyl)-1,3,4,8-tetrahydro-2H-[1,4]oxazepino[6,7-e]indole;
8-[(2-methoxy-5-methylphenyl)sulfonyl]-1,3,4,8-tetrahydro-2H-[1,4]oxazepino[6,7-e]indole;
8-[(2,4-dichlorophenyl)sulfonyl]-1,3,4,8-tetrahydro-2H-[1,4]oxazepino[6,7-e]indole;
8-{[3-(trifluoromethyl)phenyl]sulfonyl}-1,3,4,8-tetrahydro-2H-[1,4]oxazepino[6,7-e]indole;
8-[(3,4-dimethoxyphenyl)sulfonyl]-1,3,4,8-tetrahydro-2H-[1,4]oxazepino[6,7-e]indole;
8-(2-naphthylsulfonyl)-1,3,4,8-tetrahydro-2H-[1,4]oxazepino[6,7-e]indole;
8-[(2-methoxy-4-methylphenyl)sulfonyl]-1,3,4,8-tetrahydro-2H-[1,4]oxazepino[6,7-e]indole;
8-[(4-propylphenyl)sulfonyl]-1,3,4,8-tetrahydro-2H-[1,4]oxazepino[6,7-e]indole;
8-[(4-isopropylphenyl)sulfonyl]-1,3,4,8-tetrahydro-2H-[1,4]oxazepino[6,7-e]indole;
8-(1-benzofuran-2-ylsulfonyl)-1,3,4,8-tetrahydro-2H-[1,4]oxazepino[6,7-e]indole;
8-[(2,5-dimethyl-3-thienyl)sulfonyl]-1,3,4,8-tetrahydro-2H-[1,4]oxazepino[6,7-e]indole;

8-[(3-fluoro-4-methylphenyl)sulfonyl]-1,3,4,8-tetrahydro-2H-[1,4]oxazepino[6,7-e]indole;
8-[(4-methoxyphenyl)sulfonyl]-1,3,4,8-tetrahydro-2H-[1,4]oxazepino[6,7-e]indole;
8-[(2,5-dimethyl-3-furyl)sulfonyl]-1,3,4,8-tetrahydro-2H-[1,4]oxazepino[6,7-e]indole;
8-[(2-methylphenyl)sulfonyl]-1,3,4,8-tetrahydro-2H-[1,4]oxazepino[6,7-e]indole;
8-[(4-methylphenyl)sulfonyl]-1,3,4,8-tetrahydro-2H-[1,4]oxazepino[6,7-e]indole;
8-(2-thienylsulfonyl)-1,3,4,8-tetrahydro-2H-[1,4]oxazepino[6,7-e]indole;
8-{[2-(trifluoromethoxy)phenyl]sulfonyl}-1,3,4,8-tetrahydro-2H-[1,4]oxazepino[6,7-e]indole;
8-(biphenyl-3-ylsulfonyl)-1,3,4,8-tetrahydro-2H-[1,4]oxazepino[6,7-e]indole;
8-{[2-(trifluoromethyl)phenyl]sulfonyl}-1,3,4,8-tetrahydro-2H-[1,4]oxazepino[6,7-e]indole;
8-(1-benzothien-2-ylsulfonyl)-1,3,4,8-tetrahydro-2H-[1,4]oxazepino[6,7-e]indole;
8-(1-naphthylsulfonyl)-1,3,4,8-tetrahydro-2H-[1,4]oxazepino[6,7-e]indole;
8-[(5-fluoro-2-methylphenyl)sulfonyl]-1,3,4,8-tetrahydro-2H-[1,4]oxazepino[6,7-e]indole;
(3R)-3-methyl-8-(phenylsulfonyl)-1,3,4,8-tetrahydro-2H-[1,4]oxazepino[6,7-e]indole;
(3R)-2,3-dimethyl-8-(phenylsulfonyl)-1,3,4,8-tetrahydro-2H-[1,4]oxazepino[6,7-e]indole;
6-methoxy-8-(phenylsulfonyl)-1,3,4,8-tetrahydro-2H-[1,4]oxazepino[6,7-e]indole;
9-methyl-8-(phenylsulfonyl)-1,3,4,8-tetrahydro-2H-[1,4]oxazepino[6,7-e]indole;
10-chloro-8-(phenylsulfonyl)-1,3,4,8-tetrahydro-2H-[1,4]oxazepino[6,7-e]indole;
10-chloro-8-[(4-fluorophenyl)sulfonyl]-1,3,4,8-tetrahydro-2H-[1,4]oxazepino[6,7-e]indole;
3-[(10-chloro-1,2,3,4-tetrahydro-8H-[1,4]oxazepino[6,7-e]indol-8-yl)sulfonyl]benzonitrile;
10-chloro-8-(pyridin-3-ylsulfonyl)-1,3,4,8-tetrahydro-2H-[1,4]oxazepino[6,7-e]indole;
8-[(2-chlorophenyl)sulfonyl]-1,3,4,8-tetrahydro-2H-[1,4]oxazepino[6,7-e]indole;
1-methyl-8-(phenylsulfonyl)-1,3,4,8-tetrahydro-2H-[1,4]oxazepino[6,7-e]indole;
(1S)-1-methyl-8-(phenylsulfonyl)-1,3,4,8-tetrahydro-2H-[1,4]oxazepino[6,7-e]indole;
(1R)-1-methyl-8-(phenylsulfonyl)-1,3,4,8-tetrahydro-2H-[1,4]oxazepino[6,7-e]indole;
1-methyl-8-(phenylsulfonyl)-3,8-dihydro-4H-[1,4]oxazepino[6,7-e]indole;
6-fluoro-1-methyl-8-(phenylsulfonyl)-1,3,4,8-tetrahydro-2H-[1,4]oxazepino[6,7-e]indole;
6-methoxy-1-methyl-8-(phenylsulfonyl)-1,3,4,8-tetrahydro-2H-[1,4]oxazepino[6,7-e]indole;
8-[(2-chlorophenyl)sulfonyl]-6-methoxy-1-methyl-1,3,4,8-tetrahydro-2H-[1,4]oxazepino[6,7-e]indole;
6-methoxy-1-methyl-8-[(2-methylphenyl)sulfonyl]-1,3,4,8-tetrahydro-2H-[1,4]oxazepino[6,7-e]indole;
8-[(2,6-difluorophenyl)sulfonyl]-6-methoxy-1-methyl-1,3,4,8-tetrahydro-2H-[1,4]oxazepino[6,7-e]indole;
6-methoxy-8-[(2-methoxy-5-methylphenyl)sulfonyl]-1-methyl-1,3,4,8-tetrahydro-2H-[1,4]oxazepino[6,7-e]indole;
8-[(2,4-dichlorophenyl)sulfonyl]-6-methoxy-1-methyl-1,3,4,8-tetrahydro-2H-[1,4]oxazepino[6,7-e]indole;
1-isopropyl-8-(phenylsulfonyl)-1,3,4,8-tetrahydro-2H-[1,4]oxazepino[6,7-e]indole;
1-isopropyl-2-methyl-8-(phenylsulfonyl)-1,3,4,8-tetrahydro-2H-[1,4]oxazepino[6,7-e]indole;
1,2-dimethyl-8-(phenylsulfonyl)-1,3,4,8-tetrahydro-2H-[1,4]oxazepino[6,7-e]indole;
10-chloro-1-methyl-8-(phenylsulfonyl)-3,8-dihydro-4H-[1,4]oxazepino[6,7-e]indole;
10-chloro-1-methyl-8-(pyridin-3-ylsulfonyl)-1,3,4,8-tetrahydro-2H-[1,4]oxazepino[6,7-e]indole;
10-chloro-1-methyl-8-(phenylsulfonyl)-1,3,4,8-tetrahydro-2H-[1,4]oxazepino[6,7-e]indole;
10-chloro-1,2-dimethyl-8-(phenylsulfonyl)-1,3,4,8-tetrahydro-2H-[1,4]oxazepino[6,7-e]indole;
10-chloro-8-[(2-methoxy-5-methylphenyl)sulfonyl]-1-methyl-1,3,4,8-tetrahydro-2H-[1,4]oxazepino[6,7-e]indole;
10-chloro-8-[(2-methoxy-5-methylphenyl)sulfonyl]-1,2-dimethyl-1,3,4,8-tetrahydro-2H-[1,4]oxazepino[6,7-e]indole;
10-chloro-8-[(2-fluorophenyl)sulfonyl]-1-methyl-1,3,4,8-tetrahydro-2H-[1,4]oxazepino[6,7-e]indole;
10-chloro-8-[(2-fluorophenyl)sulfonyl]-1,2-dimethyl-1,3,4,8-tetrahydro-2H-[1,4]oxazepino[6,7-e]indole;
10-chloro-8-[(3-fluorophenyl)sulfonyl]-1-methyl-1,3,4,8-tetrahydro-2H-[1,4]oxazepino[6,7-e]indole;
10-chloro-8-[(3-fluorophenyl)sulfonyl]-1,2-dimethyl-1,3,4,8-tetrahydro-2H-[1,4]oxazepino[6,7-e]indole;
1-methyl-8-(pyridin-3-ylsulfonyl)-1,3,4,8-tetrahydro-2H-[1,4]oxazepino[6,7-e]indole;
8-[(2-chlorophenyl)sulfonyl]-1-methyl-1,3,4,8-tetrahydro-2H-[1,4]oxazepino[6,7-e]indole;
1-methyl-8-[(2-methylphenyl)sulfonyl]-1,3,4,8-tetrahydro-2H-[1,4]oxazepino[6,7-e]indole;
8-[(2,6-difluorophenyl)sulfonyl]-1-methyl-1,3,4,8-tetrahydro-2H-[1,4]oxazepino[6,7-e]indole;
8-[(2,4-dichlorophenyl)sulfonyl]-1-methyl-1,3,4,8-tetrahydro-2H-[1,4]oxazepino[6,7-e]indole;
8-[(2-methoxy-5-methylphenyl)sulfonyl]-1-methyl-1,3,4,8-tetrahydro-2H-[1,4]oxazepino[6,7-e]indole;
8-[(2-methoxy-4-methylphenyl)sulfonyl]-1-methyl-1,3,4,8-tetrahydro-2H-[1,4]oxazepino[6,7-e]indole;
8-[(2,5-dimethyl-3-thienyl)sulfonyl]-1-methyl-1,3,4,8-tetrahydro-2H-[1,4]oxazepino[6,7-e]indole;
8-[(2,5-dimethyl-3-furyl)sulfonyl]-1-methyl-1,3,4,8-tetrahydro-2H-[1,4]oxazepino[6,7-e]indole;
1-methyl-8-(2-thienylsulfonyl)-1,3,4,8-tetrahydro-2H-[1,4]oxazepino[6,7-e]indole;
1-methyl-8-[(5-methylisoxazol-4-yl)sulfonyl]-1,3,4,8-tetrahydro-2H-[1,4]oxazepino[6,7-e]indole;
8-[(1,2-dimethyl-1H-imidazol-4-yl)sulfonyl]-1-methyl-1,3,4,8-tetrahydro-2H-[1,4]oxazepino[6,7-e]indole;
and the pharmaceutically acceptable salts thereof.

The compounds of Formula (I) may be agonists, partial agonists or antagonists for the 5-HT$_6$ receptor. Preferably, the compounds act as partial agonists or antagonists for the 5-HT$_6$ receptor. More preferably the compounds act as antagonists for the 5-HT$_6$ receptor. The term "partial agonist of the 5-HT$_6$ receptor" means a compound which binds to the human 5-HT$_6$ receptor and does not fully antagonize 5-HT-induced cAMP formation in the intrinsic activity assay described herein (see "Biological Tests").

Another object of the present invention is a compound of Formula (I) for use in therapy, especially for use in the treatment or prophylaxis of a 5-HT$_6$ receptor-related disorder.

Examples of 5-HT$_6$ receptor-related disorders include: obesity, type II diabetes, disorders of the central nervous system such as anxiety, depression, panic attacks, memory disorders, cognitive disorders, epilepsy, sleep disorders, migraine, anorexia, bulimia, binge eating disorders, obsessive compulsive disorders, psychoses, Alzheimer's disease, Parkinson's disease, Huntington's chorea, schizophrenia, attention deficit hyperactive disorder (ADHD), withdrawal from drug abuse (e.g. abuse of cocaine, amphetamine and/or nicotine), neurodegenerative diseases characterized by impaired neuronal growth, and pain.

Another object of the present invention is a pharmaceutical formulation comprising a compound of Formula (I) as active ingredient, in combination with a pharmaceutically acceptable diluent or carrier, especially for use in the treatment or prophylaxis of a 5-$HT_6$ receptor-related disorder.

Another object of the present invention is a method for treating a human or animal subject suffering from a 5-$HT_6$ receptor-related disorder. The method can include administering to a subject (e.g., a human or an animal, dog, cat, horse, cow) in need thereof an effective amount of one or more compounds of Formula (I), their salts, or compositions containing the compounds or salts.

Another object of the present invention is a method for reducing body weight or reducing body weight gain. The method comprises administering to a subject in need thereof an effective amount of a compound of the Formula (I).

The methods delineated herein can also include the step of identifying that the subject is in need of treatment of the 5-$HT_6$ receptor-related disorder. Identifying a subject in need of such treatment can be in the judgment of a subject or a health care professional and can be subjective (e.g., opinion) or objective (e.g., measurable by a test or diagnostic method).

Another object of the present invention is a cosmetic composition for oral administration comprising a compound as mentioned above as active ingredient, in combination with a diluent, excipient or carrier, adapted for oral administration to achieve reduction of body weight and/or of body weight gain.

In accordance with the use according to the invention, the cosmetic composition is provided in all the pharmaceutical forms normally used for oral administration, in particular in the form of tablets which may or may not be breakable, of granules, of capsules, of gelatin capsules, of solutes, of suspensions or of solutions.

Another object of the present invention is a process for the preparation of a compound according to formula (I) of the invention comprising one or more of the following steps:

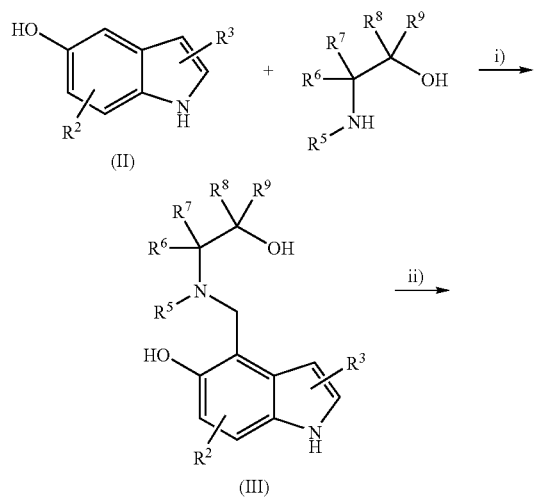

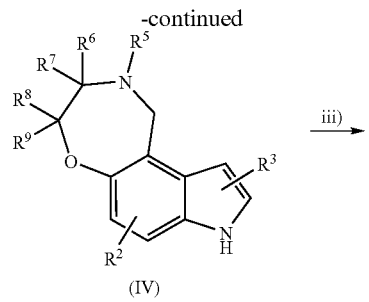

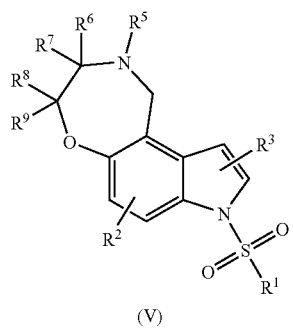

i) paraformaldehyde, ii) Mitsunobu conditions, iii) $R^1$-sulfonyl chloride and optionally thereafter forming a pharmaceutically acceptable salt of the compound of formula (I).

Another object of the present invention is a process for the preparation of a compound according to any of the formulae herein (e.g., formula (I)) using one or more of the synthetic procedures, intermediates, reagents or conditions delineated in the examples herein.

The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, R, R', X, etc.) or not.

The chemicals used in the synthetic routes delineated herein may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds.

In addition, various synthetic steps may be performed in an alternate sequence or order to give the desired compounds. Synthetic chemistry transformations useful in synthesizing applicable compounds are known in the art and include, for example, those is described in R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Methods for carrying out the reactions described above are well known to those skilled in the art. The necessary starting materials for preparing the compounds of formula (I) are either known or may be prepared in analogy with the preparation of known compounds.

The compounds of formula (I) may possess one or more chiral carbon atoms, and they may therefore be obtained in the form of optical isomers, e.g. as a pure enantiomer, or as a mixture of enantiomers (racemate) or as a mixture containing diastereomers. The separation of mixtures of optical isomers to obtain pure enantiomers is well known in the art and may, for example, be achieved by fractional crystallization of salts with optically active (chiral) acids or by chromatographic separation on chiral columns. All isomeric forms possible (pure enantiomers, diastereomers, tautomers, racemic mixtures and unequal mixtures of two enantiomers) for the compounds delineated are within the scope of the invention. When the compounds described herein contain olefinic double bonds of geometric asymmetry, it is intended to include both trans and cis (E and Z) geometric isomers.

The compounds of the formula (I) may be used as such or, where appropriate, as pharmacologically acceptable salts (acid or base addition salts) thereof. The pharmacologically acceptable addition salts mentioned above are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as formic acid, acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

For clinical use, the compounds of the invention are formulated into pharmaceutical formulations for oral, rectal, parenteral or other mode of administration. Pharmaceutical formulations are usually prepared by mixing the active substance, or a pharmaceutically acceptable salt thereof, with conventional pharmaceutical excipients. Examples of excipients are water, gelatin, gum arabicum, lactose, microcrystalline cellulose, starch, sodium starch glycolate, calcium hydrogen phosphate, magnesium stearate, talcum, colloidal silicon dioxide, and the like. Such formulations may also contain other pharmacologically active agents, and conventional additives, such as stabilizers, wetting agents, emulsifiers, flavouring agents, buffers, and the like. Usually, the amount of active compounds is between 0.1-95% by weight of the preparation, preferably between 0.2-20% by weight in preparations for parentral use and more preferably between 1-50% by weight in preparations for oral administration.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

Cosmetic compositions have active ingredients combined with a diluent, excipient or carrier adapted for oral administration and can contain, for example, water, gelatin, lactose, starch, talc, vaseline, gum arabic, polyalkylene glycols and magnesium stearate. The cosmetic compositions may be in the form of tablets, powders, granules, lozenges, gelatin capsules, supsension or solutions. The tablets, powders, granules, lozenges or gelatin capsules can contain binders, fillers, pulverulent carriers; the solutions or suspensions can contain diluents, solvents and thickeners.

Definitions

The following definitions shall apply throughout the specification and the appended claims.

Unless otherwise stated or indicated, the term "$C_{1-6}$-alkyl" denotes a straight or branched alkyl group having from 1 to 6 carbon atoms. Examples of said $C_{1-6}$-alkyl include methyl, ethyl, n-propyl, iso-propyl, n-butyl, iso-butyl, sec-butyl, t-butyl and straight- and branched-chain pentyl and hexyl. For parts of the range "$C_{1-6}$-alkyl" all subgroups thereof are contemplated such as $C_{1-5}$-alkyl, $C_{1-4}$-alkyl, $C_{1-3}$-alkyl, $C_{1-2}$-alkyl, $C_{2-6}$-alkyl, $C_{2-5}$-alkyl, $C_{2-4}$-alkyl, $C_{2-3}$-alkyl, $C_{3-6}$-alkyl, $C_{4-5}$-alkyl, etc. Likewise, "aryl-$C_{1-6}$-alkyl" means a $C_{1-6}$-alkyl group substituted by an aryl group. Examples include benzyl, 2-phenylethyl, 1-phenylethyl and 1-naphthylmethyl.

Unless otherwise stated, "fluoro-$C_{1-6}$-alkyl" means a $C_{1-6}$-alkyl group substituted by one or more fluorine atoms. Examples of said fluoro-$C_{1-6}$-alkyl include 2-fluoroethyl, fluoromethyl, trifluoromethyl and 2,2,2-trifluoroethyl.

Unless otherwise stated or indicated, the term "hydroxy-$C_{1-4}$-alkyl" denotes a straight or branched alkyl group that has a hydrogen atom thereof replaced with OH. Examples of said hydroxy-$C_{1-4}$-alkyl include hydroxymethyl, 2-hydroxyethyl, 2-hydroxypropyl and 2-hydroxy-2-methylpropyl.

Unless otherwise stated or indicated, the term "$C_{1-6}$-alkoxy" denotes a straight or branched alkoxy group having from 1 to 6 carbon atoms. Examples of said $C_{1-6}$-alkoxy include methoxy, ethoxy, n-propoxy, iso-propoxy, n-butoxy, iso-butoxy, sec-butoxy, t-butoxy and straight- and branched-chain pentoxy and hexoxy. For parts of the range "$C_{1-6}$-alkoxy" all subgroups thereof are contemplated such as $C_{1-5}$-alkoxy, $C_{1-4}$-alkoxy, $C_{1-3}$-alkoxy, $C_{1-2}$-alkoxy, $C_{2-6}$-alkoxy, $C_{2-5}$-alkoxy, $C_{2-4}$-alkoxy, $C_{2-3}$-alkoxy, $C_{3-6}$-alkoxy, $C_{4-5}$-alkoxy, etc.

Unless otherwise stated or indicated, "fluoro-$C_{1-6}$-alkoxy" means a $C_{1-6}$-alkoxy group substituted by one or more fluorine atoms. Examples of said fluoro-$C_{1-6}$-alkoxy include trifluoromethoxy, difluoromethoxy, monofluoromethoxy, 2-fluoroethoxy, 2,2,2-trifluoroethoxy, and 1,1,2,2-tetrafluoroethoxy.

Unless otherwise stated or indicated, the term "$C_{1-4}$-alkoxy-$C_{2-4}$-alkyl" denotes a straight or branched alkoxy group having from 1 to 4 carbon atoms connected to an alkyl group having from 1 to 4 carbon atoms. Examples of said $C_{1-4}$-alkoxy-$C_{2-4}$-alkyl include methoxymethyl, ethoxymethyl, iso-propoxymethyl, n-butoxymethyl, and t-butoxymethyl. For parts of the range "$C_{1-4}$-alkoxy-$C_{2-4}$-alkyl" all subgroups thereof are contemplated such as $C_{1-3}$-alkoxy-$C_{2-4}$-alkyl, $C_{1-4}$-alkoxy-$C_{2-3}$-alkyl, $C_{1-2}$-alkoxy-$C_{2-3}$-alkyl, $C_{2-4}$-alkoxy-$C_{2-4}$-alkyl, $C_{2-3}$-alkoxy-$C_{2-4}$-alkyl, $C_{2-4}$-alkoxy-$C_{2-3}$-alkyl, etc.

Unless otherwise stated or indicated, the term "$C_{2-6}$-alkenyl" denotes a straight or branched alkenyl group having from 2 to 6 carbon atoms. Examples of said $C_{2-6}$-alkenyl include vinyl, allyl, 2,3-dimethylallyl, 1-butenyl, 1-pentenyl, and 1-hexenyl. For parts of the range "$C_{2-6}$-alkenyl" all subgroups thereof are contemplated such as $C_{2-5}$-alkenyl, $C_{2-4}$-alkenyl, $C_{2-3}$-alkenyl, $C_{3-6}$-alkenyl, $C_{4-5}$-alkenyl, etc. Likewise, "aryl-$C_{2-6}$-alkenyl" means a $C_{2-6}$-alkenyl group substituted by an aryl group. Examples of said aryl-$C_{2-6}$-alkenyl include styryl and cinnamyl.

Unless otherwise stated or indicated, the term "fluoro-$C_{2-6}$-alkenyl" denotes a straight or branched alkenyl group having from 2 to 6 carbon atoms substituted by one or more fluorine atoms. Examples of said fluoro-$C_{2-6}$-alkenyl include 1-fluorovinyl, 1,2-difluorovinyl, trifluorovinyl, and 2-fluoro-2-propen-1-yl.

Unless otherwise stated or indicated, the term "$C_{3-4}$-alkynyl" denotes a straight or branched alkynyl group having from 3 to 4 carbon atoms. Examples of said $C_{3-4}$-alkynyl include 1-propynyl, 2-propynyl, 1-butynyl, 2-butynyl, and 1-methyl-prop-2-yn-1-yl.

Unless otherwise stated or indicated, the term "$C_{3-7}$-cycloalkyl" denotes a cyclic alkyl group having a ring size from 3 to 7 carbon atoms. Said cycloalkyl include cyclopropyl, cyclobutyl, cyclopentyl, cyclohexyl, and cycloheptyl. For parts of the range "$C_{3-7}$-cycloalkyl" all subgroups thereof are contemplated such as $C_{3-6}$-cycloalkyl, $C_{3-5}$-cycloalkyl, $C_{3-4}$-cycloalkyl, $C_{4-7}$-cycloalkyl, $C_{4-6}$-cycloalkyl, $C_{4-5}$-cycloalkyl, $C_{5-7}$-cycloalkyl, $C_{6-7}$-cycloalkyl, etc.

Unless otherwise stated or indicated, the term "methyl-$C_{3-7}$-cycloalkyl" denotes a $C_{3-7}$-cycloalkyl group substituted by one or two methyl groups. Examples of said "methyl-$C_{3-7}$-cycloalkyl" include 4-methylcyclohexyl, 3,3-dimethylcyclopentyl and 1-methylcyclopropyl.

Unless otherwise stated or indicated, the term "methyl-$C_{3-7}$-cycloalkoxy" denotes a $C_{3-7}$-cycloalkoxy group substituted by one or two methyl groups. Examples of said "methyl-$C_{3-7}$-cycloalkoxy" include 4-methylcyclohexyloxy, 3,3-dimethylcyclopentyloxy and 1-methylcyclopropyloxy.

Unless otherwise stated or indicated, the term "fluoro-$C_{3-7}$-cycloalkyl" denotes a $C_{3-7}$-cycloalkyl group substituted by one or two fluorine atoms. Examples of said "fluoro-$C_{3-7}$-cycloalkyl" include 2,2-difluorocyclopropyl and 4-fluorocyclohexyl.

Unless otherwise stated or indicated, the term "fluoro-$C_{3-7}$-cycloalkoxy" denotes a $C_{3-7}$-cycloalkoxy group substituted by one or two fluorine atoms. Examples of said "fluoro-$C_{3-7}$-cycloalkoxy" include 2,2-difluorocyclopropyloxy and 4-fluorocyclohexyloxy.

Unless otherwise stated or indicated, the term "aryl" refers to a hydrocarbon ring system of one, two, or three, preferably one or two, rings, having at least one aromatic ring and having from 6-14, preferably 6-10, carbon atoms. Examples of aryls are phenyl, pentalenyl, indenyl, indanyl, 1,2,3,4-tetrahydronaphthyl, 1-naphthyl, 2-naphthyl, fluorenyl and anthryl. The aryl rings may be optionally substituted. Likewise, aryloxy refers to an aryl group bonded to an oxygen atom.

An aryl group can be linked to the remainder of the molecule through any available ring carbon whether the ring carbon is in an aromatic ring or in a partially saturated ring.

The term "heteroaryl" refers to a mono- or bicyclic aromatic ring system, only one ring need be aromatic, and the said heteroaryl moiety can be linked to the remainder of the molecule via a carbon or nitrogen atom in any ring, and having from 5 to 10 ring atoms (mono- or bicyclic), in which one or more of the ring atoms are other than carbon, such as nitrogen, sulphur, oxygen and selenium. Examples of such heteroaryl rings include furyl, pyrrolyl, thienyl, oxazolyl, isoxazolyl, imidazolyl, thiazolyl, isothiazolyl, pyridinyl, pyrimidinyl, pyrazinyl, chromanyl, quinazolinyl, indolyl, isoindolyl, indolinyl, isoindolinyl, indazolyl, pyrazolyl, pyridazinyl, quinolinyl, isoquinolinyl, benzofuranyl, dihydrobenzofuranyl, benzodioxolyl, benzodioxinyl, benzothienyl, benzimidazolyl, benzothiazolyl, benzothiadiazolyl, and benzotriazolyl groups. If a bicyclic heteroaryl ring is substituted, it may be substituted in any ring.

Unless otherwise stated or indicated, the term "heterocyclic" refers to a non-aromatic (i.e., partially or fully saturated) mono- or bicyclic ring system having 4 to 10 ring atoms with at least one heteroatom such as O, N, or S, and the remaining ring atoms are carbon. Preferably, "heterocyclic" refers to a fully saturated non-aromatic monocyclic ring system with 4 to 7 ring atoms and in which one or two atoms are heteroatoms selected from O, N and S, and the remaining ring atoms are carbon. Examples of heterocyclic groups include piperidyl, tetrahydropyranyl, tetrahydrofuranyl, azepinyl, azetidinyl, pyrrolidinyl, morpholinyl, imidazolinyl, thiomorpholinyl, pyranyl, dioxanyl, and piperazinyl groups. When present in heterocyclic groups, the sulfur atom may optionally be in an oxidized form (i.e., S=O or O=S=O).

Unless otherwise stated or indicated, the term "carbocyclic" refers to a non-aromatic (i.e., partially or fully saturated) monocyclic ring system having 3 to 6 carbon ring atoms. Examples of carbocyclic rings include cyclopropane, cyclobutane, cyclopentane, cyclohexane, cyclopentene, cyclohexene.

Unless otherwise stated or indicated, the term "halogen" shall mean fluorine, chlorine, bromine or iodine.

The term —S(O)$_e$R$^{11}$, wherein e is 0, 1, 2 or 3, has the meaning as illustrated by formula (VI)-(IX):

(VI)

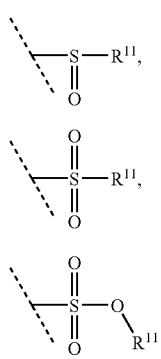

The term "lactam" refers to a lactam group selected from 2-azetidinon-1-yl, 2-pyrrolidon-1-yl and 2-piperidinon-1-yl.

The term "sultam" refers to a sultam group selected from tetrahydro-1,1-dioxido-2H-1,2-thiazin-2-yl and 1,1-dioxido-2-isothiazolidinyl.

"Optional" or "optionally" means that the subsequently described event or circumstance may but need not occur, and that the description includes instances where the event or circumstance occurs and instances in which it does not.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect on the treated subject. The therapeutic effect may be objective (i.e., measurable by some test or marker) or subjective (i.e., subject gives an indication of or feels an effect).

Reference to compounds of "formula I" in embodiments herein also includes compounds of any of the formulae delineated herein.

The term "prodrug forms" means a pharmacologically acceptable derivative, such as an ester or an amide, which derivative is biotransformed in the body to form the active drug. Reference is made to Goodman and Gilman's, The Pharmacological basis of Therapeutics, 8$^{th}$ ed., Mc-Graw-Hill, Int. Ed. 1992, "Biotransformation of Drugs", p. 13-15; and "The Organic Chemistry of Drug Design and Drug Action" by Richard B. Silverman. Chapter 8, p 352. (Academic Press, Inc. 1992. ISBN 0-12-643730-0).

Combinations of substituents and variables envisioned by this invention are only those that result in the formation of stable compounds. The term "stable" as used herein, refers to compounds which possess stability sufficient to allow manufacture and which maintains the integrity of the compound for a sufficient period of time to be useful for the purposes detailed herein (e.g., therapeutic administration to a subject for the treatment of 5-HT6 mediated disease or disorder (including those delineated herein), obesity, type-2 diabetes).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The following abbreviations have been used:
CV means Coefficient of Variation,
DCM means dichloromethane,
DMSO means dimethyl sulphoxide,
EDTA means ethylenediamine tetraacetic acid,
EGTA means ethylenebis(oxyethylenenitrilo)tetraacetic acid,
ESI means electrospray ionization,
HEPES means 4-(2-hydroxyethyl)-1-piperazineethanesulfonic acid,
HPLC means high performance liquid chromatography,
LSD means lysergic acid, diethylamide,
MeCN means acetonitrile,
SPA means Scintillation Proximity Assay,
TFA means trifluoroacetic acid,
THF means tetrahydrofuran,
UV means ultraviolet,
MeOH means methanol,
BnBr means benzyl bromide,
DCE means 1,2-dichloroethane,
TMAD means (E)-N,N,N',N'-tetramethyldiazene-1,2-dicarboxamide.

EXAMPLES

The invention will now be further illustrated by the following non-limiting Examples. The specific examples below are to be construed as merely illustrative, and not limitative of the remainder of the disclosure in any way whatsoever. Without further elaboration, it is believed that one skilled in the art can, based on the description herein, utilize the present invention to its fullest extent. All references and publications cited herein are hereby incorporated by reference in their entirety.

Methods $^1$H nuclear magnetic resonance (NMR) and $^{13}$C NMR were recorded on a Bruker Advance DPX 400 spectrometer at 400.1 and 100.6 MHz, respectively, or alternatively, on a Varian Inova 400 spectrometer at 400.0 and 100.5 MHz respectively, or alternatively, on a Bruker NMR 500 spectrometer at 500.1 MHz and 125.1 MHz, respectively or alternatively, on a JEOL eclipse 270 spectrometer at 270.0 MHz and 67.5 MHz, respectively. All spectra were recorded using residual solvent as internal standard.

Analytical HPLC/MS was performed using an Agilent 1100/1200 Series Liquid Chromatograph/Mass Selective Detector (MSD) (Singel Quadrupole) (1946A/1946C/1956C/6110) equipped with an electrospray interface.

Preparative HPLC/MS was performed on a Waters/Micromass Platform ZQ system and preparative HPLC/UV was performed on a Gilson system.

Preparative flash chromatography was performed on Merck silica gel 60 (230-400 mesh). The compounds were named using ACD Name 6.0 except for the compound in Example 1, 2,5-methylene-9-(phenylsulfonyl)-1,2,3,4,5,9-hexahydro[1,5]oxazocino[3,2-e]indole. Microwave reactions were performed with a Personal Chemistry Smith Creator using 0.5-2 mL or 2-5 mL Smith Process Vials fitted with aluminum caps and septa.

TABLE I
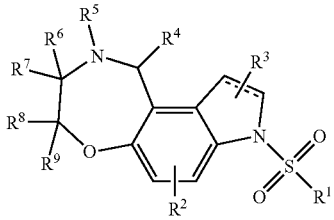
| Example | Chemical Name | Structure |
|---|---|---|
| 1 | 2,5-methylene-9-(phenylsulfonyl)-1,2,3,4,5,9-hexahydro[1,5]oxazocino[3,2-e]indole | 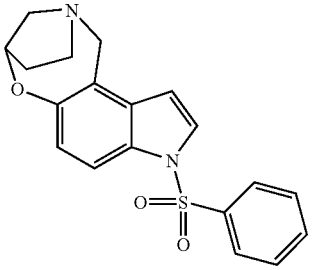 |
| 2 | 2,4-dimethyl-8-(phenylsulfonyl)-1,3,4,8-tetrahydro-2H-[1,4]oxazepino[6,7-e]indole trifluoroacetate | 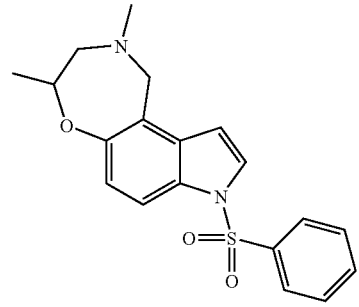 |
| 3 | 2-isopropyl-8-(phenylsulfonyl)-1,3,4,8-tetrahydro-2H-[1,4]oxazepino[6,7-e]indole trifluoroacetate | 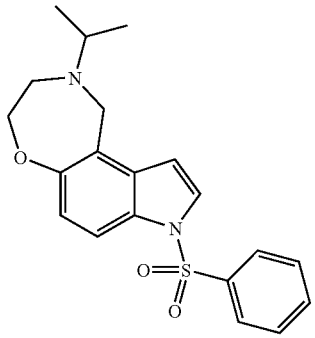 |
| 4 | 2-ethyl-8-(phenylsulfonyl)-1,3,4,8-tetrahydro-2H-[1,4]oxazepino[6,7-e]indole trifluoroacetate | 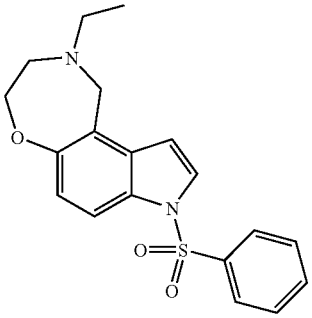 |

TABLE I-continued

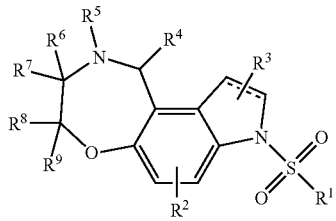

| Example | Chemical Name |
|---|---|
| 5 | 2-methyl-8-(phenylsulfonyl)-1,3,4,8-tetrahydro-2H-[1,4]oxazepino[6,7-e]indole trifluoroacetate |
| 6 | 8-(2,3-dihydro-1,4-benzodioxin-6-ylsulfonyl)-2-methyl-1,3,4,8-tetrahydro-2H-[1,4]oxazepino[6,7-e]indole |
| 7 | 8-[(3,4-dimethoxyphenyl)sulfonyl]-2-methyl-1,3,4,8-tetrahydro-2H-[1,4]oxazepino[6,7-e]indole |
| 8 | 8-(1-benzofuran-2-ylsulfonyl)-2-methyl-1,3,4,8-tetrahydro-2H-[1,4]oxazepino[6,7-e]indole |
| 9 | 8-[(2,5-dimethyl-3-furyl)sulfonyl]-2-methyl-1,3,4,8-tetrahydro-2H-[1,4]oxazepino[6,7-e]indole |

TABLE I-continued

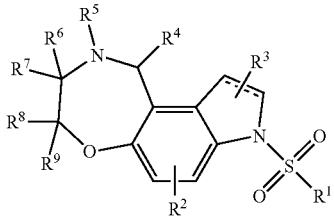

| Example | Chemical Name | Structure |
|---|---|---|
| 10 | 8-(1,3-benzothiazol-6-ylsulfonyl)-2-methyl-1,3,4,8-tetrahydro-2H-[1,4]oxazepino[6,7-e]indole | 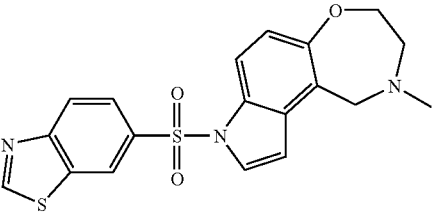 |
| 11 | 2-methyl-8-{[4-(methylsulfonyl)phenyl]sulfonyl}-1,3,4,8-tetrahydro-2H-[1,4]oxazepino[6,7-e]indole | 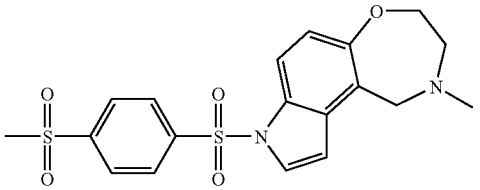 |
| 12 | 8-[(4-isopropylphenyl)sulfonyl]-2-methyl-1,3,4,8-tetrahydro-2H-[1,4]oxazepino[6,7-e]indole | 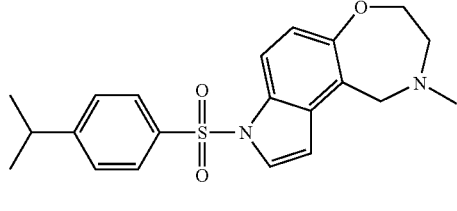 |
| 13 | 8-[(2,2-dimethyl-3,4-dihydro-2H-chromen-6-yl)sulfonyl]-2-methyl-1,3,4,8-tetrahydro-2H-[1,4]oxazepino[6,7-e]indole | 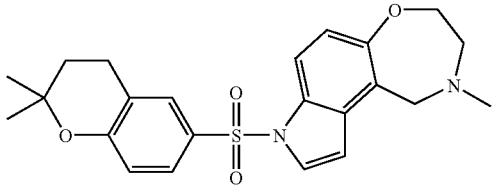 |
| 14 | 8-[(2-chloro-4-fluorophenyl)sulfonyl]-2-methyl-1,3,4,8-tetrahydro-2H-[1,4]oxazepino[6,7-e]indole | 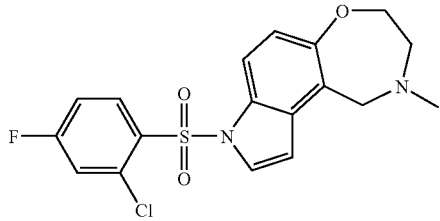 |
| 15 | 8-[(3,4-dichlorophenyl)sulfonyl]-2-methyl-1,3,4,8-tetrahydro-2H-[1,4]oxazepino[6,7-e]indole | 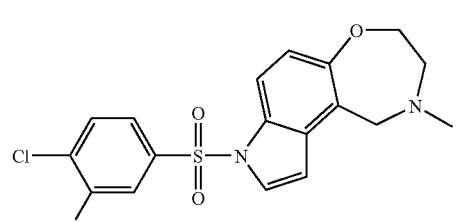 |

TABLE I-continued

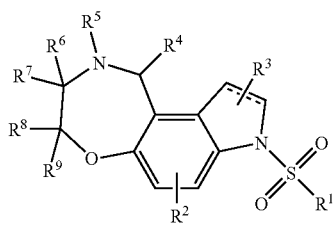

| Example | Chemical Name | Structure |
|---------|---------------|-----------|
| 16 | 8-[(4-fluorophenyl)sulfonyl]-2-methyl-1,3,4,8-tetrahydro-2H-[1,4]oxazepino[6,7-e]indole | 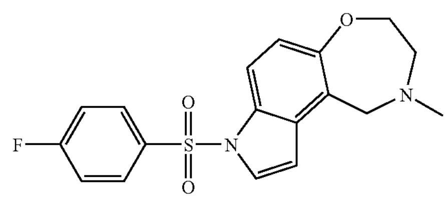 |
| 17 | 8-[(2,6-difluorophenyl)sulfonyl]-2-methyl-1,3,4,8-tetrahydro-2H-[1,4]oxazepino[6,7-e]indole | 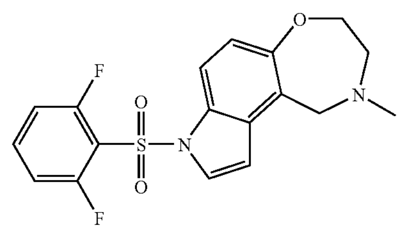 |
| 18 | 2-methyl-8-{[4-(trifluoromethoxy)phenyl]sulfonyl}-1,3,4,8-tetrahydro-2H-[1,4]oxazepino[6,7-e]indole | 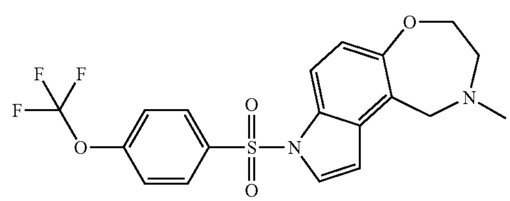 |
| 19 | 2-methyl-8-(2-naphthylsulfonyl)-1,3,4,8-tetrahydro-2H-[1,4]oxazepino[6,7-e]indole | 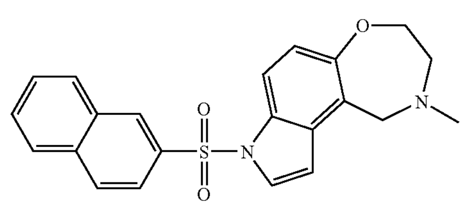 |
| 20 | 8-[(3-chloro-4-methylphenyl)sulfonyl]-2-methyl-1,3,4,8-tetrahydro-2H-[1,4]oxazepino[6,7-e]indole | 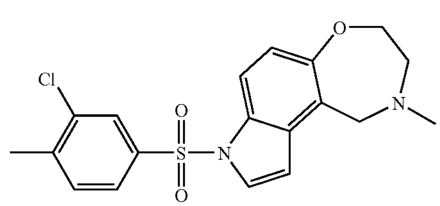 |
| 21 | 8-[(4,5-dichloro-2-thienyl)sulfonyl]-2-methyl-1,3,4,8-tetrahydro-2H-[1,4]oxazepino[6,7-e]indole | 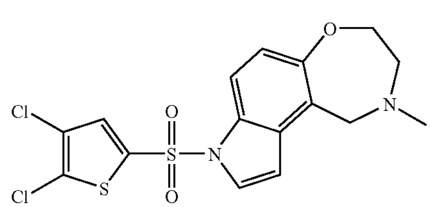 |

TABLE I-continued

| Example | Chemical Name | Structure |
|---------|---------------|-----------|
| 22 | 8-[(5-chloro-3-methyl-1-benzothien-2-yl)sulfonyl]-2-methyl-1,3,4,8-tetrahydro-2H-[1,4]oxazepino[6,7-e]indole | 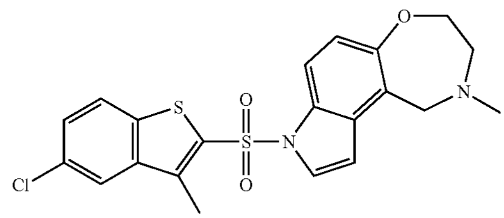 |
| 23 | 8-[2,4-dichlorophenyl)sulfonyl]-2-methyl-1,3,4,8-tetrahydro-2H-[1,4]oxazepino[6,7-e]indole | 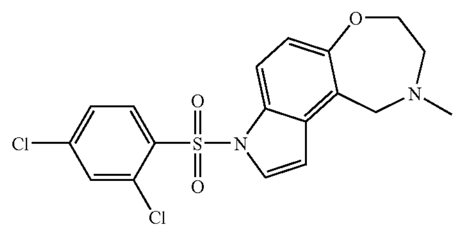 |
| 24 | 8-{[4-fluoro-3-(trifluoromethyl)phenyl]sulfonyl}-2-methyl-1,3,4,8-tetrahydro-2H-[1,4]oxazepino[6,7-e]indole | 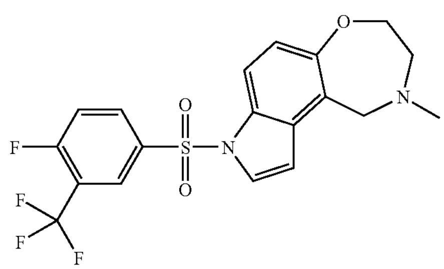 |
| 25 | 2-methyl-8-(2-thienylsulfonyl)-1,3,4,8-tetrahydro-2H-[1,4]oxazepino[6,7-e]indole | 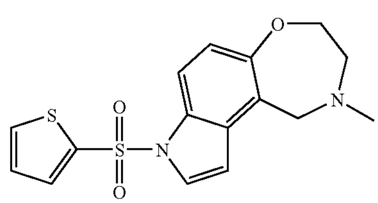 |
| 26 | 2-methyl-8-[(4-methylphenyl)sulfonyl]-1,3,4,8-tetrahydro-2H-[1,4]oxazepino[6,7-e]indole | 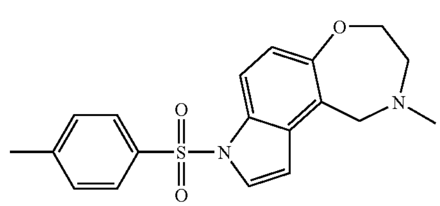 |

TABLE I-continued

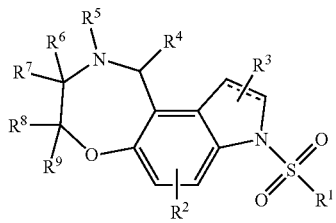

| Example | Chemical Name | Structure |
|---|---|---|
| 27 | 8-[(2-methoxy-5-methylphenyl)sulfonyl]-2-methyl-1,3,4,8-tetrahydro-2H-[1,4]oxazepino[6,7-e]indole | 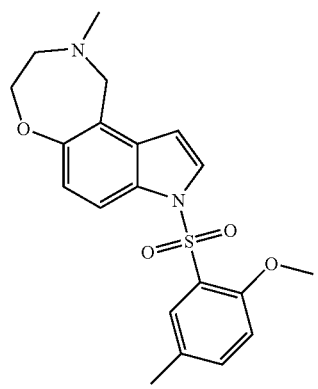 |
| 28 | 8-[(3-fluoro-4-methylphenyl)sulfonyl]-2-methyl-1,3,4,8-tetrahydro-2H-[1,4]oxazepino[6,7-e]indole | 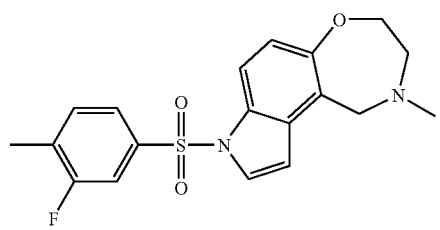 |
| 29 | 8-(1-benzothien-3-ylsulfonyl)-2-methyl-1,3,4,8-tetrahydro-2H-[1,4]oxazepino[6,7-e]indole | 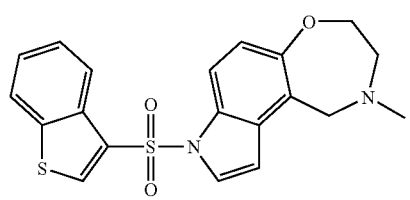 |
| 30 | 8-[(4-methoxyphenyl)sulfonyl]-2-methyl-1,3,4,8-tetrahydro-2H-[1,4]oxazepino[6,7-e]indole | 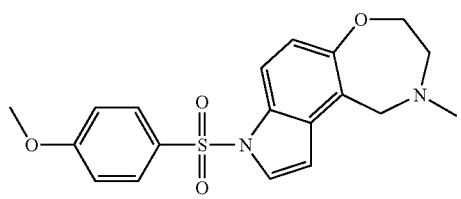 |
| 31 | 2-methyl-8-{[4-(trifluoromethyl)phenyl]sulfonyl}-1,3,4,8-tetrahydro-2H-[1,4]oxazepino[6,7-e]indole | 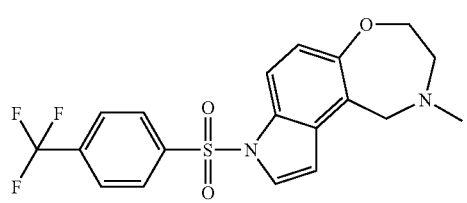 |

TABLE I-continued

| Example | Chemical Name | Structure |
|---|---|---|
| 32 | 2-methyl-8-[(4-propylphenyl)sulfonyl]-1,3,4,8-tetrahydro-2H-[1,4]oxazepino[6,7-e]indole | 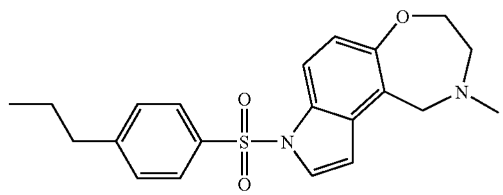 |
| 33 | 3-chloro-4-[(2-methyl-1,2,3,4-tetrahydro-8H-[1,4]oxazepino[6,7-e]indol-8-yl)sulfonyl]benzonitrile | 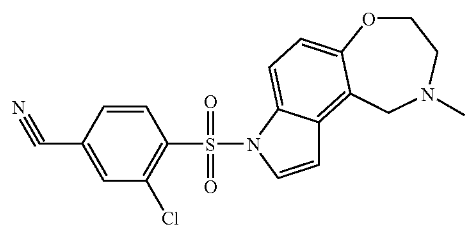 |
| 34 | 8-[(2,5-dimethyl-3-thienyl)sulfonyl]-2-methyl-1,3,4,8-tetrahydro-2H-[1,4]oxazepino[6,7-e]indole | 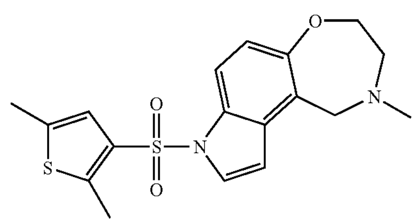 |
| 35 | 2-[(2-methyl-1,2,3,4-tetrahydro-8H-[1,4]oxazepino[6,7-e]indol-8-yl)sulfonyl]benzonitrile | 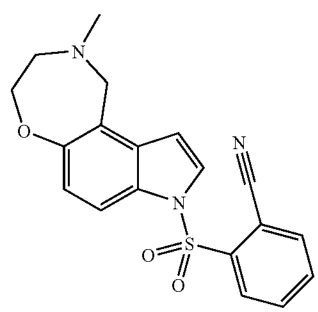 |
| 36 | 2-methyl-1-[2-methyl-8-(phenylsulfonyl)-1,3,4,8-tetrahydro-2H-[1,4]oxazepino[6,7-e]indol-9-yl]propan-1-one trifluoroacetate | 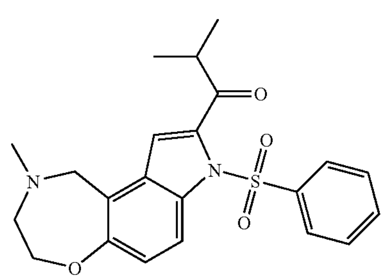 |

TABLE I-continued

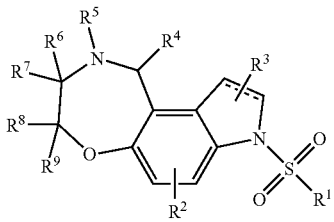

| Example | Chemical Name | Structure |
|---|---|---|
| 37 | 1-[2-methyl-8-(phenylsulfonyl)-1,3,4,8-tetrahydro-2H-[1,4]oxazepino[6,7-e]indol-9-yl]ethanone trifluoroacetate | 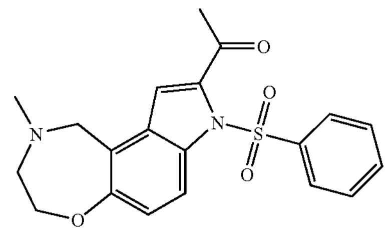 |
| 38 | 9-chloro-2-methyl-8-(phenylsulfonyl)-1,3,4,8-tetrahydro-2H-[1,4]oxazepino[6,7-e]indole trifluoroacetate | 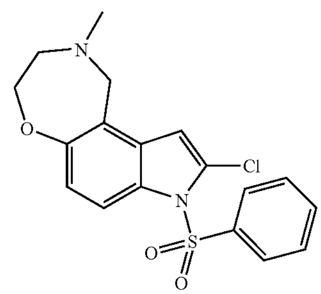 |
| 39 | 2-[2-methyl-8-(phenylsulfonyl)-1,3,4,8-tetrahydro-2H-[1,4]oxazepino[6,7-e]indol-9-yl]propan-2-ol trifluoroacetate (salt) | 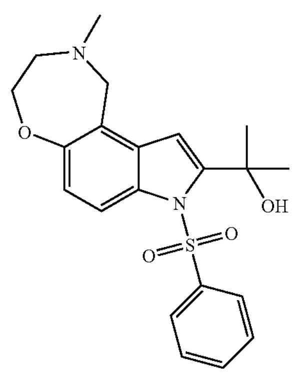 |
| 40 | cyclopropyl[2-methyl-8-(phenylsulfonyl)-1,3,4,8-tetrahydro-2H-[1,4]oxazepino[6,7-e]indol-9-yl]methanol | 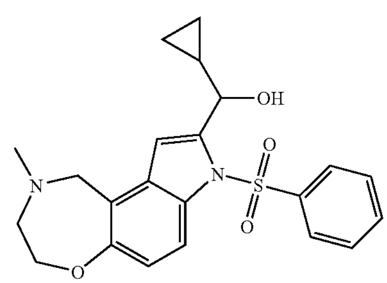 |

TABLE I-continued

| Example | Chemical Name | Structure |
|---|---|---|
| 41 | 1-[2-methyl-8-(phenylsulfonyl)-1,3,4,8-tetrahydro-2H-[1,4]oxazepino[6,7-e]indol-9-yl]ethanol trifluoroacetate (salt) | 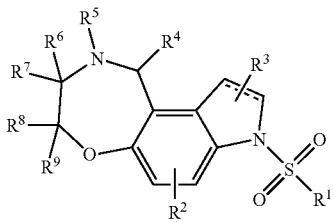 |
| 42 | 10-chloro-2-methyl-8-(phenylsulfonyl)-1,3,4,8-tetrahydro-2H-[1,4]oxazepino[6,7-e]indole | 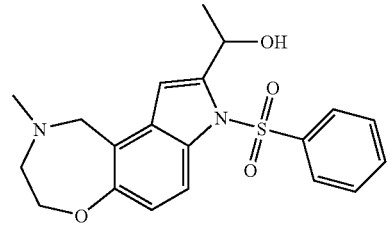 |
| 43 | (7aR)-3-(phenylsulfonyl)-3,7a,8,9,10,12-hexahydro-7H-pyrrolo[2',1':3,4][1,4]oxazepino[6,7-e]indole trifluoroacetate | 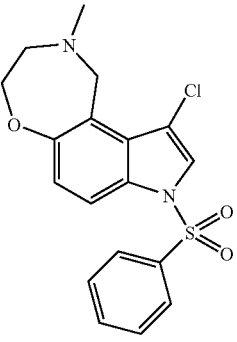 |
| 44 | (7aS)-3-(phenylsulfonyl)-3,7a,8,9,10,12-hexahydro-7H-pyrrolo[2',1':3,4][1,4]oxazepino[6,7-e]indole trifluoroacetate | 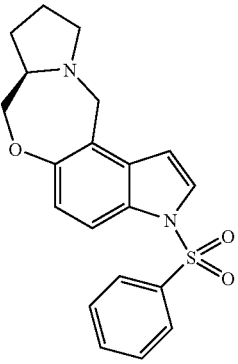 |

TABLE I-continued

| Example | Chemical Name | Structure |
|---|---|---|
| 45 | (3S)-3-methyl-8-(phenylsulfonyl)-1,3,4,8-tetrahydro-2H-[1,4]oxazepino[6,7-e]indole | 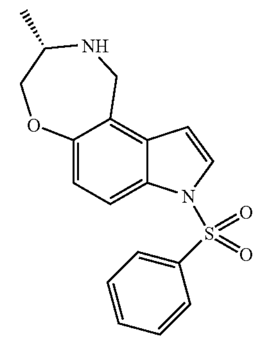 |
| 46 | (3S)-2,3-dimethyl-8-(phenylsulfonyl)-1,3,4,8-tetrahydro-2H-[1,4]oxazepino[6,7-e]indole trifluoroacetate | 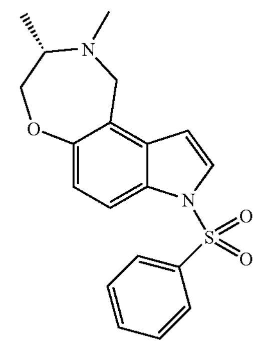 |
| 47 | 2,7-dimethyl-8-(phenylsulfonyl)-1,3,4,8-tetrahydro-2H-[1,4]oxazepino[6,7-e]indole trifluoroacetate | 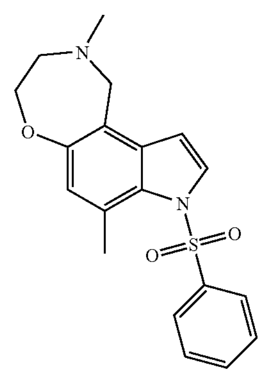 |
| 48 | 6-methoxy-2-methyl-8-(phenylsulfonyl)-1,3,4,8-tetrahydro-2H-[1,4]oxazepino[6,7-e]indole | 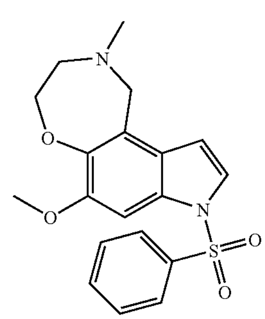 |

TABLE I-continued
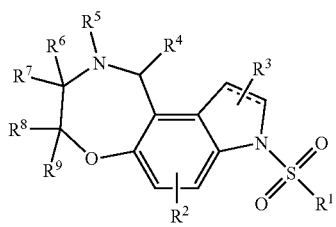
| Example | Chemical Name | Structure |
|---|---|---|
| 49 | 8-(phenylsulfonyl)-1,3,4,8-tetrahydro-2H-[1,4]oxazepino[6,7-e]indole | 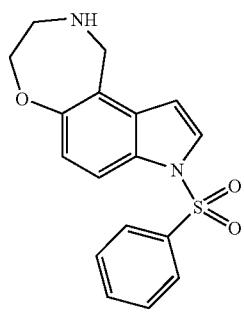 |
| 50 | 2-(2-fluoroethyl)-8-(phenylsulfonyl)-1,3,4,8-tetrahydro-2H-[1,4]oxazepino[6,7-e]indole | 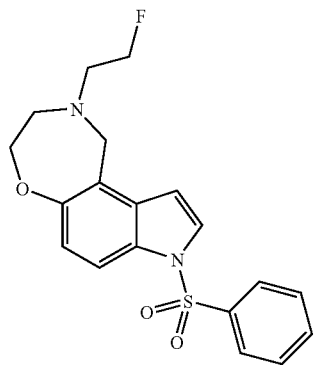 |
| 51 | 8-[(2-methoxy-5-methylphenyl)sulfonyl]-1,3,4,8-tetrahydro-2H-[1,4]oxazepino[6,7-e]indole | 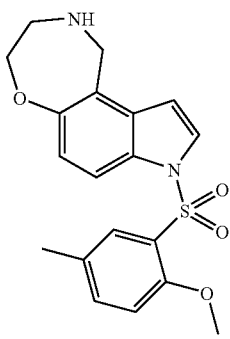 |
| 52 | 8-[(2,4-dichlorophenyl)sulfonyl]-1,3,4,8-tetrahydro-2H-[1,4]oxazepino[6,7-e]indole | 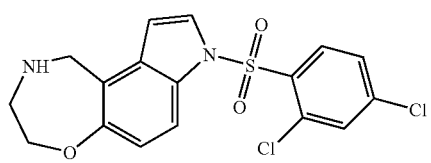 |

TABLE I-continued

| Example | Chemical Name | Structure |
|---|---|---|
| 53 | 8-{[3-trifluoromethyl)phenyl]sulfonyl}-1,3,4,8-tetrahydro-2H-[1,4]oxazepino[6,7-e]indole | 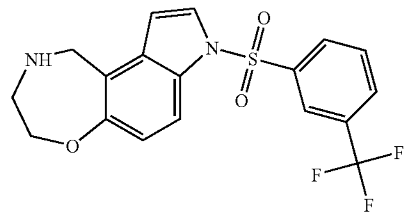 |
| 54 | 8-[(3,4-dimethoxyphenyl)sulfonyl]-1,3,4,8-tetrahydro-2H-[1,4]oxazepino[6,7-e]indole | 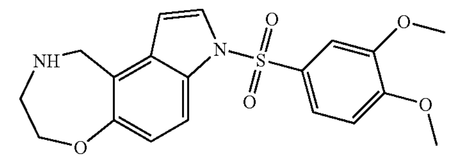 |
| 55 | 8-(2-naphthylsulfonyl)-1,3,4,8-tetrahydro-2H-[1,4]oxazepino[6,7-e]indole | 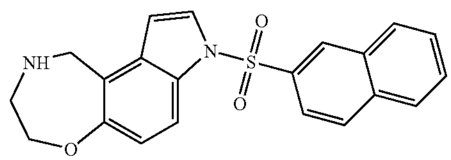 |
| 56 | 8-[(2-methoxy-4-methylphenyl)sulfonyl]-1,3,4,8-tetrahydro-2H-[1,4]oxazepino[6,7-e]indole | 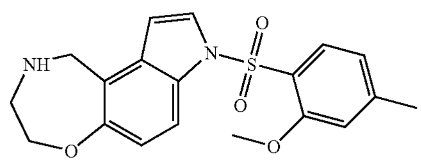 |
| 57 | 8-[(4-propylphenyl)sulfonyl]-1,3,4,8-tetrahydro-2H-[1,4]oxazepino[6,7-e]indole | 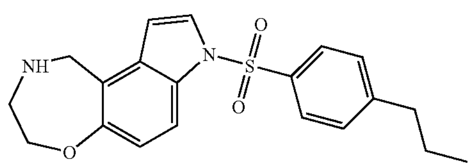 |
| 58 | 8-[(4-isopropylphenyl)sulfonyl]-1,3,4,8-tetrahydro-2H-[1,4]oxazepino[6,7-e]indole | 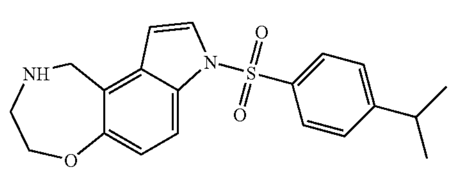 |
| 59 | 8-(1-benzofuran-2-ylsulfonyl)-1,3,4,8-tetrahydro-2H-[1,4]oxazepino[6,7-e]indole | 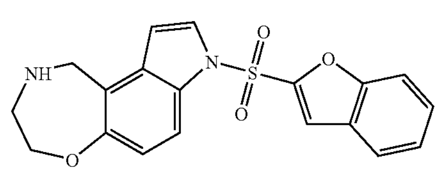 |

TABLE I-continued

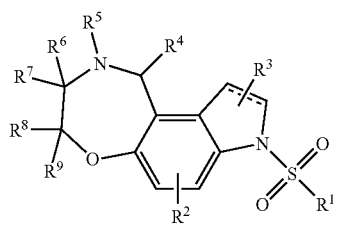

| Example | Chemical Name | Structure |
|---|---|---|
| 60 | 8-[(2,5-dimethyl-3-thienyl)sulfonyl]-1,3,4,8-tetrahydro-2H-[1,4]oxazepino[6,7-e]indole | 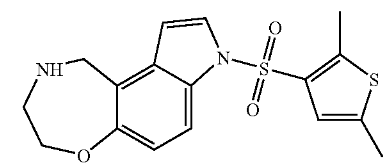 |
| 61 | 8-[(3-fluoro-4-methylphenyl)sulfonyl]-1,3,4,8-tetrahydro-2H-[1,4]oxazepino[6,7-e]indole | 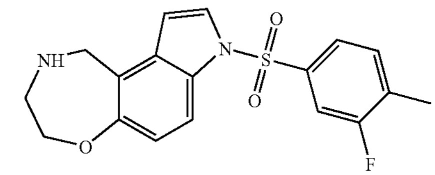 |
| 62 | 8-[(4-methoxyphenyl)sulfonyl]-1,3,4,8-tetrahydro-2H-[1,4]oxazepino[6,7-e]indole | 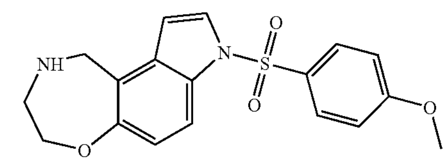 |
| 63 | 8-[(2,5-dimethyl-3-furyl)sulfonyl]-1,3,4,8-tetrahydro-2H-[1,4]oxazepino[6,7-e]indole | 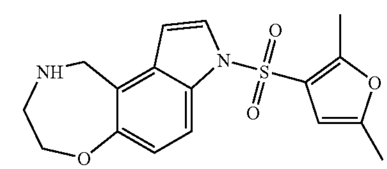 |
| 64 | 8-[(2-methylphenyl)sulfonyl]-1,3,4,8-tetrahydro-2H-[1,4]oxazepino[6,7-e]indole | 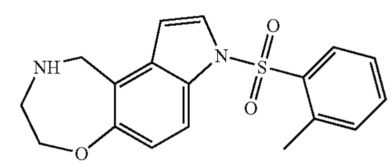 |
| 65 | 8-[(4-methylphenyl)sulfonyl]-1,3,4,8-tetrahydro-2H-[1,4]oxazepino[6,7-e]indole | 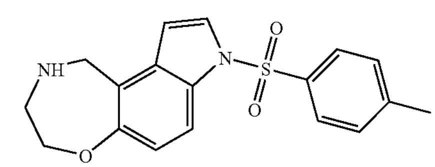 |
| 66 | 8-(2-thienylsulfonyl)-1,3,4,8-tetrahydro-2H-[1,4]oxazepino[6,7-e]indole | 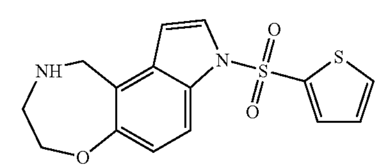 |

TABLE I-continued

| Example | Chemical Name | Structure |
|---|---|---|
| 67 | 8-{[2-(trifluoromethoxy)phenyl]sulfonyl}-1,3,4,8-tetrahydro-2H-[1,4]oxazepino[6,7-e]indole | 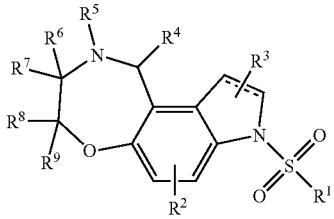 |
| 68 | 8-(biphenyl-3-ylsulfonyl)-1,3,4,8-tetrahydro-2H-[1,4]oxazepino[6,7-e]indole | 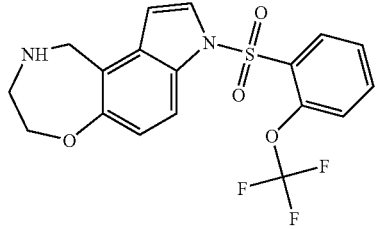 |
| 69 | 8-{[2-(trifluoromethyl)phenyl]sulfonyl}-1,3,4,8-tetrahydro-2H-[1,4]oxazepino[6,7-e]indole | 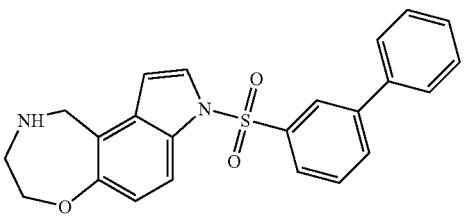 |
| 70 | 8-(1-benzothien-2-ylsulfonyl)-1,3,4,8-tetrahydro-2H-[1,4]oxazepino[6,7-e]indole | 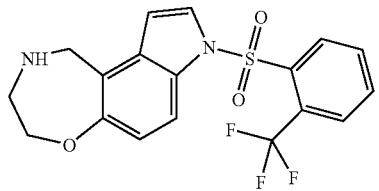 |
| 71 | 8-(1-naphthylsulfonyl)-1,3,4,8-tetrahydro-2H-[1,4]oxazepino[6,7-e]indole | 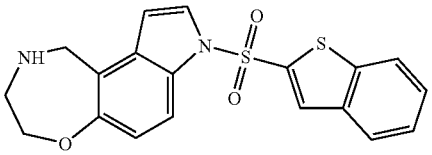 |
| 72 | 8-[(5-fluoro-2-methylphenyl)sulfonyl]-1,3,4,8-tetrahydro-2H-[1,4]oxazepino[6,7-e]indole | 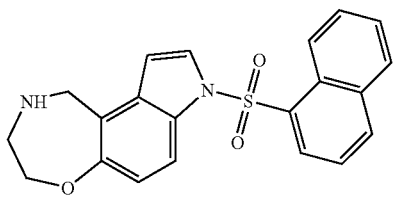 |

TABLE I-continued
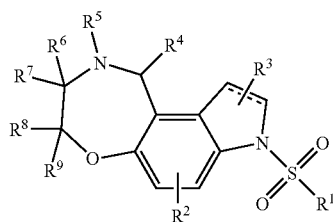
| Example | Chemical Name | Structure |
|---|---|---|
| 73 | (3R)-3-methyl-8-(phenylsulfonyl)-1,3,4,8-tetrahydro-2H-[1,4]oxazepino[6,7-e]indole | 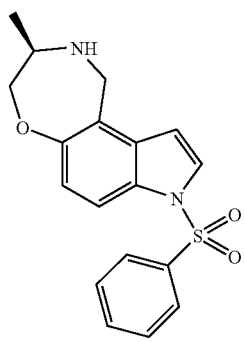 |
| 74 | (3R)-2,3-dimethyl-8-(phenylsulfonyl)-1,3,4,8-tetrahydro-2H-[1,4]oxazepino[6,7-e]indole | 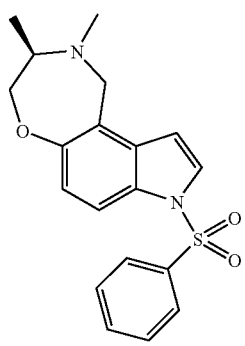 |
| 75 | 6-methoxy-8-(phenylsulfonyl)-1,3,4,8-tetrahydro-2H-[1,4]oxazepino[6,7-e]indole | 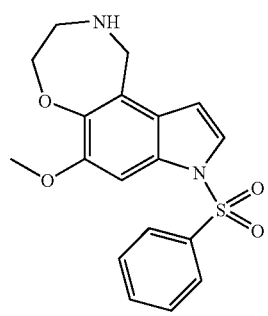 |
| 76 | 9-methyl-8-(phenylsulfonyl)-1,3,4,8-tetrahydro-2H-[1,4]oxazepino[6,7-e]indole trifluoroacetate | 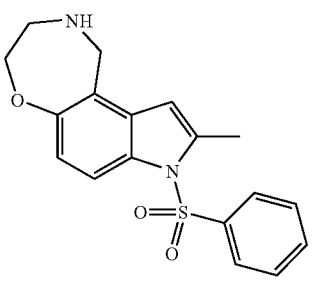 |

TABLE I-continued

| Example | Chemical Name | Structure |
|---|---|---|
| 77 | 10-chloro-8-(phenylsulfonyl)-1,3,4,8-tetrahydro-2H-[1,4]oxazepino[6,7-e]indole trifluoroacetate | 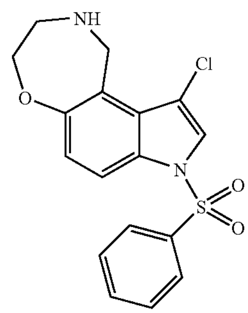 |
| 78 | 10-chloro-8-[(4-fluorophenyl)sulfonyl]-1,3,4,8-tetrahydro-2H-[1,4]oxazepino[6,7-e]indole trifluoroacetate | 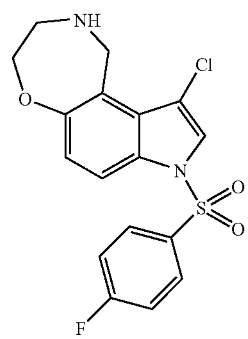 |
| 79 | 3-[(10-chloro-1,2,3,4-tetrahydro-8H-[1,4]oxazepino[6,7-e]indol-8-yl)sulfonyl]benzonitrile trifluoroacetate | 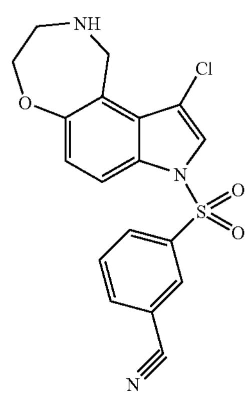 |
| 80 | 10-chloro-8-(pyridin-3-ylsulfonyl)-1,3,4,8-tetrahydro-2H-[1,4]oxazepino[6,7-e]indole bis(trifluoroacetate) | 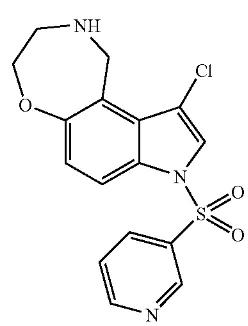 |

TABLE I-continued
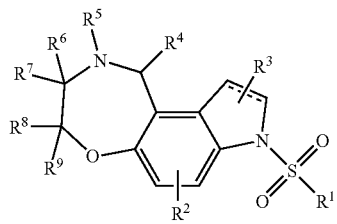
| Example | Chemical Name | Structure |
|---|---|---|
| 81 | 8-[(2-chlorophenyl)sulfonyl]-1,3,4,8-tetrahydro-2H-[1,4]oxazepino[6,7-e]indole trifluoroacetate | 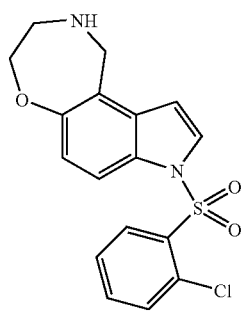 |
| 82 | 1-methyl-8-(phenylsulfonyl)-1,3,4,8-tetrahydro-2H-[1,4]oxazepino[6,7-e]indole | 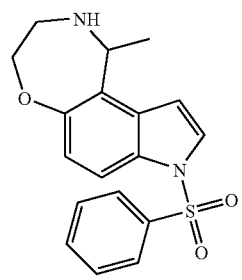 |
| 83 | (1S)-1-methyl-8-(phenylsulfonyl)-1,3,4,8-tetrahydro-2H-[1,4]oxazepino[6,7-e]indole | 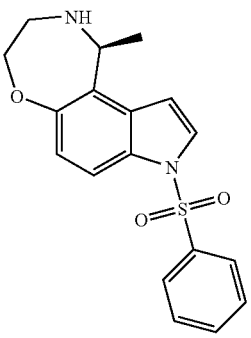 |
| 84 | (1R)-1-methyl-8-(phenylsulfonyl)-1,3,4,8-tetrahydro-2H-[1,4]oxazepino[6,7-e]indole | 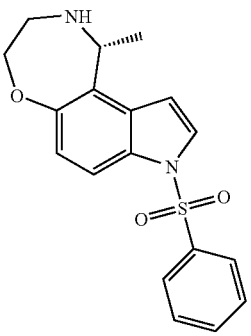 |

TABLE I-continued
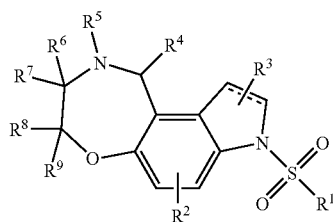
| Example | Chemical Name | Structure |
|---|---|---|
| 85 | 1-methyl-8-(phenylsulfonyl)-3,8-dihydro-4H-[1,4]oxazepino[6,7-e]indole | 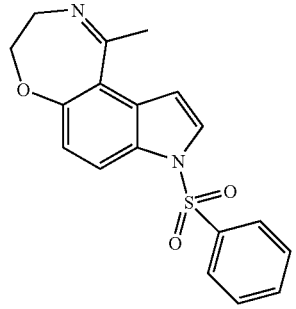 |
| 86 | 6-fluoro-1-methyl-8-(phenylsulfonyl)-1,3,4,8-tetrahydro-2H-[1,4]oxazepino[6,7-e]indole | 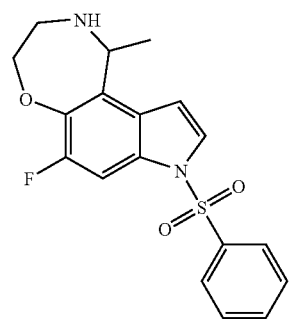 |
| 87 | 6-methoxy-1-methyl-8-(phenylsulfonyl)-1,3,4,8-tetrahydro-2H-[1,4]oxazepino[6,7-e]indole | 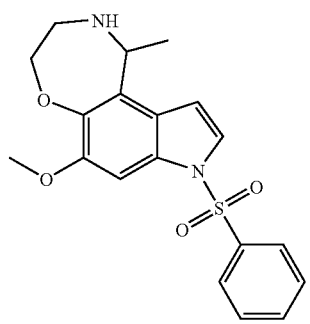 |
| 88 | 8-[(2-chlorophenyl)sulfonyl]-6-methoxy-1-methyl-1,3,4,8-tetrahydro-2H-[1,4]oxazepino[6,7-e]indole trifluoroacetate | 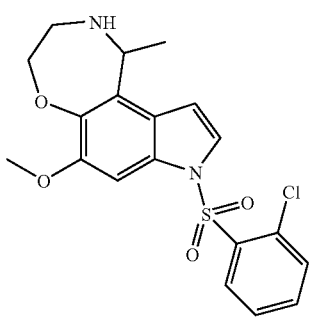 |

TABLE I-continued

| Example | Chemical Name | Structure |
|---------|---------------|-----------|
| 89 | 6-methoxy-1-methyl-8-[(2-methylphenyl)sulfonyl]-1,3,4,8-tetrahydro-2H-[1,4]oxazepino[6,7-e]indole trifluoroacetate | 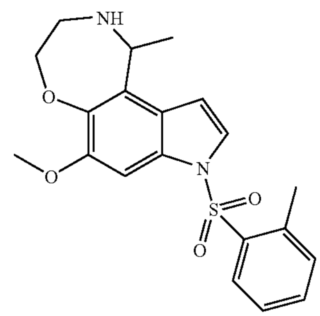 |
| 90 | 8-[(2,6-difluorophenyl)sulfonyl]-6-methoxy-1-methyl-1,3,4,8-tetrahydro-2H-[1,4]oxazepino[6,7-e]indole trifluoroacetate | 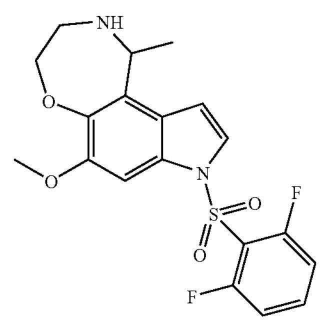 |
| 91 | 6-methoxy-8-[(2-methoxy-5-methylphenyl)sulfonyl]-1-methyl-1,3,4,8-tetrahydro-2H-[1,4]oxazepino[6,7-e]indole trifluoroacetate | 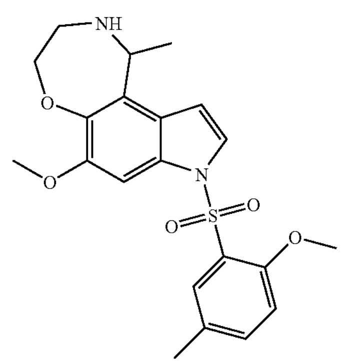 |
| 92 | 8-[(2,4-dichlorophenyl)sulfonyl]-6-methoxy-1-methyl-1,3,4,8-tetrahydro-2H-[1,4]oxazepino[6,7-e]indole trifluoroacetate | 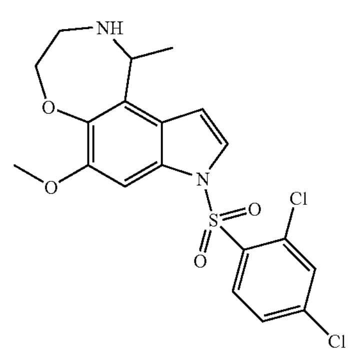 |

TABLE I-continued
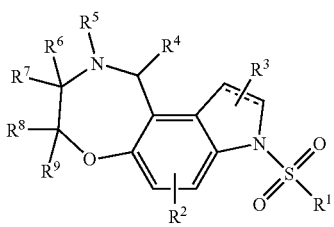
| Example | Chemical Name | Structure |
|---|---|---|
| 93 | 1-isopropyl-8-(phenylsulfonyl)-1,3,4,8-tetrahydro-2H-[1,4]oxazepino[6,7-e]indole | 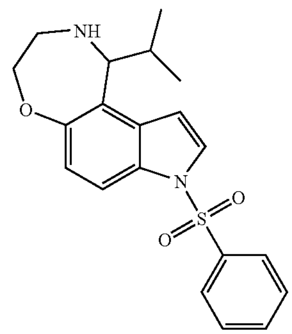 |
| 94 | 1-isopropyl-2-methyl-8-(phenylsulfonyl)-1,3,4,8-tetrahydro-2H-[1,4]oxazepino[6,7-e]indole | 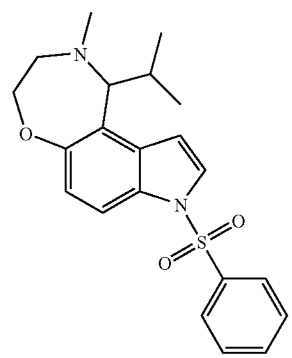 |
| 95 | 1,2-dimethyl-8-(phenylsulfonyl)-1,3,4,8-tetrahydro-2H-[1,4]oxazepino[6,7-e]indole trifluoroacetate | 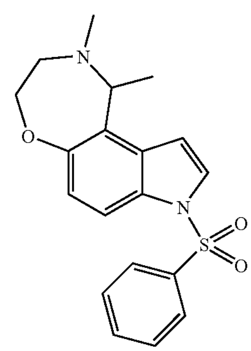 |
| 96 | 10-chloro-1-methyl-8-(phenylsulfonyl)-3,8-dihydro-4H-[1,4]oxazepino[6,7-e]indole | 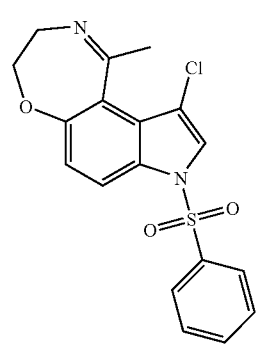 |

TABLE I-continued

| Example | Chemical Name | Structure |
|---------|---------------|-----------|
| 97 | 10-chloro-1-methyl-8-(pyridin-3-ylsulfonyl)-1,3,4,8-tetrahydro-2H-[1,4]oxazepino[6,7-e]indole bis(trifluoroacetate) | 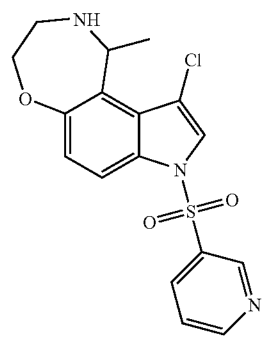 |
| 98 | 10-chloro-1-methyl-8-(phenylsulfonyl)-1,3,4,8-tetrahydro-2H-[1,4]oxazepino[6,7-e]indole trifluoroacetate | 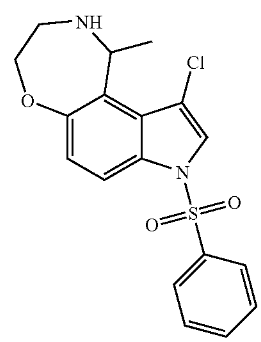 |
| 99 | 10-chloro-1,2-dimethyl-8-(phenylsulfonyl)-1,3,4,8-tetrahydro-2H-[1,4]oxazepino[6,7-e]indole | 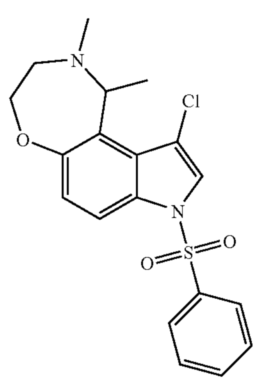 |

TABLE I-continued

| Example | Chemical Name | Structure |
|---------|---------------|-----------|
| 100 | 10-chloro-8-[(2-methoxy-5-methylphenyl)sulfonyl]-1-methyl-1,3,4,8-tetrahydro-2H-[1,4]oxazepino[6,7-e]indole | 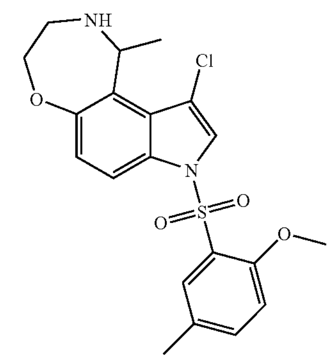 |
| 101 | 10-chloro-8-[(2-methoxy-5-methylphenyl)sulfonyl]-1,2-dimethyl-1,3,4,8-tetrahydro-2H-[1,4]oxazepino[6,7-e]indole trifluoroacetate | 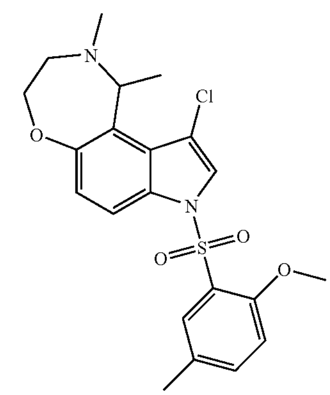 |
| 102 | 10-chloro-8-[(2-fluorophenyl)sulfonyl]-1-methyl-1,3,4,8-tetrahydro-2H-[1,4]oxazepino[6,7-e]indole trifluoroacetate | 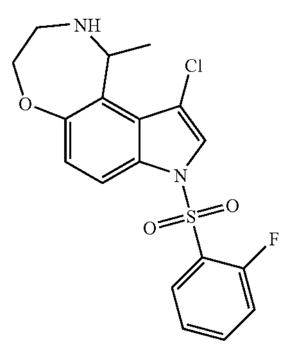 |

TABLE I-continued

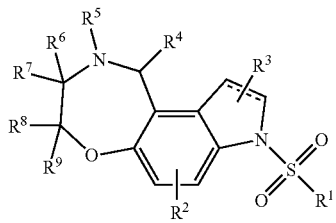

| Example | Chemical Name | Structure |
|---|---|---|
| 103 | 10-chloro-8-[(2-fluorophenyl)sulfonyl]-1,2-dimethyl-1,3,4,8-tetrahydro-2H-[1,4]oxazepino[6,7-e]indole trifluoroacetate | 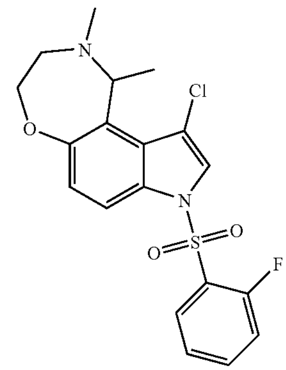 |
| 104 | 10-chloro-8-[(3-fluorophenyl)sulfonyl]-1-methyl-1,3,4,8-tetrahydro-2H-[1,4]oxazepino[6,7-e]indole trifluoroacetate | 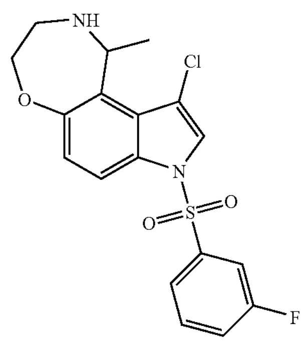 |
| 105 | 10-chloro-8-[(3-fluorophenyl)sulfonyl]-1,2-dimethyl-1,3,4,8-tetrahydro-2H-[1,4]oxazepino[6,7-e]indole trifluoroacetate | 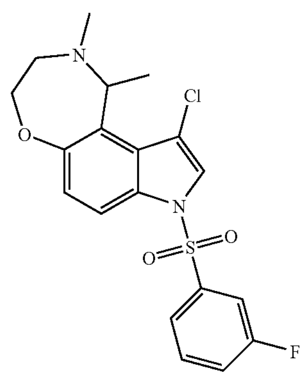 |
| 106 | 1-methyl-8-(pyridin-3-ylsulfonyl)-1,3,4,8-tetrahydro-2H-[1,4]oxazepino[6,7-e]indole bis(trifluoroacetate) | 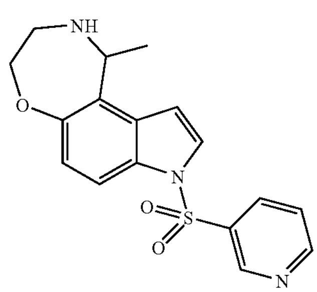 |

TABLE I-continued

| Example | Chemical Name | Structure |
|---------|---------------|-----------|
| 107 | 8-[(2-chlorophenyl)sulfonyl]-1-methyl-1,3,4,8-tetrahydro-2H-[1,4]oxazepino[6,7-e]indole | 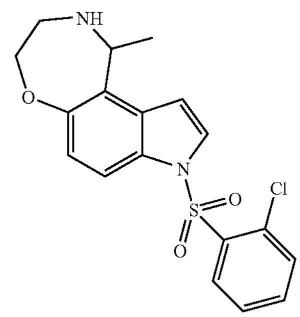 |
| 108 | 1-methyl-8-[(2-methylphenyl)sulfonyl]-1,3,4,8-tetrahydro-2H-[1,4]oxazepino[6,7-e]indole | 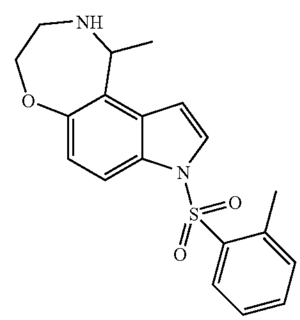 |
| 109 | 8-[(2,6-difluorophenyl)sulfonyl]-1-methyl-1,3,4,8-tetrahydro-2H-[1,4]oxazepino[6,7-e]indole | 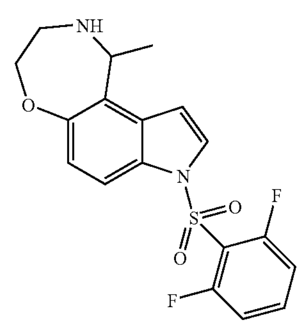 |
| 110 | 8-[(2,4-dichlorophenyl)sulfonyl]-1-methyl-1,3,4,8-tetrahydro-2H-[1,4]oxazepino[6,7-e]indole | 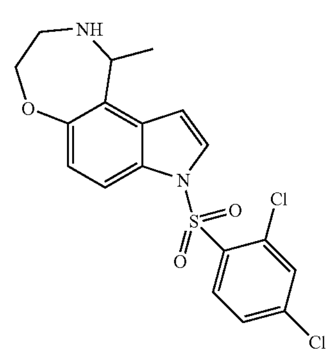 |

TABLE I-continued
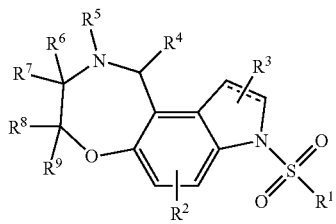
| Example | Chemical Name | Structure |
|---|---|---|
| 111 | 8-[(2-methoxy-5-methylphenyl)sulfonyl]-1-methyl-1,3,4,8-tetrahydro-2H-[1,4]oxazepino[6,7-e]indole | 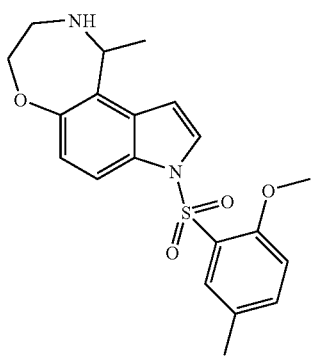 |
| 112 | 8-[(2-methoxy-4-methylphenyl)sulfonyl]-1-methyl-1,3,4,8-tetrahydro-2H-[1,4]oxazepino[6,7-e]indole | 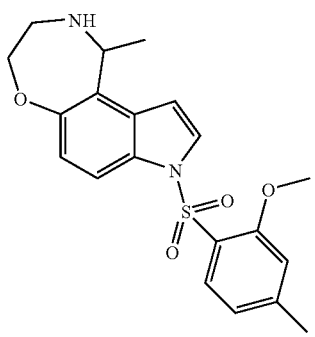 |
| 113 | 8-[(2,5-dimethyl-3-thienyl)sulfonyl]-1-methyl-1,3,4,8-tetrahydro-2H-[1,4]oxazepino[6,7-e]indole | 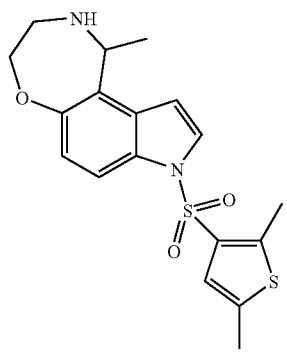 |

TABLE I-continued

| Example | Chemical Name | Structure |
|---|---|---|
| 114 | 8-[(2,5-dimethyl-3-furyl)sulfonyl]-1-methyl-1,3,4,8-tetrahydro-2H-[1,4]oxazepino[6,7-e]indole | 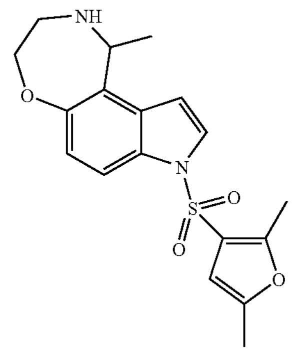 |
| 115 | 1-methyl-8-(2-thienylsulfonyl)-1,3,4,8-tetrahydro-2H-[1,4]oxazepino[6,7-e]indole | 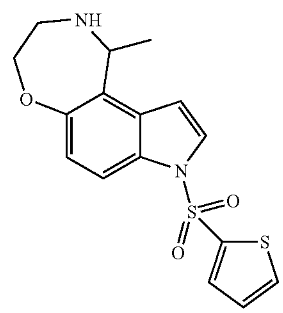 |
| 116 | 1-methyl-8-[(5-methylisoxazol-4-yl)sulfonyl]-1,3,4,8-tetrahydro-2H-[1,4]oxazepino[6,7-e]indole | 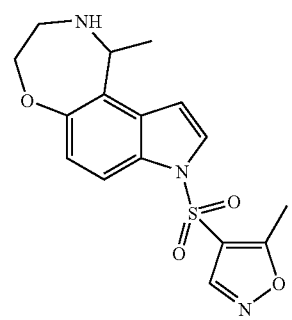 |
| 117 | 8-[(1,2-dimethyl-1H-imidazol-4-yl)sulfonyl]-1-methyl-1,3,4,8-tetrahydro-2H-[1,4]oxazepino[6,7-e]indole | 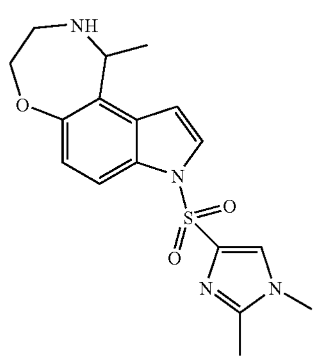 |

Intermediate 1

2-Bromo-3-methyl-4-nitro-phenol

A 2:1 mixture of 2-bromo-3-methyl-4-nitro-phenol and 2-Bromo-5-methyl-4-nitro-phenol was prepared as described in the literature by bromination of 3-methyl-4-nitrophenol (Muntwyler, R., Widmer, J., Keller-Schierlein, W. Synthese des 5-Chlor-6-methyl-salicylsäure-methyläthers, eines Abbauproduktes des Chlorothricins. *Helv Chim Acta* 1970, 53, 1544-1547).

Intermediate 2

5-(Benzyloxy)-4-bromo-1H-indole

To a suspension of grinded $K_2CO_3$ (11.4 g, 83.0 mmol) in dry acetone (150 mL) was added the regiomixture of the bromophenols, (Intermediate 1, 12.4 g, 53.5 mmol) and BnBr (9.42 g, 55.1 mmol) and the mixture was heated at reflux for two hours. The reaction mixture was filtered and the filtrate was evaporated under reduced pressure to give an oil that was used without further purification in the next step. The crude benzyl ether was dissolved in dry DMF (100 mL) and dimethylformamide dimethylacetal (13.0 g, 109 mmol) was added and the reaction was heated at 90° C. for two days. Each day the next three days, a portion of dimethylformamide dimethylacetal (1.0 g, 8.0 mmol) was added at 90° C. The solvent was removed under reduced pressure and the black/red oily residue was dissolved in acetic acid (20 mL). The viscous solution was carefully added to a well stirred suspension of iron powder (9.15 g, 164 mmol) in warm acetic acid (60 mL) during a period of 10 minutes. The thick reaction mixture was heated at reflux for one hour, the solids were filtered, and the filtrate was evaporated under reduced pressure. The black residue was dissolved in warm $CHCl_3$ (350 mL), 50 g of silica gel was added followed by heptane (350 mL). The mixture was filtered through a pad of silica gel and the solvent was evaporated. The black residue was purified by flash chromatography on silica gel using petroleum ether/EtOAc 90:10 as eluent to give the title compound (4.0 g) as a dark green oil. MS m/z 302/304 $[M+H]^+$.

Intermediate 3

4-Bromo-5-(benzyloxy)-1-(phenylsulfonyl)-1H-indole

To a solution of 4-bromo-5-benzyloxy-1H-indole (Intermediate 2, 3.85 g, 12.7 mmol) in DCM (30 mL) was added benzenesulfonyl chloride (2.47 g, 14.0 mmol), tetrabutylammonium hydrogensulphate (0.41 g, 1.3 mmol) and 3 M NaOH (13 mL, 39 mmol) and the mixture was stirred vigorously at room temperature for 30 minutes. The organic phase was washed with water and brine, dried ($MgSO_4$) and concentrated to dryness to give the title compound (5.7 g) as a solid. MS m/z 442/444 $[M+H]^+$.

Intermediate 4

5-(Benzyloxy)-1-(phenylsulfonyl)-1H-indole-4-carbaldehyde

To a warm solution of 4-bromo-5-benzyloxy-1-(phenylsulfonyl)-1H-indole (Intermediate 3, 4.74 g, 10.7 mmol) in toluene (100 mL) was added tributylvinyltin (6.80 g, 21.4 mmol) and $Pd(PPh_3)_2Cl_2$ (0.37 g, 0.50 mmol). The solution was heated at reflux for two hours and more $Pd(PPh_3)_2Cl_2$ (0.20 g, 0.30 mmol) was added and the reaction mixture was refluxed overnight. A teaspoon of silica gel was added and the mixture was filtered through a pad of silica gel. The solvent was removed under reduced pressure and the resulting oil was triturated with petroleum ether to give a semicrystalline mass (3.6 g) that was dissolved in dioxane (110 mL) and 2,6-lutidine (2.00 g, 18.7 mmol) and $OsO_4$ (0.24 g, 0.94 mmol) were added. The mixture was stirred at room temperature for five minutes. To the dark solution was added a solution of sodium periodate (8.02 g, 37.5 mmol) in water (35 mL) and the resulting suspension was stirred for 30 minutes. More dioxane (40 mL) was added and the mixture was filtered. The filtrate was evaporated to give a dark red oil. The crude product was purified by flash chromatography on silica gel using petroleum ether/EtOAc 90:10 followed by 80:20 as eluent to give the title compound (2.44 g) as a yellow solid. MS m/z 392 $[M+H]^+$.

Example 1

2,5-Methylene-9-(phenylsulfonyl)-1,2,3,4,5,9-hexahydro[1,5]oxazocino[3,2-e]indole To a solution of 5-(benzyloxy)-1-(phenylsulfonyl)-1H-indole-4-carbaldehyde (Intermediate 4, 100 mg, 0.250 mmol) in DCE (3 mL) was added 3-hydroxypyrrolidine, (33 mg, 0.38 mmol) and sodium triacetoxyborohydride (0.16 g, 0.77 mmol) and the mixture was stirred at room temperature overnight. The solvent was removed under reduced pressure and the residue was dissolved in MeOH (2 mL) and Pd/C 10 wt. % (0.020 g, 0.019 mmol) was added and the mixture was flushed with $N_2$ gas. Ammonium formate (0.050 g, 0.80 mmol) was added and the reaction mixture was stirred at room temperature overnight. The solvent was removed under reduced pressure and the residue was taken up in $CHCl_3/H_2O$, and the mixture was washed with water and brine, dried ($MgSO_4$) and the solvent was removed under reduced pressure to give 4-[(3-hydroxypyrrolidin-1-yl)methyl]-1-(phenylsulfonyl)-1H-indol-5-ol (85 mg) as an oil. MS m/z 373 $[M+H]^+$.

This oil (85 mg, 0.23 mmol) was dissolved in dry DCM (3 mL) and triphenylphosphine (179 mg, 0.680 mmol) was added followed by 1,1'-azobis(N,N-dimethylformamide) (118 mg, 0.680 mmol) and the mixture was stirred at room temperature overnight. The reaction mixture was evaporated and the crude product was purified by preparative HPLC (XTerra C18, 50 mM $NH_4HCO_3$ pH 10-$CH_3CN$) to give the title compound (8.0 mg) as a brown oil. MS m/z 355 $[M+H]^+$.

Example 2

2,4-Dimethyl-8-(phenylsulfonyl)-1,3,4,8-tetrahydro-2H-[1,4]oxazepino[6,7-e]indole trifluoroacetate To a solution of 5-(benzyloxy)-1-(phenylsulfonyl)-1H-indole-4-carbaldehyde (Intermediate 4, 0.050 g, 0.12 mmol) in DCE (3 mL) was added 1-amino-2-propanol, (0.020 g, 0.27 mmol) and sodium triacetoxyborohydride (0.080 g, 0.38 mmol) and the mixture was stirred at room temperature overnight. To the reaction mixture was added formaldehyde (37 wt. % in $H_2O$, 0.10 mL, 1.2 mmol) and sodium triacetoxyborohydride, (0.10 g, 0.48 mmol) and the mixture was stirred at room temperature for one hour. The solvent was removed under reduced pressure and the residue was dissolved in MeOH (2 mL). Pd/C 10 wt. % (0.020 g, 0.019 mmol) was added and the mixture was flushed with $N_2$ gas. Ammonium formate (0.050 g, 0.80 mmol) was added and the reaction mixture was stirred at room temperature overnight. The solvent was removed under reduced pressure, the semisolid was taken up in CHCl$_3$/H$_2$O, and the mixture was washed with water and brine, dried (MgSO$_4$) and the solvent was removed under reduced pressure. The crude material was dissolved in dry DCM (1 mL) and triphenylphosphine (8.0 mg, 0.030 mmol) was added followed by 1,1'-azobis(N,N-dimethylformamide) (5.2 mg, 0.030 mmol) and the mixture was stirred at room temperature overnight. The reaction mixture was evaporated and the crude product was purified by preparative HPLC (ACE C8, 0.1% TFA-CH$_3$CN) to give the title compound (7.4 mg) in the form of the trifluoroacetate salt. MS m/z 357 [M+H]$^+$.

Example 3

2-Isopropyl-8-(phenylsulfonyl)-1,3,4,8-tetrahydro-2H-[1,4]oxazepino[6,7-e]indole trifluoroacetate To a solution of 5-(benzyloxy)-1-(phenylsulfonyl)-1H-indole-4-carbaldehyde (Intermediate 4, 0.033 g, 0.084 mmol) in DCE (2.5 mL) was added N-isopropyl ethanolamine (0.017 g, 0.17 mmol) and sodium triacetoxyborohydride (0.036 g, 0.17 mmol) and the mixture was heated in a sealed pyrex tube at 40° C. overnight. The solvent was removed under reduced pressure and the residue was dissolved in MeOH (2 mL). Pd/C 10 wt. % (0.020 g, 0.019 mmol) was added and the mixture was flushed with N$_2$ gas. Ammonium formate (0.021 g, 0.34 mmol) was added and the reaction mixture was stirred at 40° C. overnight. The reaction mixture was filtered through a plug of hydromatrix with DCM as the eluent and the filtrate was evaporated. The crude material was dissolved in dry DCM (1 mL) and triphenylphosphine (0.044 g, 0.017 mmol) was added followed by 1,1'-azobis(N,N-dimethylformamide) (0.029 g, 0.017 mmol) and the mixture was stirred at room temperature overnight. The reaction mixture was evaporated and the crude product was purified by preparative HPLC (ACE C8, 0.1% TFA-CH$_3$CN) to give the title compound (5.2 mg) as a colorless oil in the form of the trifluoroacetate salt. MS m/z 371 [M+H]$^+$.

Example 4

2-Ethyl-8-(phenylsulfonyl)-1,3,4,8-tetrahydro-2H-[1,4]oxazepino[6,7-e]indole trifluoroacetate To a solution of 5-(benzyloxy)-1-(phenylsulfonyl)-1H-indole-4-carbaldehyde (Intermediate 4, 0.033 g, 0.084 mmol) in DCE (2.5 mL) was added N-ethyl ethanolamine (0.015 g, 0.17 mmol) and sodium triacetoxyborohydride (0.036 g, 0.17 mmol) and the mixture was heated in a sealed pyrex tube at 40° C. overnight. The solvent was removed under reduced pressure and the residue was dissolved in MeOH (2 mL). Pd/C 10 wt. % (0.010 g, 0.0095 mmol) was added and the mixture was flushed with N$_2$ gas. Ammonium formate (0.021 g, 0.34 mmol) was added and the reaction mixture was stirred at 40° C. overnight. The reaction mixture was filtered through a plug of hydromatrix with DCM as the eluent and the filtrate was evaporated. The crude material was dissolved in dry DCM (1 mL) and triphenylphosphine (0.044 g, 0.017 mmol) was added followed by 1,1'-azobis(N,N-dimethylformamide) (0.029 g, 0.017 mmol) and the mixture was stirred at room temperature overnight. The reaction mixture was evaporated and the crude product was purified by preparative HPLC (ACE C8, 0.1% TFA-CH$_3$CN) to give the title compound (0.8 mg) as a colorless oil in the form of the trifluoroacetate salt. MS m/z 357 [M+H]$^+$.

Intermediate 5

4-{[(2-Hydroxy-ethyl)-methyl-amino]-methyl}-1H-indol-5-ol

Paraformaldehyde (0.060 g, 2 mmol) and 2-methylamino ethanol (0.15 g, 2.0 mmol) was suspended in ethanol (10 mL) and heated at 50° C. for 20 minutes. The solution was cooled to room temperature and 5-hydroxyindole (0.27 mg, 2.0 mmol) was added. The solution was stirred under an atmosphere of N$_2$ at room temperature overnight. The solution was evaporated to give the title compound (441 mg) that was used in the next step without further purification. MS m/z 221 [M+H]$^+$.

Intermediate 6

2-Methyl-1,3,4,8-tetrahydro-2H-[1,4]oxazepino[6,7-e]indole

4-{[(2-Hydroxy-ethyl)-methyl-amino]-methyl}-1H-indol-5-ol (Intermediate 5, 0.44 g, 2.0 mmol), 1,1'-Azobis(N,N-dimethylformamide) (0.52 mg, 3.0 mmol) and triphenylphosphine (0.79 mg, 3.0 mmol) was dissolved in THF (10 mL) and stirred at room temperature overnight. The mixture was evaporated and the crude material was purified by flash chromatography on silica gel using a MeOH-ethylacetate gradient, 4-32% MeOH, to give 136 mg of the title compound. MS m/z 203 [M+H]$^+$.

Example 5

2-Methyl-8-(phenylsulfonyl)-1,3,4,8-tetrahydro-2H-[1,4]oxazepino[6,7-e]indole

DMF (15 mL) was added to a vial containing 2-methyl-1,3,4,8-tetrahydro-2H-[1,4]oxazepino[6,7-e]indole (Intermediate 6, 0.250 g, 1.24 mmol) and sodium hydride (60% in mineral oil, 0.100 g, 2.50 mmol). The mixture was stirred for 20 minutes at room temperature before benzenesulfonyl chloride (0.327 g, 1.85 mmol) was added. The reaction was allowed to stir for 30 minutes before 2 M HCl (0.5 mL) was added and the mixture was diluted with 1 M Na$_2$CO$_3$ and diethylether. The organic phase was washed with water, dried (MgSO$_4$) and evaporated. The crude product was dissolved in DCM (2 mL) and hexane (20 mL) was added. The mixture was allowed to stand overnight and the light yellow crystals were filtered and washed with hexane to give title compound (202 mg) as a light yellow solid. MS m/z 343 [M+H]$^+$.

General Procedure for the Preparation of Examples 6-34

2-Methyl-1,3,4,8-tetrahydro-2H-[1,4]oxazepino[6,7-e]indole (Intermediate 6, 0.010 g, 0.050 mmol) was dissolved in dry DMF (0.2 mL) and sodium hydride (60% in mineral oil, 0.6 mg, 0.1 mmol) was added. The reaction mixture was shaken at room temperature for 10 minutes and the requisite sulfonyl chloride (0.1 mmol in 0.15 mL of dry DMF) was added. The reaction was shaken at room temperature for 10-20 minutes and then quenched by adding 1 mL of a mixture of methanol and acetic acid (1:1). The crude products were purified as described below.

Example 6

8-(2,3-Dihydro-1,4-benzodioxin-6-ylsulfonyl)-2-methyl-1,3,4,8-tetrahydro-2H-[1,4]oxazepino[6,7-e]indole Sulfonyl chloride: 2,3-dihydro-1,4-benzodioxine-6-sulfonyl chloride (0.023 g, 0.10 mmol)
The crude product was purified by preparative HPLC (XTerra C18, 50 mM NH$_4$HCO$_3$ pH 10-CH$_3$CN) to give the title compound (11 mg). MS m/z 401 [M+H]$^+$.

Example 7

8-[(3,4-Dimethoxyphenyl)sulfonyl]-2-methyl-1,3,4,8-tetrahydro-2H-[1,4]oxazepino[6,7-e]indole Sulfonyl chloride: 3,4-dimethoxybenzenesulfonyl chloride (0.024 g, 0.10 mmol)
The crude product was purified by preparative HPLC (XTerra C18, 50 mM NH$_4$HCO$_3$ pH 10-CH$_3$CN) to give the title compound (10.9 mg). MS m/z 403 [M+H]$^+$.

Example 8

8-(1-Benzofuran-2-ylsulfonyl)-2-methyl-1,3,4,8-tetrahydro-2H-[1,4]oxazepino[6,7-e]indole Sulfonyl chloride: 1-benzofuran-2-sulfonyl chloride (0.022 g, 0.10 mmol)
The crude product was purified by preparative HPLC (XTerra C18, 50 mM NH$_4$HCO$_3$ pH 10-CH$_3$CN) to give the title compound (5.5 mg). MS m/z 383 [M+H]$^+$.

Example 9

8-[(2,5-Dimethyl-3-furyl)sulfonyl]-2-methyl-1,3,4,8-tetrahydro-2H-[1,4]oxazepino[6,7-e]indole Sulfonyl chloride: 2,5-dimethyl-3-furansulfonyl chloride (0.019 g, 0.10 mmol)
The crude product was purified by preparative HPLC (XTerra C18, 50 mM NH$_4$HCO$_3$ pH 10-CH$_3$CN) to give the title compound (11.4 mg). MS m/z 361 [M+H]$^+$.

Example 10

8-(1,3-Benzothiazol-6-ylsulfonyl)-2-methyl-1,3,4,8-tetrahydro-2H-[1,4]oxazepino[6,7-e]indole Sulfonyl chloride: 1,3-benzothiazole-6-sulfonyl chloride (0.023 g, 0.10 mmol).
The crude product was purified by preparative HPLC (XTerra C18, 50 mM NH$_4$HCO$_3$ pH 10-CH$_3$CN) to give the title compound (7.1 mg). MS m/z 400 [M+H]$^+$.

Example 11

2-Methyl-8-{[4-(methylsulfonyl)phenyl]sulfonyl}-1,3,4,8-tetrahydro-2H-[1,4]oxazepino[6,7-e]indole Sulfonyl chloride: 4-methylsulfonylbenzenesulfonyl chloride (0.025 g, 0.10 mmol).
The crude product was purified by preparative HPLC (XTerra C18, 50 mM NH$_4$HCO$_3$ pH 10-CH$_3$CN) to give the title compound (9.5 mg). MS m/z 421 [M+H]$^+$.

Example 12

8-[(4-Isopropylphenyl)sulfonyl]-2-methyl-1,3,4,8-tetrahydro-2H-[1,4]oxazepino[6,7-e]indole Sulfonyl chloride: 4-isopropylbenzene-1-sulfonyl chloride (0.022 g, 0.10 mmol).
The crude product was purified by preparative HPLC (XTerra C18, 50 mM NH$_4$HCO$_3$ pH 10-CH$_3$CN) to give the title compound (10.7 mg). MS m/z 385 [M+H]$^+$.

Example 13

8-[(2,2-Dimethyl-3,4-dihydro-2H-chromen-6-yl)sulfonyl]-2-methyl-1,3,4,8-tetrahydro-2H-[1,4]oxazepino[6,7-e]indole Sulfonyl chloride: 2,2-dimethyl-6-chromanesulfonyl chloride (0.026 g, 0.10 mmol).
The crude product was purified by preparative HPLC (XTerra C18, 50 mM NH$_4$HCO$_3$ pH 10-CH$_3$CN) to give the title compound (9.6 mg). MS m/z 427 [M+H]$^+$.

Example 14

8-[(2-Chloro-4-fluorophenyl)sulfonyl]-2-methyl-1,3,4,8-tetrahydro-2H-[1,4]oxazepino[6,7-e]indole Sulfonyl chloride: 2-chloro-4-fluorobenzene sulfonyl chloride (0.023 g, 0.10 mmol).
The crude product was purified by preparative HPLC (XTerra C18, 50 mM NH$_4$HCO$_3$ pH 10-CH$_3$CN) to give the title compound (10.3 mg). MS m/z 395 [M+H]$^+$.

Example 15

8-[(3,4-Dichlorophenyl)sulfonyl]-2-methyl-1,3,4,8-tetrahydro-2H-[1,4]oxazepino[6,7-e]indole Sulfonyl chloride: 3,4-dichlorobenzenesulfonyl chloride (0.025 g, 0.10 mmol).
The crude product was purified by preparative HPLC (XTerra C18, 50 mM NH$_4$HCO$_3$ pH 10-CH$_3$CN) to give the title compound (12.2 mg). MS m/z 412 [M+H]$^+$.

Example 16

8-[(4-Fluorophenyl)sulfonyl]-2-methyl-1,3,4,8-tetrahydro-2H-[1,4]oxazepino[6,7-e]indole Sulfonyl chloride: 4-fluorobenzenesulfonyl chloride (0.019 g, 0.10 mmol).
The crude product was purified by preparative HPLC (XTerra C18, 50 mM NH$_4$HCO$_3$ pH 10-CH$_3$CN) to give the title compound (12.8 mg). MS m/z 361 [M+H]$^+$.

Example 17

8-[(2,6-Difluorophenyl)sulfonyl]-2-methyl-1,3,4,8-tetrahydro-2H-[1,4]oxazepino[6,7-e]indole Sulfonyl chloride: 2,6-difluorobenzene sulfonyl chloride (0.021 g, 0.10 mmol). The crude product was purified by preparative HPLC (XTerra C18, 50 mM NH$_4$HCO$_3$ pH 10-CH$_3$CN) to give the title compound (11.2 mg). MS m/z 379 [M+H]$^+$.

Example 18

2-Methyl-8-{[4-(trifluoromethoxy)phenyl]sulfonyl}-1,3,4,8-tetrahydro-2H-[1,4]oxazepino[6,7-e]indole Sulfonyl chloride: 4-(trifluoromethoxy)benzene-1-sulfonyl chloride (0.026 g, 0.10 mmol).
The crude product was purified by preparative HPLC (XTerra C18, 50 mM $NH_4HCO_3$ pH 10-$CH_3CN$) to give the title compound (16.8 mg). MS m/z 427 $[M+H]^+$.

Example 19

2-Methyl-8-(2-naphthylsulfonyl)-1,3,4,8-tetrahydro-2H-[1,4]oxazepino[6,7-e]indole Sulfonyl chloride: 2-naphthalenesulfonyl chloride (0.023 g, 0.10 mmol). The crude product was purified by preparative HPLC (XTerra C18, 50 mM $NH_4HCO_3$ pH 10-$CH_3CN$) to give the title compound (19.8 mg). MS m/z 393 $[M+H]^+$.

Example 20

8-[(3-Chloro-4-methylphenyl)sulfonyl]-2-methyl-1,3,4,8-tetrahydro-2H-[1,4]oxazepino[6,7-e]indole Sulfonyl chloride: 3-chloro-4-methylbenzenesulfonyl chloride (0.023 g, 0.10 mmol).
The crude product was purified by preparative HPLC (XTerra C18, 50 mM $NH_4HCO_3$ pH 10-$CH_3CN$) to give the title compound (2.2 mg). MS m/z 391 $[M+H]^+$.

Example 21

8-[(4,5-Dichloro-2-thienyl)sulfonyl]-2-methyl-1,3,4,8-tetrahydro-2H-[1,4]oxazepino[6,7-e]indole Sulfonyl chloride: 2,3-dichlorothiophene-5-sulfonyl chloride (0.025 g, 0.10 mmol).
The crude product was purified by preparative HPLC (XTerra C18, 50 mM $NH_4HCO_3$ pH 10-$CH_3CN$) to give the title compound (11.5 mg). MS m/z 418 $[M+H]^+$.

Example 22

8-[(5-Chloro-3-methyl-1-benzothien-2-yl)sulfonyl]-2-methyl-1,3,4,8-tetrahydro-2H-[1,4]oxazepino[6,7-e]indole Sulfonyl chloride: 5-chloro-3-methylbenzo(b)thiophene-2-sulfonyl chloride (0.028 g, 0.10 mmol).
The crude product was purified by preparative HPLC (XTerra C18, 50 mM $NH_4HCO_3$ pH 10-$CH_3CN$) to give the title compound (9 mg). MS m/z 447 $[M+H]^+$.

Example 23

8-[(2,4-Dichlorophenyl)sulfonyl]-2-methyl-1,3,4,8-tetrahydro-2H-[1,4]oxazepino[6,7-e]indole Sulfonyl chloride: 2,4-dichlorobenzenesulfonyl chloride (0.025 g, 0.10 mmol).
The crude product was purified by preparative HPLC (XTerra C18, 50 mM $NH_4HCO_3$ pH 10-$CH_3CN$) to give the title compound (9 mg). MS m/z 412 $[M+H]^+$.

Example 24

8-{[4-Fluoro-3-(trifluoromethyl)phenyl]sulfonyl}-2-methyl-1,3,4,8-tetrahydro-2H-[1,4]oxazepino[6,7-e]indole Sulfonyl chloride: 4-fluoro-3-trifluoromethylbenzenesulfonyl chloride (0.026 g, 0.10 mmol).
The crude product was purified by preparative HPLC (XTerra C18, 50 mM $NH_4HCO_3$ pH 10-$CH_3CN$) to give the title compound (4 mg). MS m/z 429 $[M+H]^+$.

Example 25

2-Methyl-8-(2-thienylsulfonyl)-1,3,4,8-tetrahydro-2H-[1,4]oxazepino[6,7-e]indole Sulfonyl chloride: 2-thienylsulfonyl chloride (0.018 g, 0.10 mmol).
The crude product was purified by preparative HPLC (XTerra C18, 50 mM $NH_4HCO_3$ pH 10-$CH_3CN$) to give the title compound (2 mg). MS m/z 349 $[M+H]^+$.

Example 26

2-Methyl-8-[(4-methylphenyl)sulfonyl]-1,3,4,8-tetrahydro-2H-[1,4]oxazepino[6,7-e]indole Sulfonyl chloride: 4-toluene sulfonyl chloride (0.019 g, 0.10 mmol).
The crude product was purified by preparative HPLC (XTerra C18, 50 mM $NH_4HCO_3$ pH 10-$CH_3CN$) to give the title compound (12 mg). MS m/z 357 $[M+H]^+$.

Example 27

8-[(2-Methoxy-5-methylphenyl)sulfonyl]-2-methyl-1,3,4,8-tetrahydro-2H-[1,4]oxazepino[6,7-e]indole Sulfonyl chloride: 2-methoxy-5-methylbenzenesulfonyl chloride (0.022 g, 0.10 mmol).
The crude product was purified by preparative HPLC (XTerra C18, 50 mM $NH_4HCO_3$ pH 10-$CH_3CN$) to give the title compound (12 mg). MS m/z 387 $[M+H]^+$.

Example 28

8-[(3-Fluoro-4-methylphenyl)sulfonyl]-2-methyl-1,3,4,8-tetrahydro-2H-[1,4]oxazepino[6,7-e]indole Sulfonyl chloride: 3-fluoro-4-methylbenzenesulfonyl chloride (0.021 g, 0.10 mmol).
The crude product was purified by preparative HPLC (XTerra C18, 50 mM $NH_4HCO_3$ pH 10-$CH_3CN$) to give the title compound (12 mg). MS m/z 375 $[M+H]^+$.

Example 29

8-(1-Benzothien-3-ylsulfonyl)-2-methyl-1,3,4,8-tetrahydro-2H-[1,4]oxazepino[6,7-e]indole Sulfonyl chloride: 1-benzothiophene-3-sulfonyl chloride (0.023 g, 0.10 mmol).
The crude product was purified by preparative HPLC (XTerra C18, 50 mM $NH_4HCO_3$ pH 10-$CH_3CN$) to give the title compound (12 mg). MS m/z 399 $[M+H]^+$.

Example 30

8-[(4-Methoxyphenyl)sulfonyl]-2-methyl-1,3,4,8-tetrahydro-2H-[1,4]oxazepino[6,7-e]indole Sulfonyl chloride: 4-methoxybenzenesulfonyl chloride (0.021 g, 0.10 mmol).
The crude product was purified by preparative HPLC (XTerra C18, 50 mM NH$_4$HCO$_3$ pH 10-CH$_3$CN) to give the title compound (6.2 mg). MS m/z 373 [M+H]$^+$.

Example 31

2-Methyl-8-{[4-(trifluoromethyl)phenyl]sulfonyl}-1,3,4,8-tetrahydro-2H-[1,4]oxazepino[6,7-e]indole Sulfonyl chloride: 4-(trifluoromethyl)-benzenesulfonyl chloride (0.024 g, 0.10 mmol).
The crude product was purified by preparative HPLC (XTerra C18, 50 mM NH$_4$HCO$_3$ pH 10-CH$_3$CN) to give the title compound (11.6 mg). MS m/z 411 [M+H]$^+$.

Example 32

2-Methyl-8-[(4-propylphenyl)sulfonyl]-1,3,4,8-tetrahydro-2H-[1,4]oxazepino[6,7-e]indole Sulfonyl chloride: 4-propylbenzenesulfonyl chloride (0.022 g, 0.10 mmol).
The crude product was purified by preparative HPLC (XTerra C18, 50 mM NH$_4$HCO$_3$ pH 10-CH$_3$CN) to give the title compound (13 mg). MS m/z 385 [M+H]$^+$.

Example 33

3-Chloro-4-[(2-methyl-1,2,3,4-tetrahydro-8H-[1,4]oxazepino [6,7-e]indol-8-yl)sulfonyl]benzonitrile Sulfonyl chloride: 2-chloro-4-cyanobenzenesulfonyl chloride (0.024 g, 0.10 mmol).
The crude product was purified by preparative HPLC (XTerra C18, 50 mM NH$_4$HCO$_3$ pH 10-CH$_3$CN) to give the title compound (2 mg). MS m/z 402 [M+H]$^+$. Example 34

8-[(2,5-Dimethyl-3-thienyl)sulfonyl]-2-methyl-1,3,4,8-tetrahydro-2H-[1,4]oxazepino[6,7-e]indole Sulfonyl chloride: 2,5-dimethyl-3-thiophenesulfonyl chloride (0.021 g, 0.10 mmol).
The crude product was purified by preparative HPLC (XTerra C18, 50 mM NH$_4$HCO$_3$ pH 10-CH$_3$CN) to give the title compound (11.3 mg). MS m/z 377 [M+H]$^+$.

Example 35

2-[(2-Methyl-1,2,3,4-tetrahydro-8H-[1,4]oxazepino [6,7-e]indol-8-yl)sulfonyl]benzonitrile NaH (60% in mineral oil, 0.040 g, 1.0 mmol) was charged into a pyrex tube under nitrogen gas and 2-methyl-1,3,4,8-tetrahydro-2H-[1,4]oxazepino[6,7-e]indole (Intermediate 6, 100 mg, 0.492 mmol) in dry DMF (1 mL) was added. The reaction mixture was stirred at room temperature for 20 minutes before 2-cyanobenzenesulfonyl chloride (0.11 g, 0.50 mmol) was added and the reaction mixture was stirred for 1 hour. Water (2 mL) was added and the solution was extracted with DCM. The combined organics were evaporated and the solid residue was washed with diethyl ether to give 64 mg of the title compound. MS m/z 368 [M+H]$^+$.

Example 36

2-Methyl-1-[2-methyl-8-(phenylsulfonyl)-1,3,4,8-tetrahydro-2H-[1,4]oxazepino[6,7-e]indol-9-yl]propan-1-one trifluoroacetate 2-Methyl-8-(phenylsulfonyl)-1,3,4,8-tetrahydro-2H-[1,4]oxazepino[6,7-e]indole (Example 5, 0.020 g, 0.058 mmol) in THF (1 mL) was cooled to −78° C. under an atmosphere of nitrogen gas. BuLi (1.6 M in hexanes, 0.11 mL, 0.18 mmol) was added, and the solution was stirred for 10 minutes before methyl isobutanoate (0.20 mL, 0.18 mmol) was added. Stirring was continued overnight and the temperature of the reaction mixture was allowed to reach room temperature. The reaction mixture was evaporated and purified by preparative HPLC (ACE C8, 0.1% TFA-CH$_3$CN) to give the title compound (6 mg) in the form of the trifluoroacetate salt. MS m/z 413 [M+H]$^+$.

Example 37

1-[2-Methyl-8-(phenylsulfonyl)-1,3,4,8-tetrahydro-2H-[1,4]oxazepino[6,7-e]indol-9-yl]ethanone trifluoroacetate 2-Methyl-8-(phenylsulfonyl)-1,3,4,8-tetrahydro-2H-[1,4]oxazepino[6,7-e]indole (Example 5, 0.020 g, 0.058 mmol) in THF (1 mL) was cooled to −78° C. under an atmosphere of nitrogen gas. BuLi (1.6 M in hexanes, 0.11 mL, 0.18 mmol) was added and the solution was stirred for 10 minutes before acetic anhydride (0.18 mL, 0.18 mmol) was added. Stirring was continued overnight and the temperature of the reaction mixture was allowed to reach room temperature. The reaction mixture was evaporated and purified by preparative HPLC (ACE C8, 0.1% TFA-CH$_3$CN) to give the title compound (18 mg) in the form of the trifluoroacetate salt. MS m/z 385 [M+H]$^+$.

Example 38

9-Chloro-2-methyl-8-(phenylsulfonyl)-1,3,4,8-tetrahydro-2H-[1,4]oxazepino[6,7-e]indole trifluoroacetate 2-Methyl-8-(phenylsulfonyl)-1,3,4,8-tetrahydro-2H-[1,4]oxazepino[6,7-e]indole (Example 5, 0.030 g, 0.088 mmol) was dissolved in dry THF (1 mL) at −78° C. under an atmosphere of nitrogen gas. BuLi (2.5 M in hexanes, 0.053 mL, 0.13 mmol) was added. The solution was stirred for 15 minutes and thiophene-2-sulfonyl chloride (24 mg, 0.13 mmol) was added. The temperature of the reaction mixture was allowed to rise to room temperature overnight and evaporated. The material was purified by preparative HPLC (ACE C8, 0.1% TFA-CH$_3$CN) to give the title compound (5.2 mg) in the form of the trifluoroacetate salt. MS m/z 377 [M+H]$^+$.

Example 39

2-[2-Methyl-8-(phenylsulfonyl)-1,3,4,8-tetrahydro-2H-[1,4]oxazepino[6,7-e]indol-9-yl]propan-2-ol trifluoroacetate 2-Methyl-8-(phenylsulfonyl)-1,3,4,8-tetrahydro-2H-[1,4]oxazepino[6,7-e]indole (Example 5, 0.030 g, 0.088 mmol)

was dissolved in dry THF (1 mL) at −78° C. under an atmosphere of nitrogen gas. BuLi (2.5 M in hexanes, 0.053 mL, 0.13 mmol) was added and the solution was stirred for 15 minutes before acetone (0.010 mL, 0.13 mmol) was added. The temperature of the reaction mixture was allowed to rise to room temperature overnight. The material was purified by preparative HPLC (ACE C8, 0.1% TFA-CH$_3$CN) to give the title compound (10.5 mg) in the form of the trifluoroacetate salt. MS m/z 401 [M+H]$^+$.

Example 40

Cyclopropyl[2-methyl-8-(phenylsulfonyl)-1,3,4,8-tetrahydro-2H-[1,4]oxazepino[6,7-e]indol-9-yl]methanol 2-Methyl-8-(phenylsulfonyl)-1,3,4,8-tetrahydro-2H-[1,4]oxazepino[6,7-e]indole (Example 5, 0.030 g, 0.088 mmol) was dissolved in dry THF (1 mL) at −78° C. under an atmosphere of nitrogen gas. BuLi (2.5 M in hexanes, 0.053 mL, 0.13 mmol) was added. The solution was stirred for 15 minutes before methyl cyclopropane carboxylate (0.013 mL, 0.13 mmol) was added. The temperature of the reaction mixture was allowed to rise to room temperature overnight. The crude product was purified by preparative HPLC (XTerra C18, 50 mM NH$_4$HCO$_3$ pH 10-CH$_3$CN) to give the title compound (1.5 mg). MS m/z 413 [M+H]$^+$.

Example 41

1-[2-Methyl-8-(phenylsulfonyl)-1,3,4,8-tetrahydro-2H-[1,4]oxazepino[6,7-e]indol-9-yl]ethanol trifluoroacetate 2-Methyl-8-(phenylsulfonyl)-1,3,4,8-tetrahydro-2H-[1,4]oxazepino[6,7-e]indole (Example 5, 0.030 g, 0.88 mmol) was dissolved in dry THF (1 mL) at −78° C. under an atmosphere of nitrogen gas. BuLi (2.5 M in hexanes, 0.053 mL, 0.13 mmol) was added. The solution was stirred for 15 minutes before acetic anhydride (0.012 mL, 0.13 mmol) was added. The temperature of the reaction mixture was allowed to rise to room temperature overnight. The material was purified by preparative HPLC (ACE C8, 0.1% TFA-CH$_3$CN) to give the title compound (4.1 mg) as a white solid in the form of the trifluoroacetate salt. MS m/z 387 [M+H]$^+$.

Example 42

10-Chloro-2-methyl-8-(phenylsulfonyl)-1,3,4,8-tetrahydro-2H-[1,4]oxazepino[6,7-e]indole N-chlorosuccinimide (NCS) (29 mg, 0.21 mmol) was added to a solution of 2-methyl-8-(phenylsulfonyl)-1,3,4,8-tetrahydro-2H-[1,4]oxazepino[6,7-e]indole Example 5, 0.050 g, 0.15 mmol) in THF (2 mL) and the reaction mixture was heated at 50° C. overnight. Additional NCS (0.030 g, 0.22 mmol) was added and the mixture was heated for 4 days at 50° C. The mixture was evaporated and the crude material was purified by flash chromatography on silica gel using MeOH:DCM:NEt$_3$ (2:97:1) to give 7.3 mg of a white solid. MS m/z 377 [M+H]$^+$.

Intermediate 7

5-(Benzyloxy)-1-(phenylsulfonyl)-1H-indole

4 M NaOH (100 mL, 0.4 mol) was added to a solution of 5-benzyloxyindole (20 g, 0.09 mol), tetrabutylammonium hydrogen sulfate (6.1 g, 0.018 mol) and benzenesulfonyl chloride (27 g, 0.15 mol) in DCM (500 mL) The mixture was stirred at room temperature for 6 hours and additional benzenesulfonyl chloride (4.1 g, 0.023 mol) was added. The mixture was stirred overnight and diluted with water and DCM. The mixture was transferred to a separation funnel and extracted with DCM (2×), dried (MgSO$_4$) and evaporated. The crude product was suspended in diethylether (1000 mL) and filtered. The solid cake was washed with diethylether (2×) and discarded. The filtrate was evaporated to approximate 100 mL (precipitation of white solid) and filtered. The white crystals were washed with cold diethylether (2×) and dried in vacuo to give 15 g of a white solid. MS m/z 364 [M+H]$^+$ Intermediate 8

1-(Phenylsulfonyl)-1H-indol-5-ol

Pd/C 10 wt. % (0.10 g, 0.094 mmol) was added to a solution of 5-(benzyloxy)-1-(phenylsulfonyl)-1H-indole (Intermediate 7, 6.00 g, 16.5 mmol) and ammonium formate (15.6 g, 248 mmol) in THF/MeOH 1:1 (300 mL). The reaction mixture was stirred overnight at room temperature and filtered through a short plug of silica gel. The filtrate was evaporated and dissolved in DCM and filtered through a plug of silica gel eluating with 2.5% MeOH in DCM. The purest fractions (monitored by TLC) were evaporated to give the title compound (4.2 g) as a white powder. MS m/z 273 [M+H]$^+$.

Intermediate 9

4-(Hydroxymethyl)-1-(phenylsulfonyl)-1H-indol-5-ol 1-(Phenylsulfonyl)-1H-indol-5-ol (Intermediate 8, 0.80 g, 2.9 mmol) was dissolved in MeOH (20 mL) and formaldehyde (37 wt. % in H$_2$O, 4.0 mL, 49 mmol) was added followed by a solution of KOH (1.64 g, 29.3 mmol) in water (20 mL). The reaction mixture was heated at 40° C. overnight. The mixture was made acidic with 1 M HCl and diluted with DCM, transferred to a separation funnel and extracted with DCM (2×). The combined organics were washed with brine (1×), dried (MgSO$_4$) and evaporated. The crude product was dissolved in diethylether (100 mL) and evaporated to approximately 20 mL (precipitation of white crystals). The white crystals were filtered and washed with diethylether (2×) to give 0.43 g of the title compound as a white solid. MS m/z 286 [M+H—H$_2$O]$^+$.

Intermediate 10

5-Hydroxy-1-(phenylsulfonyl)-1H-indole-4-carbaldehyde 4-(Hydroxymethyl)-1-(phenylsulfonyl)-1H-indol-5-ol (Intermediate 9, 439 mg, 1.45 mmol) was dissolved in dry DCM (25 mL) and manganese dioxide (0.75 g, 8.7 mmol) was added all in one portion. The reaction mixture was stirred for 2 hours at room temperature and the mixture was filtered through a pad of silica gel. The filtrate was washed with water (1×), dried (MgSO$_4$) and evaporated to give 0.2 g of an orange solid. MS m/z 302 [M+H]$^+$.

Example 43

(7aR)-3-(Phenylsulfonyl)-3,7a,8,9,10,12-hexahydro-7H-pyrrolo[2',1':3,4][1,4]oxazepino[6,7-e]indole trifluoroacetate 1,1'-Azobis(N,N-dimethylformamide) (23 mg, 0.13 mmol) was added to a solution of 5-hydroxy-1-(phenylsulfonyl)-1H-indole-4-carbaldehyde (Intermediate 10, 0.020 g, 0.067 mmol), (R)-1-Boc-2-pyrrolidinemethanol (26.7 mg, 0.133 mmol) and triphenylphosphine (34.8 mg, 0.133 mmol) in DCM (2 mL). The reaction mixture was stirred overnight at room temperature, evaporated and the crude material was purified by flash chromatography on silica gel using 2.5% MeOH in DCM as the eluent. The purest fractions were evaporated and dissolved in DCM (3 mL) and TFA (1 mL) was added. The mixture was stirred for 2 hours, evaporated and dissolved in THF (1 mL). Sodium triacetoxyborohydride (56 mg, 0.27 mmol) was added and the mixture was stirred for 15 minutes at room temperature and evaporated. The material was purified by preparative HPLC (ACE C8, 0.1% TFA-CH$_3$CN) to give the title compound as a light brown liquid (8 mg) in the form of the trifluoroacetate salt. MS m/z 369 [M+H]$^+$.

Example 44

(7aS)-3-(Phenylsulfonyl)-3,7a,8,9,10,12-hexahydro-7H-pyrrolo[2',1':3,4][1,4]oxazepino[6,7-e]indole trifluoroacetate 1,1'-Azobis(N,N-dimethylformamide) (34 mg, 0.20 mmol) was added to a solution of 5-hydroxy-1-(phenylsulfonyl)-1H-indole-4-carbaldehyde (Intermediate 10, 0.030 g, 0.10 mmol), (S)-1-Boc-2-pyrrolidinemethanol (40.0 mg, 0.20 mmol) and triphenylphosphine (52 mg, 0.20 mmol) in DCM (2 mL). The mixture was heated at 45° C. for 3 hours, evaporated and the crude material was purified by flash chromatography on silica gel using 1% to 2.5% MeOH in DCM as the eluent. This boc-protected intermediate was dissolved in DCM (2 mL) and TFA (1 mL) was added. The mixture was allowed to stir for 1 hour at room temperature and evaporated. The residue was dissolved in THF (2 mL) and sodium triacetoxyborohydride (84.0 mg, 0.40 mmol) was added. The mixture was stirred for 20 minutes and evaporated. The crude material was purified by preparative HPLC (ACE C8, 0.1% TFA-CH$_3$CN) to give the title compound as a yellow oil (9 mg) in the form of the trifluoroacetate salt. MS m/z 369 [M+H]$^+$.

Example 45

(3S)-3-Methyl-8-(phenylsulfonyl)-1,3,4,8-tetrahydro-2H-[1,4]oxazepino [6,7-e]indole 1,1'-Azobis(N,N-dimethylformamide) (57 mg, 0.33 mmol) was added to a solution of 5-hydroxy-1-(phenylsulfonyl)-1H-indole-4-carbaldehyde (Intermediate 10, 0.050 g, 0.16 mmol), S-(–)-2-(tert-butoxycarbonylamino)-1-propanol (58 mg, 0.33 mmol) and triphenylphosphine (87 mg, 0.33 mmol) in DCM (5 mL). The mixture was stirred at 45° C. for 2 days and the mixture was evaporated. The crude material was purified by flash chromatography using 1% to 2.5% MeOH in DCM. This boc-protected intermediate was dissolved in DCM (3 mL) and TFA (1 mL) was added. The mixture was stirred for 1 hour and evaporated. The residue was dissolved in THF (3 mL) and sodium triacetoxyborohydride (30.0 mg, 0.141 mmol) was added all in one portion. The reaction mixture was stirred for 20 minutes and evaporated. The crude product was purified by flash chromatography on silica gel using MeOH:DCM:NEt$_3$ (5:94:1) as the eluent to give a light yellow solid (15 mg) of the title compound. MS m/z 343 [M+H]$^+$.

Example 46

(3S)-2,3-Dimethyl-8-(phenylsulfonyl)-1,3,4,8-tetrahydro-2H-[1,4]oxazepino[6,7-e]indole trifluoroacetate (3S)-3-Methyl-8-(phenylsulfonyl)-1,3,4,8-tetrahydro-2H-[1,4]oxazepino[6,7-e]indole (Example 45, 0.010 g, 0.029 mmol) was dissolved in THF (1 mL) and formaldehyde (37 wt. % in H$_2$O, 0.020 mL, 0.25 mmol) was added. The mixture was allowed to stir for 5 minutes before sodium triacetoxyborohydride (7.5 mg, 0.044 mmol) was added all in one portion. The mixture was stirred for 1 hour at room temperature and evaporated. The crude material was purified by preparative HPLC (ACE C8, 0.1% TFA-CH$_3$CN) to give the title compound as a light yellow gum (11.5 mg) in the form of the trifluoroacetate salt. MS m/z 357 [M+H]$^+$.

Intermediate 11

7-methyl-1H-indol-5-ol

Prepared according to PCT Int. Appl. WO 9523141, 1995.

Intermediate 12

4-{[(2-Hydroxyethyl)(methyl)amino]methyl}-7-methyl-1H-indol-5-ol

A mixture of paraformaldehyde (82.0 mg, 2.71 mmol) and 2-methylaminoethanol (0.218 mL, 2.71 mmol) in EtOH (2 mL) was heated at 50° C. for 20 minutes. 7-methyl-1H-indol-5-ol (Intermediate 11, 500 mg, 3.4 mmol) in EtOH (10 mL) was added and the mixture was stirred for 1.5 hours at room temperature. The mixture was diluted with DCM (15 mL) and divided in two portions to be purified on two SCX-columns (5 g) preconditioned with DCM/MeOH 1:1 (20 mL) and eluted with DCM/MeOH 1:1 (50 mL) (contains only sm) and 1 M MeOH (40 mL) (contains product) to give 490 mg of a brown oil that turned solid. MS m/z 235 [M+H]$^+$.

Intermediate 13

2,7-Dimethyl-1,3,4,8-tetrahydro-2H-[1,4]oxazepino[6,7-e]indole trifluoroacetate

4-{[(2-Hydroxyethyl)(methyl)amino]methyl}-7-methyl-1H-indol-5-ol (Intermediate 12, 490 mg, 2.1 mmol), triphenylphosphine (883 mg, 3.14 mmol) and 1,1'-azobis(N,N-dimethylformamide) (540 mg, 3.1 mmol) in THF (10 mL) was stirred overnight at room temperature. The mixture was diluted with MeOH and the material was purified by preparative HPLC (ACE C8, 0.1% TFA-CH$_3$CN) to give the title compound as a brown oil (60.8 mg) in the form of the trifluoroacetate salt. MS m/z 217 [M+H]$^+$.

Example 47

2,7-Dimethyl-8-(phenylsulfonyl)-1,3,4,8-tetrahydro-2H-[1,4]oxazepino[6,7-e]indole trifluoroacetate Sodium hydride (60% in mineral oil, 14 mg, 0.54 mmol, 95%) was added to a solution of 2,7-dimethyl-1,3,4,8-tetrahydro-2H-[1,4]oxazepino[6,7-e]indole trifluoroacetate (Intermediate 13, 0.060 g, 0.18 mmol) in DMF (2 mL) and stirred at room temperature for 5 minutes before benzenesulfonyl chloride (0.035 mL, 0.27 mmol) was added. The mixture was stirred at room temperature for 10 minutes and quenched with ice/water and extracted with DCM. The crude material was purified by preparative HPLC (ACE C8, 0.1% TFA-CH$_3$CN) to give the title compound as a brown oil (14 mg) in the form of the trifluoroacetate salt. MS m/z 357 [M+H]$^+$.

Intermediate 14

5-(Benzyloxy)-6-methoxy-1-(phenylsulfonyl)-1H-indole

3 M NaOH (5 mL, 15 mmol) was added to a solution of 5-(benzyloxy)-6-methoxy-indole (1.0 g, 3.9 mmol), tetrabutylammonium hydrogen sulfate (0.400 g, 1.18 mmol) and benzenesulfonyl chloride (1.04 g, 5.92 mmol) in DCM (25 mL). The mixture was stirred overnight at room temperature and diluted with DCM and water. The organic phase was washed with water (1×), dried (MgSO$_4$) and evaporated. The crude product was purified through a plug of silica gel using DCM as the eluent to give the title compound (1.1 g) as a white solid. MS m/z 394 [M+H]$^+$.

Intermediate 15

6-Methoxy-1-(phenylsulfonyl)-1H-indol-5-ol

To a suspension of 5-(benzyloxy)-6-methoxy-1-(phenylsulfonyl)-1H-indole (Intermediate 14, 6.6 g, 17 mmol) and Pd/C 10 wt. % (2.0 g, 1.9 mmol) in EtOH (30 mL) were cyclohexene (9 mL) and conc. HCl (9 mL) added. The reaction mixture was heated at 150° C. for 5 minutes in a microwave heater. The Pd/C was filtered off and the solvent was removed under reduced pressure to afford the title compound (5.0 g) as a black gum. MS m/z 304 [M+H]$^+$.

Intermediate 16

4-{[(2-Hydroxyethyl)(methyl)amino]methyl}-6-methoxy-1-(phenylsulfonyl)-1H-indol-5-ol To 2-(methylamino)ethanol (0.37 g, 4.9 mmol) and paraformaldehyde (0.15 g, 4.9 mmol) was ethanol (5 mL) added. The reaction mixture was heated at 65° C. for 5 minutes and a clear solution was formed. 6-methoxy-1-(phenylsulfonyl)-1H-indol-5-ol (Intermediate 15, 0.75 g, 2.5 mmol) in EtOH (10 mL) was added in one portion. The mixture was stirred for 2 hours at 70° C. The solvent was removed under reduced pressure and the crude material was dissolved in DCM and was washed with brine. The organic layer was collected and dried (MgSO$_4$) to give the title compound (400 mg). MS m/z 391 [M+H]$^+$.

Example 48

6-Methoxy-2-methyl-8-(phenylsulfonyl)-1,3,4,8-tetrahydro-2H-[1,4]oxazepino[6,7-e]indole THF (15 mL) was added to a pyrex tube charged with 4-{[(2-hydroxyethyl)(methyl)amino]methyl}-6-methoxy-1-(phenylsulfonyl)-1H-indol-5-ol (Intermediate 16, 1.02 mmol, 400 mg), triphenylphosphine (2.05 mmol, 537 mg) and 1,1'-azobis(N,N-dimethylformamide) (2.05 mmol, 353 mg). The reaction mixture was heated at 150° C. for 90 minutes in a microwave heater. The crude product was purified by preparative HPLC (XTerra C18, 50 mM NH$_4$HCO$_3$ pH 10-CH$_3$CN) to give the title compound (137 mg). MS m/z 373 [M+H]$^+$.

Example 49

8-(Phenylsulfonyl)-1,3,4,8-tetrahydro-2H-[1,4]oxazepino[6,7-e]indole

1-Chloroethyl chloroformate (1.0 mL, 7.0 mmol) was added to a solution of 2-methyl-8-(phenylsulfonyl)-1,3,4,8-tetrahydro-2H-[1,4]oxazepino[6,7-e]indole (Example 5, 0.15 g, 0.44 mmol), and 1,8-bis-(dimethylamino)-naphthalene (proton sponge) (0.056 g, 0.26 mmol) in DCM (10 mL) and the mixture was stirred at 43° C. for 1 hour. 1.0 M HCl in diethylether (2.5 mL, 2.5 mmol) was added and the mixture was evaporated. The residue was dissolved in dry MeOH (10 mL) and heated at 78° C. for 30 minutes and evaporated. The residue was dissolved in DCM and washed with water, brine, and the organic phase was dried (MgSO$_4$) and evaporated. The crude product was purified by flash chromatography on silica gel using MeOH:DCM:NEt$_3$ (5:94:1) as the eluent to give the title compound (11 mg) as a light pink solid. MS m/z 329 [M+H]$^+$.

Intermediate 17 tert-Butyl 8-(phenylsulfonyl)-1,3,4,8-tetrahydro-2H-[1,4]oxazepino[6,7-e]indole-2-carboxylate 8-(Phenylsulfonyl)-1,3,4,8-tetrahydro-2H-[1,4]oxazepino[6,7-e]indole (Example 49, 0.60 g, 1.8 mmol) was dissolved in DCM (20 mL) and di-tert-butyl dicarbonate (0.48 g, 2.2 mmol) was added all in one portion. The mixture was stirred for 1 hour at room temperature, washed with water and the organic phase was dried (MgSO$_4$) and evaporated. The crude product was purified through a plug of silica gel using DCM as the eluent to give the title compound (0.75 g) as a colorless liquid. MS m/z 373 [M+H−tert-Butyl])$^+$.

Example 50

2-(2-Fluoroethyl)-8-(phenylsulfonyl)-1,3,4,8-tetrahydro-2H-[1,4]oxazepino[6,7-e]indole tert-Butyl 8-(phenylsulfonyl)-1,3,4,8-tetrahydro-2H-[1,4] oxazepino[6,7-e]indole-2-carboxylate (Intermediate 17, 16 mg, 0.040 mmol) was dissolved in DCM (1 mL) and TFA (0.5 mL) was added. The reaction mixture was heated to reflux, and immediately allowed to cool to room temperature. The solution was evaporated and the residue was dissolved in DMF (0.5 mL). Triethylamine (0.011 mL, 0.080 mmol) was added and the reaction mixture was stirred for 5 minutes before 1-fluoro-2-iodoethane (0.063 mL, 0.080 mmol) was added. The solution was stirred at 60° C. overnight. The solution was evaporated and the crude product was purified by preparative HPLC (XTerra C18, 50 mM NH$_4$HCO$_3$ pH 10-CH$_3$CN) to give the title compound (6.9 mg). MS m/z 375 [M+H]$^+$.

Intermediate 18 tert-Butyl 1,3,4,8-tetrahydro-2H-[1,4]oxazepino[6,7-e]indole-2-carboxylate

Di-tert-butyl dicarbonate (69 mg, 0.32 mmol) and 4-dimethylaminopyridine (3.0 mg, 0.020 mmol) were added to a solution of 8-(phenylsulfonyl)-1,3,4,8-tetrahydro-2H-[1,4] oxazepino[6,7-e]indole (Example 49, 80.0 mg, 0.244 mmol) in DCM (3 mL). The reaction was stirred for 1 hour at room temperature, diluted with DCM and washed with 0.5 N HCl. The organic phase was dried (MgSO$_4$) and evaporated. The residue was dissolved in EtOH (3 mL) and a solution of 4N NaOH (0.3 mL, 1.2 mmol) was added and the mixture was heated at 75° C. for 3 hours and evaporated. The residue was dissolved in DCM and washed with saturated aqueous NaHCO$_3$, dried (MgSO$_4$) and evaporated. The crude product was purified through a plug of silica gel using 2.5% MeOH in DCM as the eluent to give the title compound (49 mg) as a white solid. MS m/z 233 [M+H−tert-Butyl]$^+$.

Example 51

8-[(2-Methoxy-5-methylphenyl)sulfonyl]-1,3,4,8-tetrahydro-2H-[1,4]oxazepino[6,7-e]indole Sodium hydride (60% in mineral oil, 16.6 mg, 0.312 mmol) was added to a solution of tert-butyl 1,3,4,8-tetrahydro-2H-[1,4]oxazepino[6,7-e]indole-2-carboxylate (Intermediate 18, 0.060 g, 0.21 mmol) in DMF (3 mL). The mixture was stirred for 20 minutes at room temperature before (2-methoxy-5-methylphenyl)sulfonyl chloride (69 mg, 0.31 mmol) was added. The mixture was stirred for 20 minutes and diluted with water and DCM. The aqueous phase was adjusted to pH 3 with 1 M HCl and extracted with DCM (2×). The combined organics were evaporated to approximately 5 mL. TFA (2 mL) was added and the mixture was stirred at room temperature for 3 hours and the reaction mixture was evaporated. The residue was dissolved in DCM and triethylamine (1 mL) was added and the mixture was evaporated. The crude product was purified by flash chromatography on silica gel using MeOH:DCM:NEt$_3$ (3:96:1) as the eluent to give a white solid which was suspended in diethylether and filtered. The white powder was washed with cold diethylether (2×) and dried in vacuo to give the title compound (65 mg). MS m/z 373 [M+H]$^+$.

Example 52

8-[(2,4-Dichlorophenyl)sulfonyl]-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.05 mmol), NaH (60% in mineral oil, 6.4 mg, 0.10 mmol) and dry DMF (0.2 mL) were shaken at room temperature for 10 minutes. 2,4-Dichlorobenzenesulfonyl chloride (25 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M NH$_3$ in MeOH (1 mL, 1 mmol) and MeOH (1 mL). The crude product was purified by preparative HPLC (XTerra C18, 50 mM NH$_4$HCO$_3$ pH 10-CH$_3$CN) to give the title compound as an off-white solid (1.9 mg). MS m/z 398 [M+H]$^+$.

Example 53

8-{[3-(Trifluoromethyl)phenyl]sulfonyl}-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.05 mmol), NaH (60% in mineral oil, 6.4 mg, 0.10 mmol) and dry DMF (0.2 mL) were shaken at room temperature for 10 minutes. 3-(Trifluoromethyl)benzenesulfonyl chloride (24 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M NH$_3$ in MeOH (1 mL, 1 mmol) and MeOH (1 mL). The crude product was purified by preparative HPLC (XTerra C18, 50 mM NH$_4$HCO$_3$ pH 10-CH$_3$CN) to give the title compound (2.7 mg) as an off-white solid. MS m/z 397 [M+H]$^+$.

Example 54

8-[(3,4-dimethoxyphenyl)sulfonyl]-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.05 mmol), NaH (60% in mineral oil, 6.4 mg, 0.10 mmol) and dry DMF (0.2 mL) were shaken at room temperature for 10 minutes. 3,4-Dimethoxybenzenesulfonyl chloride (24 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M NH$_3$ in MeOH (1 mL, 1 mmol) and MeOH (1 mL). The crude product was purified by preparative HPLC (XTerra C18, 50 mM NH$_4$HCO$_3$ pH 10-CH$_3$CN) to give the title compound as an off-white solid (6.2 mg). MS m/z 389 [M+H]$^+$.

Example 55

8-(2-Naphthylsulfonyl)-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.050 mmol), NaH (60% in mineral oil, 6.4 mg, 0.10 mmol) and dry DMF (0.2 mL) were shaken at room temperature for 10 minutes. Naphthalene-2-sulfonyl chloride (23 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M NH$_3$ in MeOH (1 mL, 1 mmol) and MeOH (1 mL). The crude product was purified by preparative HPLC (XTerra C18, 50 mM NH$_4$HCO$_3$ pH 10-CH$_3$CN) to give the title compound as an off-white solid (5.2 mg). MS m/z 379 [M+H]$^+$.

Example 56

8-[(2-Methoxy-4-methylphenyl)sulfonyl]-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.050 mmol), NaH (60% in mineral oil, 6.4 mg, 0.10 mmol) and dry DMF (0.2 mL) were shaken at room temperature for 10 minutes. 2-Methoxy-4-methylbenzenesulfonyl chloride (22 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M NH₃ in MeOH (1 mL, 1 mmol) and MeOH (1 mL). The crude product was purified by preparative HPLC (XTerra C18, 50 mM NH₄HCO₃ pH 10-CH₃CN) to give the title compound as an off-white solid (7.8 mg). MS m/z 373 [M+H]⁺.

Example 57

8-[(4-Propylphenyl)sulfonyl]-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.050 mmol), NaH (60% in mineral oil, 6.4 mg, 0.10 mmol) and dry DMF (0.2 mL) were shaken at room temperature for 10 minutes. 4-Propylbenzenesulfonyl chloride (22 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M NH₃ in MeOH (1 mL, 1 mmol) and MeOH (1 mL). The crude product was purified by preparative HPLC (XTerra C18, 50 mM NH₄HCO₃ pH 10-CH₃CN) to give the title compound (12.8 mg). MS m/z 371 [M+H]⁺.

Example 58

8-[(4-Isopropylphenyl)sulfonyl]-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.050 mmol), NaH (60% in mineral oil, 6.4 mg, 0.10 mmol) and dry DMF (0.2 mL) were shaken at room temperature for 10 minutes. 4-Isopropylbenzenesulfonyl chloride (22 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M NH₃ in MeOH (1 mL, 1 mmol) and MeOH (1 mL). The crude product was purified by preparative HPLC (XTerra C18, 50 mM NH₄HCO₃ pH 10-CH₃CN) to give the title compound as an off-white solid (2.9 mg). MS m/z 371 [M+H]⁺.

Example 59

8-(1-Benzofuran-2-ylsulfonyl)-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.050 mmol), NaH (60% in mineral oil, 6.4 mg, 0.10 mmol) and dry DMF (0.2 mL) were shaken at room temperature for 10 minutes. 1-Benzofuran-2-sulfonyl chloride (22 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M NH₃ in MeOH (1 mL, 1 mmol) and MeOH (1 mL). The crude product was purified by preparative HPLC (XTerra C18, 50 mM NH₄HCO₃ pH 10-CH₃CN) to give the title compound as an off-white solid (0.4 mg). MS m/z 369 [M+H]⁺.

Example 60

8-[(2,5-Dimethyl-3-thienyl)sulfonyl]-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.050 mmol), NaH (60% in mineral oil, 6.4 mg, 0.10 mmol) and dry DMF (0.2 mL) were shaken at room temperature for 10 minutes. 2,5-Dimethylthiophene-3-sulfonyl chloride (21 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M NH₃ in MeOH (1 mL, 1 mmol) and MeOH (1 mL). The crude product was purified by preparative HPLC (XTerra C18, 50 mM NH₄HCO₃ pH 10-CH₃CN) to give the title compound as an off-white solid (3.2 mg). MS m/z 363 [M+H]⁺.

Example 61

8-[(3-Fluoro-4-methylphenyl)sulfonyl]-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.050 mmol), NaH (60% in mineral oil, 6.4 mg, 0.10 mmol) and dry DMF (0.2 mL) were shaken at room temperature for 10 minutes. 3-Fluoro-4-methylbenzenesulfonyl chloride (21 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M NH₃ in MeOH (1 mL, 1 mmol) and MeOH (1 mL). The crude product was purified by preparative HPLC (XTerra C18, 50 mM NH₄HCO₃ pH 10-CH₃CN) to give the title compound as an off-white solid (1.4 mg). MS m/z 361 [M+H]⁺.

Example 62

8-[(4-Methoxyphenyl)sulfonyl]-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.050 mmol), NaH (60% in mineral oil, 6.4 mg, 0.10 mmol) and dry DMF (0.2 mL) were shaken at room temperature for 10 minutes. 4-Methoxybenzenesulfonyl chloride (21 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M NH₃ in MeOH (1 mL, 1 mmol) and MeOH (1 mL). The crude product was purified by preparative HPLC (XTerra C18, 50 mM NH₄HCO₃ pH 10-CH₃CN) to give the title compound as an off-white solid (5.5 mg). MS m/z 359 [M+H]⁺.

Example 63

8-[(2,5-Dimethyl-3-furyl)sulfonyl]-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.050 mmol), NaH (60% in mineral oil, 6.4 mg, 0.10 mmol) and dry DMF (0.2 mL) were shaken at room temperature for 10 minutes. 2,5-Dimethylfuran-3-sulfonyl chloride (19 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M $NH_3$ in MeOH (1 mL, 1 mmol) and MeOH (1 mL). The crude product was purified by preparative HPLC (XTerra C18, 50 mM $NH_4HCO_3$ pH 10-$CH_3CN$) to give the title compound as an off-white solid (5.2 mg). MS m/z 347 $[M+H]^+$.

Example 64

8-[(2-Methylphenyl)sulfonyl]-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.050 mmol), NaH (60% in mineral oil, 6.4 mg, 0.10 mmol) and dry DMF (0.2 mL) were shaken at room temperature for 10 minutes. 2-Methylbenzenesulfonyl chloride (19 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M $NH_3$ in MeOH (1 mL, 1 mmol) and MeOH (1 mL). The crude product was purified by preparative HPLC (XTerra C18, 50 mM $NH_4HCO_3$ pH 10-$CH_3CN$) to give the title compound as an off-white solid (5.0 mg). MS m/z 343 $[M+H]^+$.

Example 65

8-[(4-Methylphenyl)sulfonyl]-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.050 mmol), NaH (60% in mineral oil, 6.4 mg, 0.10 mmol) and dry DMF (0.2 mL) were shaken at room temperature for 10 minutes. 4-Methylbenzenesulfonyl chloride (19 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M $NH_3$ in MeOH (1 mL, 1 mmol) and MeOH (1 mL). The crude product was purified by preparative HPLC (XTerra C18, 50 mM $NH_4HCO_3$ pH 10-$CH_3CN$) to give the title compound as an off-white solid (4.9 mg). MS m/z 343 $[M+H]^+$.

Example 66

8-(2-Thienylsulfonyl)-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.050 mmol), NaH (60% in mineral oil, 6.4 mg, 0.10 mmol) and dry DMF (0.2 mL) were shaken at room temperature for 10 minutes. Thiophene-2-sulfonyl chloride (18 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M $NH_3$ in MeOH (1 mL, 1 mmol) and MeOH (1 mL). The crude product was purified by preparative HPLC (XTerra C18, 50 mM $NH_4HCO_3$ pH 10-$CH_3CN$) to give the title compound as an off-white solid (10.2 mg). MS m/z 335 $[M+H]^+$.

Example 67

8-{[2-(Trifluoromethoxy)phenyl]sulfonyl}-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.050 mmol), NaH (60% in mineral oil, 6.4 mg, 0.10 mmol) and dry DMF (0.2 mL) were shaken at room temperature for 10 minutes. 2-(Trifluoromethoxy)benzenesulfonyl chloride (26 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M $NH_3$ in MeOH (1 mL, 1 mmol) and MeOH (1 mL). The crude product was purified by preparative HPLC (XTerra C18, 50 mM $NH_4HCO_3$ pH 10-$CH_3CN$) to give the title compound as an off-white solid (1.0 mg). MS m/z 413 $[M+H]^+$.

Example 68

8-(Biphenyl-3-ylsulfonyl)-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.050 mmol), NaH (60% in mineral oil, 6.4 mg, 0.10 mmol) and dry DMF (0.2 mL) were shaken at room temperature for 10 minutes. Biphenyl-3-sulfonyl chloride (25 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M $NH_3$ in MeOH (1 mL, 1 mmol) and MeOH (1 mL). The crude product was purified by preparative HPLC (XTerra C18, 50 mM $NH_4HCO_3$ pH 10-$CH_3CN$) to give the title compound as an off-white solid (2.0 mg). MS m/z 405 $[M+H]^+$.

Example 69

8-[{2-(Trifluoromethyl)phenyl]sulfonyl}-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.050 mmol), NaH (60% in mineral oil, 6.4 mg, 0.10 mmol) and dry DMF (0.2 mL) were shaken at room temperature for 10 minutes. 2-(Trifluoromethyl)benzenesulfonyl chloride (24 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M $NH_3$ in MeOH (1 mL, 1 mmol) and MeOH (1 mL). The crude product was purified by preparative HPLC (XTerra C18, 50 mM $NH_4HCO_3$ pH 10-$CH_3CN$) to give the title compound as an off-white solid (3.3 mg). MS m/z 397 $[M+H]^+$.

Example 70

8-(1-Benzothien-2-ylsulfonyl)-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.050 mmol), NaH (60% in mineral oil, 6.4 mg, 0.10 mmol) and dry DMF (0.2 mL) were shaken at room temperature for 10 minutes. 1-Benzothiophene-2-sulfonyl chloride (23 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M $NH_3$ in MeOH (1 mL, 1 mmol) and MeOH (1 mL). The crude product was purified by preparative HPLC (XTerra C18, 50 mM $NH_4HCO_3$ pH 10-$CH_3CN$) to give the title compound as an off-white solid (1.9 mg). MS m/z 385 $[M+H]^+$.

Example 71

8-(1-Naphthylsulfonyl)-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.050 mmol), NaH (60% in mineral oil, 6.4 mg, 0.10 mmol) and dry DMF (0.2 mL) were shaken at room temperature for 10 minutes. Naphthalene-1-sulfonyl chloride (23 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M $NH_3$ in MeOH (1 mL, 1 mmol) and MeOH (1 mL). The crude product was purified by preparative HPLC (XTerra C18, 50 mM $NH_4HCO_3$ pH 10-$CH_3CN$) to give the title compound as an off-white solid (1.5 mg). MS m/z 379 $[M+H]^+$.

Example 72

8-[(5-Fluoro-2-methylphenyl)sulfonyl]-1,3,4,8-tetrahydro-2H-[1,4]oxazepino[6,7-e]indole tert-Butyl 1,3,4,8-tetrahydro-2H-[1,4]oxazepino[6,7-e]indole-2-carboxylate (Intermediate 18, 14 mg, 0.050 mmol), NaH (60% in mineral oil, 6.4 mg, 0.10 mmol) and dry DMF (0.2 mL) were shaken at room temperature for 10 minutes. 5-Fluoro-2-methylbenzenesulfonyl chloride (21 mg, 0.10 mmol, in 0.15 mL of dry DMF) was added to the solution. The reaction mixture was shaken at room temperature for another 20 minutes and a mixture of MeOH/1 M HCl (3:1, 1 mL) was added. The reaction mixture was stirred overnight and evaporated. The residue was dissolved in 1 M $NH_3$ in MeOH (1 mL, 1 mmol) and MeOH (1 mL). The crude product was purified by preparative HPLC (XTerra C18, 50 mM $NH_4HCO_3$ pH 10-$CH_3CN$) to give the title compound as an off-white solid (2.7 mg). MS m/z 361 $[M+H]^+$.

Intermediate 19 tert-Butyl ((1R)-2-{[4-formyl-1-(phenylsulfonyl)-1H-indol-5-yl]oxy}-1-methylethyl)carbamate 1,1'-Azobis(N,N-dimethylformamide) (201 mg, 1.16 mmol) was added to a solution of 5-hydroxy-1-(phenylsulfonyl)-1H-indole-4-carbaldehyde (Intermediate 10, 0.070 g, 0.23 mmol), R-(+)-2-(tert-butoxycarbonylamino)-1-propanol (81.6 mg, 0.465 mmol) and triphenylphosphine (302 mg, 1.16 mmol) in DCM (14 mL). The mixture was stirred at 45° C. for 2 days and then at room temperature for 2 days. The mixture was diluted with 0.5 N NaOH and DCM. The organic layer was separated, dried ($MgSO_4$) and evaporated. The crude product was purified by flash chromatography using 1% to 2.5% MeOH in DCM to give the title compound (70 mg) as a white solid. MS m/z 359 $[M+H-Boc]^+$.

Example 73

(3R)-3-Methyl-8-(phenylsulfonyl)-1,3,4,8-tetrahydro-2H-[1,4]oxazepino[6,7-e]indole tert-Butyl ((1R)-2-{[4-formyl-1-(phenylsulfonyl)-1H-indol-5-yl]oxy}-1-methylethyl)carbamate (Intermediate 19, 0.040 g, 0.087 mmol) was dissolved in DCM (2 mL) and TFA (0.5 mL) was added. The mixture was stirred for 1 hour at room temperature and evaporated. The residue was dissolved in THF (2 mL) and sodium triacetoxyborohydride (37.0 mg, 0.176 mmol) was added. The mixture was stirred for 1 hour, evaporated and purified by flash chromatography using 2.5%-5% MeOH in DCM as the eluent to give the title compound (25 mg) as a white solid. MS m/z 343 $[M+H]^+$.

Example 74

(3R)-2,3-Dimethyl-8-(phenylsulfonyl)-1,3,4,8-tetrahydro-2H-[1,4]oxazepino[6,7-e]indole Sodium triacetoxyborohydride (7.5 mg, 0.040 mmol) was added to a solution of (3R)-3-methyl-8-(phenylsulfonyl)-1,3,4,8-tetrahydro-2H-[1,4]oxazepino[6,7-e]indole (Example 73, 0.010 g, 0.029 mmol) and formaldehyde (37 wt. % in $H_2O$, 0.020 mL, 0.25 mmol) in THF (1 mL). The mixture was stirred for 20 minutes, evaporated and the crude material was purified by preparative HPLC (ACE C8, 0.1% TFA-$CH_3CN$) to give the title compound as a white solid (4 mg) in the form of the trifluoroacetate salt. MS m/z 357 $[M+H]^+$.

Example 75

6-Methoxy-8-(phenylsulfonyl)-1,3,4,8-tetrahydro-2H-[1,4]oxazepino[6,7-e]indole To 6-methoxy-2-methyl-8-(phenylsulfonyl)-1,3,4,8-tetrahydro-2H-[1,4]oxazepino[6,7-e]indole (Example 48, 0.030 g, 0.081 mmol), 1,8-Bis(dimethylamino)-naphthalene (0.010 g, 0.048 mmol) and 1-chloroethyl chloroformate (25 mg, 0.18 mmol) were added followed by dry DCM (2 mL). The reaction mixture was stirred at room temperature for 30 minutes. The solvent was removed under reduced pressure and the crude material was dissolved in dry MeOH (3 mL). The reaction mixture was heated at reflux for 2 hours, cooled and the crude product was purified by preparative HPLC (XTerra C18, 50 mM $NH_4HCO_3$ pH 10-$CH_3CN$) to give the title compound (3 mg). MS m/z 359 $[M+H]^+$.

Example 76

9-Methyl-8-(phenylsulfonyl)-1,3,4,8-tetrahydro-2H-[1,4]oxazepino[6,7-e]indole trifluoroacetate tert-Butyl 8-(phenylsulfonyl)-1,3,4,8-tetrahydro-2H-[1,4]oxazepino[6,7-e]indole-2-carboxylate (Intermediate 17, 0.020 g, 0.050 mmol) was dissolved in THF (1 mL) and cooled on an ethanol/CO$_2$(s) bath. BuLi (2.5 M in hexanes, 0.054 mL, 0.15 mmol) was added and the solution was stirred at −78° C. for 27 minutes. MeI (0.012 mL, 0.20 mmol) was added. The temperature was allowed to rise to room temperature overnight. Water was added and the solution was extracted with EtOAc. The organic phase was evaporated and the residue was dissolved in DCM (1 mL). TFA (0.5 mL) was added and the solution was heated at reflux and immediately allowed to cool to room temperature. The reaction mixture was evaporated to give the title compound (21 mg). MS m/z 343 [M+H]$^+$.

Example 77

10-Chloro-8-(phenylsulfonyl)-1,3,4,8-tetrahydro-2H-[1,4]oxazepino[6,7-e]indole trifluoroacetate tert-Butyl 8-(phenylsulfonyl)-1,3,4,8-tetrahydro-2H-[1,4]oxazepino[6,7-e]indole-2-carboxylate (Intermediate 17, 15 mg, 0.035 mmol) was dissolved in CHCl$_3$ (2 mL) and N-chlorosuccinimide (7.0 mg, 0.053 mmol) was added. The mixture was heated at 70° C. overnight. The mixture was cooled to room temperature, TFA (1 mL) was added and the mixture was stirred for 10 minutes and evaporated. The crude material was purified by preparative HPLC (ACE C8, 0.1% TFA-CH$_3$CN) to give the title compound as a light yellow solid (4.1 mg) in the form of the trifluoroacetate salt. MS m/z 363 [M+H]$^+$.

Intermediate 20 tert-Butyl 10-chloro-1,3,4,8-tetrahydro-2H-[1,4]oxazepino[6,7-e]indole-2-carboxylate N-chlorosuccinimide (0.23 g, 0.54 mmol) was added to a solution of tert-butyl 8-(phenylsulfonyl)-1,3,4,8-tetrahydro-2H-[1,4]oxazepino[6,7-e]indole-2-carboxylate (Intermediate 17, 0.23 g, 0.54 mmol) in chloroform (4 mL) and heated at 130° C. for 40 minutes in a microwave heater. The mixture was evaporated and purified by flash chromatography on silica gel using MeOH and DCM (1:99) as the eluent to give 167 mg of tert-butyl 10-chloro-8-(phenylsulfonyl)-1,3,4,8-tetrahydro-2H-[1,4]oxazepino[6,7-e]indole-2-carboxylate. This intermediate (167 mg, 0.360 mmol) was dissolved in EtOH (20 mL) and a solution of 10 M KOH (0.2 mL, 2 mmol) was added. The mixture was heated at 65° C. for 20 minutes and the reaction mixture was evaporated and purified by preparative HPLC (ACE C8, 0.1% TFA-CH3CN) to give an off-white solid (40 mg) in the form of the trifluoroacetate salt. MS m/z 223 [M+H−Boc]$^+$.

Example 78

10-Chloro-8-[(4-fluorophenyl)sulfonyl]-1,3,4,8-tetrahydro-2H-[1,4]oxazepino[6,7-e]indole trifluoroacetate tert-Butyl 10-chloro-1,3,4,8-tetrahydro-2H-[1,4]oxazepino[6,7-e]indole-2-carboxylate (Intermediate 20, 10 mg, 0.031 mmol) was dissolved in dry DMF (1 mL) and sodium hydride (60% in mineral oil, 2.5 mg, 0.062 mmol) was added all in one portion. The mixture was stirred for 10 minutes at room temperature before 4-fluorobenzenesulfonyl chloride (12 mg, 0.062 mmol) was added. The reaction mixture was stirred for 10 minutes, and TFA (1 mL) was added dropwise. The reaction mixture was heated at 50° C. overnight and evaporated. The crude material was purified by preparative HPLC (ACE C8, 0.1% TFA-CH3CN) to give the title compound as a white solid (9.8 mg) in the form of the trifluoroacetate salt. MS m/z 381 [M+H]$^+$.

Example 79

3-[(10-Chloro-1,2,3,4-tetrahydro-8H-[1,4]oxazepino[6,7-e]indol-8-yl)sulfonyl]benzonitrile trifluoroacetate tert-Butyl 10-chloro-1,3,4,8-tetrahydro-2H-[1,4]oxazepino[6,7-e]indole-2-carboxylate (Intermediate 20, 10 mg, 0.031 mmol) was dissolved in DMF (1 mL) and sodium hydride (60% in mineral oil, 2.5 mg, 0.062 mmol) was added. The mixture was stirred for 10 minutes at room temperature before 3-cyanobenzene-1-sulfonyl chloride (13 mg, 0.062 mmol) was added. The reaction mixture was stirred for 20 minutes before TFA (2 mL) was added and the mixture was heated at 50° C. overnight. The reaction mixture was evaporated and the crude material was purified by preparative HPLC (ACE C8, 0.1% TFA-CH3CN) to give the title compound as an off-white solid (1.3 mg) in the form of the trifluoroacetate salt. MS m/z 388 [M+H]$^+$.

Example 80

10-Chloro-8-(pyridin-3-ylsulfonyl)-1,3,4,8-tetrahydro-2H-[1,4]oxazepino[6,7-e]indole bis(trifluoroacetate)

Preparation of the free base: Pyridine-3-sulfonyl chloride hydrochloride (20 mg, 0.093 mmol) was dissolved in a mixture of dichloromethane and aqueous saturated NaHCO$_3$ and the organic layer was dried (MgSO$_4$) and evaporated to give pyridine-3-sulfonyl chloride. tert-Butyl 10-chloro-1,3,4,8-tetrahydro-2H-[1,4]oxazepino[6,7-e]indole-2-carboxylate (Intermediate 20, 10 mg, 0.031 mmol) was dissolved in DMF (1 mL) and sodium hydride (60% in mineral oil, 2.5 mg, 0.062 mmol) was added. The mixture was stirred for 10 minutes before pyridine-3-sulfonyl chloride (0.093 mmol) in DMF (1 mL) was added. The reaction mixture was stirred at room temperature for 10 minutes before TFA (2 mL) was added and the mixture was heated at 50° C. overnight. The reaction mixture was evaporated and the crude material was purified by preparative HPLC (ACE C8, 0.1% TFA-CH3CN) to give the title compound as a white solid (2.6 mg) in the form of the trifluoroacetate salt. MS m/z 364 [M+H]$^+$.

Example 81

8-[(2-Chlorophenyl)sulfonyl]-1,3,4,8-tetrahydro-2H-[1,4]oxazepino[6,7-e]indole trifluoroacetate DMF (1 mL) was added to a mixture of tert-butyl 1,3,4,8-tetrahydro-2H-[1,4]oxazepino[6,7-e]indole-2-carboxylate (Intermediate 18, 10.0 mg, 0.035 mmol) and 60% NaH (5.56 mg, 0.139 mmol). The reaction mixture was stirred for 10 minutes at room temperature before 2-chlorophenylsulfonyl chloride (11 mg, 0.052 mmol) was added all in one portion. After 30 minutes TFA (1 mL) was added and the mixture was stirred for 10 minutes and evaporated. The crude material was purified by preparative HPLC (ACE C8, 0.1% TFA-CH$_3$CN) to give the title compound as a white solid (9.6 mg) in the form of the trifluoroacetate salt. MS m/z 363 [M+H]$^+$.

Intermediate 21

4-Bromo-1-(phenylsulfonyl)-1H-indol-5-ol

NBS (32.6 mg, 0.180 mmol) in DMF (1 mL) was added to a solution of 1-(phenylsulfonyl)-1H-indol-5-ol (Intermediate 8, 50.0 mg, 0.183 mmol) in DMF (1 mL) at room temperature. The mixture was stirred for 30 minutes and diluted with water and diethylether and transferred to a separation funnel. The organic phase was washed with water (3×), dried (MgSO$_4$) and evaporated. The crude product was purified by flash chromatography using 10% pentane in DCM as the eluent to give the title compound (50 mg) as a white solid. MS m/z 352/354 [M+H]$^+$.

Intermediate 22

4-Bromo-1-(phenylsulfonyl)-1H-indol-5-yl acetate

Triethylamine (0.29 g, 2.8 mmol) was added to a solution of 4-bromo-1-(phenylsulfonyl)-1H-indol-5-ol (Intermediate 21, 0.67 g, 1.9 mmol) and acetyl chloride (0.22 g, 2.8 mmol) in THF (10 mL). The mixture was stirred for 10 minutes at room temperature and evaporated. The residue was partitioned between DCM and saturated aqueous NaHCO$_3$. The reaction mixture was washed with saturated aqueous NaHCO$_3$, and the organic phase was dried (MgSO$_4$) and evaporated to give the title compound (0.6 g) as a red solid. MS m/z 394/396 [M+H]$^+$.

Intermediate 23

1-[5-Hydroxy-1-(phenylsulfonyl)-1H-indol-4-yl]ethanone

4-Bromo-1-(phenylsulfonyl)-1H-indol-5-yl acetate (Intermediate 22, 0.57 g, 1.5 mmol) was dissolved in toluene (10 mL) under an atmosphere of N$_2$ gas and 1-ethoxyvinyl-tributylstannane (0.78 g, 2.2 mmol) and bis-(triphenylphosphin)-palladium(II)-chloride (50.8 mg, 0.072 mmol) were added and the mixture was heated at 110° C. After 30 minutes additional catalyst (25 mg, 0.036 mmol) was added and the mixture was heated at 110° C. for an additional 3 hours, cooled and filtered through a plug of silica gel using EtOAc as the eluent. The filtrate was washed with 1 M HCl and saturated aqueous brine, dried over (MgSO$_4$) and evaporated. The crude product was dissolved in THF/1 M HCl 2:1 (40 mL) and stirred for 30 minutes at room temperature. The mixture was evaporated and partitioned between water and DCM. The organic phase was dried (MgSO$_4$) and evaporated. The crude material was purified by flash chromatography on silica gel using 10% petroleum ether in DCM as the eluent to give the title compound (100 mg) as a light yellow solid. MS m/z 316 [M+H]$^+$.

Example 82

1-Methyl-8-(phenylsulfonyl)-1,3,4,8-tetrahydro-2H-[1,4]oxazepino[6,7-e]indole 1,1'-Azobis(N,N-dimethylformamide) (73 mg, 0.43 mmol) was added to a solution of 1-[5-hydroxy-1-(phenylsulfonyl)-1H-indol-4-yl]ethanone (Intermediate 23, 67 mg, 0.21 mmol), tert-butyl N-(2-hydroxy-ethyl)carbamate (0.14 g, 0.85 mmol) and triphenylphosphine (112 mg, 0.430 mmol) in DCM (5 mL). The mixture was heated at 43° C. for 1 hour and additional 1,1'-azobis(N,N-dimethylformamide) (0.030 g, 0.17 mmol) was added and the mixture was heated at 43° C. for an additional 2 hours. The mixture was cooled to room temperature and TFA (2.5 mL) was added and the mixture was stirred for 1 hour and evaporated. The residue was partitioned between DCM and 1 M NaOH. The organic phase was dried (MgSO$_4$) and evaporated. The crude product was purified by flash chromatography using 5% MeOH in DCM as the eluent to give 75 mg of 1-methyl-8-(phenylsulfonyl)-3,8-dihydro-4H-[1,4]oxazepino[6,7-e]indole. Acetic acid (132 mg, 2.20 mmol) was added to a solution of the 1-methyl-8-(phenylsulfonyl)-3,8-dihydro-4H-[1,4]oxazepino[6,7-e]indole (75.0 mg, 0.22 mmol) in DCM (10 mL) and the mixture was allowed to stir for 10 minutes at room temperature before sodium triacetoxyborohydride (0.070 g, 0.33 mmol) was added all in one portion. The mixture was stirred for 30 minutes and transferred to a separation funnel and washed with 1 M NaOH and brine. The organic phase was dried (MgSO$_4$) and evaporated. The crude product was purified by flash chromatography on silica gel using MeOH:DCM:NEt$_3$ (5:94:1) as the eluent to give the title compound (28 mg) as a white solid. MS m/z 343 [M+H]$^+$.

Example 83

(1S)-1-Methyl-8-(phenylsulfonyl)-1,3,4,8-tetrahydro-2H-[1,4]oxazepino[6,7-e]indole A small sample of racemic 1-methyl-8-(phenylsulfonyl)-1,3,4,8-tetrahydro-2H-[1,4]oxazepino[6,7-e]indole Example 82 was purified by preparative HPLC (Chiracel column OJ-H, 0.46 cm*25 cm, 30:70 i-PrOH: n-hexane) to give the title compound (0.7 mg) as a white solid. MS m/z 343 [M+H]$^+$.

Example 84

(1R)-1-Methyl-8-(phenylsulfonyl)-1,3,4,8-tetrahydro-2H-[1,4]oxazepino[6,7-e]indole A small sample of racemic 1-methyl-8-(phenylsulfonyl)-1,3,4,8-tetrahydro-2H-[1,4]oxazepino[6,7-e]indole Example 82 was purified by preparative HPLC (Chiracel column OJ-H, 0.46 cm*25 cm, 30:70 i-PrOH: n-hexane) to give the title compound (0.7 mg) as a white solid. MS m/z 343 [M+H]$^+$.

Intermediate 24

2-{[1-(Phenylsulfonyl)-1H-indol-5-yl]oxy}ethanamine

To 1-(phenylsulfonyl)-1H-indol-5-ol, (Intermediate 8, 8.0 g, 29 mmol) were 1,1'-azobis(N,N-dimethylformamide) (7.6 g, 44 mmol), triphenylphosphine (15.4 g, 580 mmol), tert-butyl N-(2-hydroxy-ethyl)carbamate (9.4 g, 58 mmol) and DCM (200 mL) added. The reaction mixture was heated at 50° C. for 1.5 hours. The reaction mixture was allowed to cool to room temperature and TFA (50 mL) was added. The reaction mixture was stirred for 3 hours and evaporated. The crude material was purified with flash chromatography on silica gel (DCM:MeOH, 95:5) to give the title compound (9.6 g). MS m/z 317 [M+H]$^+$.

Intermediate 25

N-(2-{[1-(Phenylsulfonyl)-1H-indol-5-yl]oxy}ethyl)acetamide

2-{[1-(Phenylsulfonyl)-1H-indol-5-yl]oxy}ethanamine (Intermediate 24, 9.6 g, 30 mmol) in DCM (100 mL) was treated with triethylamine (12.8 mL, 91.0 mmol) and 4-dimethylaminopyridine (1.9 g, 15 mmol). The solution was cooled to 0° C. and acetyl chloride (4.3 mL, 61 mmol) was added. The reaction mixture was stirred at room temperature for 1 hour and washed with saturated aqueous $NaHCO_3$ (50 mL) and 1 M HCl (2×50 mL). The organic phase was dried ($MgSO_4$) and concentrated in vacuo to give the title compound (10.3 g). MS m/z 359 $[M+H]^+$.

Example 85

1-Methyl-8-(phenylsulfonyl)-3,8-dihydro-4H-[1,4]oxazepino[6,7-e]indole

To N-(2-{[1-(phenylsulfonyl)-1H-indol-5-yl]oxy}ethyl)acetamide (Intermediate 25, 5.0 g, 14 mmol) in acetonitrile (7.5 L) was phosphoryl chloride (100 mL) added and the reaction mixture was heated at reflux overnight. The reaction mixture was allowed to cool to room temperature and the solvent was removed under reduced pressure to give the crude material of the title compound (5.0 g). A small amount of the crude material was purified by preparative HPLC (XTerra C18, 50 mM $NH_4HCO_3$ pH 10-$CH_3CN$) to give the title compound (12 mg). MS m/z 341 $[M+H]^+$.

Intermediate 26

5-Benzyloxy-6-fluoroindole

Prepared according to Eur. Pat. Appl. EP 0 505 322 B1, 1992.

Intermediate 27

N-Benzenesulfonyl-5-benzyloxy-6-fluoroindole

To a stirred solution of 5-benzyloxy-6-fluoroindole (Intermediate 26, 2.0 g, 8.3 mmol) in dry DMF (30 mL) was sodium hydride (60% in mineral oil, 0.35 g, 8.7 mmol) added at 0° C. The solution was stirred for 30 minutes at room temperature and the reaction mixture was cooled to 0° C. and benzenesulfonyl chloride (1.17 mL, 9.12 mmol) was added dropwise. The reaction mixture was kept at 4° C. overnight, and a drop of methanol was added and the solvent was evaporated. The crude material was dissolved in DCM, washed with saturated aqueous $NaHCO_3$, dried over $MgSO_4$, filtered and evaporated. The crude material was purified by flash chromatography on silica gel using DCM as the eluent to give the title compound (2.88 g) as a light yellow oil. MS m/z 382 $[M+H]^+$.

Intermediate 28

6-Fluoro-1-(phenylsulfonyl)-1H-indol-5-ol

Pd/C 10 wt. % (250 mg, 0.236 mmol was added to a solution of N-benzenesulfonyl-5-benzyloxy-6-fluoroindole (Intermediate 27, 250 mg, 6.55 mmol) in ethanol (100 mL). The reaction mixture was stirred under an atmosphere of hydrogen (1 atm) at room temperature for 2 hours, filtered and evaporated. The crude material was purified by flash chromatography on silica gel using 0.5% MeOH/DCM as the eluent to give the title compound (1.79 g) as a white solid. MS m/z 292 $[M+H]^+$.

Intermediate 29

2-{[6-Fluoro-1-(phenylsulfonyl)-1H-indol-5-yl]oxy}ethanamine

To 6-fluoro-1-(phenylsulfonyl)-1H-indol-5-ol (Intermediate 28, 3.0 g, 10 mmol), 1,1'-azobis(N,N (3.5 g, 21 mmol), triphenylphosphine (5.4 g, 21 mmol), tert-butyl N-(2-hydroxy-ethyl)carbamate (3.3 g, 21 mmol) and DCM (20 mL) were added. The mixture was heated at 150° C. for 20 minutes in a microwave heater. The reaction mixture was allowed to cool to room temperature and TFA (20 mL) was added. The reaction mixture was allowed to stir at room temperature for 2 hours. The solvent was removed under reduced pressure and the crude material was filtered through a plug of silica gel using DCM as eluent. The solvent was removed under reduced pressure and the crude material was dissolved in ethyl acetate (10 mL) and the HCl salt of the title compound precipitated when 1 M HCl in diethylether (20 mL) was added. The solid was filtered off, dissolved in DCM (100 mL) and organic phase was washed with saturated aqueous $NaHCO_3$ (40 mL) to give the title compound (2.0 g). MS m/z 335 $[M+H]^+$.

Intermediate 30

N-(2-{[6-fluoro-1-(phenylsulfonyl)-1H-indol-5-yl]oxy}ethyl)acetamide

2-{[6-Fluoro-1-(phenylsulfonyl)-1H-indol-5-yl]oxy}ethanamine (Intermediate 29, 2.0 g 6.0 mmol) in DCM (100 mL) was treated with triethylamine (2.5 mL, 18 mmol) and 4-dimethylaminopyridine (0.37 g, 3.0 mmol). The solution was cooled to 0° C. and treated with acetyl chloride (0.85 mL, 12 mmol). The mixture was stirred at room temperature for 1.5 hours and washed with saturated aqueous $NaHCO_3$ (40 mL) and 0.5 M HCl (40 mL). The organic phase was dried ($MgSO_4$) and concentrated in vacuo to give the title compound (2.0 g). MS m/z 377 $[M+H]^+$.

Intermediate 31

6-Fluoro-1-methyl-8-(phenylsulfonyl)-3,8-dihydro-4H-[1,4]oxazepino[6,7-e]indole

To N-(2-{[6-fluoro-1-(phenylsulfonyl)-1H-indol-5-yl]oxy}ethyl)acetamide (Intermediate 30, 0.020 g, 0.053 mmol) in acetonitrile (20 mL) phosphoryl chloride (0.5 mL) was added and the reaction mixture was heated at 200° C. for 30 minutes in a microwave heater. The crude product was purified by preparative HPLC (XTerra C18, 50 mM $NH_4HCO_3$ pH 10-$CH_3CN$) to give the title compound (1 mg). MS m/z 359 $[M+H]^+$.

Example 86

6-Fluoro-1-methyl-8-(phenylsulfonyl)-1,3,4,8-tetrahydro-2H-[1,4]oxazepino[6,7-e]indole 6-Fluoro-1-methyl-8-(phenylsulfonyl)-3,8-dihydro-4H-[1,4]oxazepino[6,7-e]indole (Intermediate 31, 0.010 g, 0.028 mmol) was dissolved in EtOH (2 mL) and $NaCNBH_3$ (3.5 mg, 0.056 mmol) was added. The reaction mixture was heated at 50° C. for 1 hour. The reaction was quenched by addition of water and the solvent was removed under reduced pressure. The crude product was purified by preparative HPLC (XTerra C18, 50 mM NH₄HCO₃ pH 10-CH₃CN) to give the title compound (1.2 mg). MS m/z 361 [M+H]⁺.

Intermediate 32

2-{[6-Methoxy-1-(phenylsulfonyl)-1H-indol-5-yl]oxy}ethanamine

To 6-methoxy-1-(phenylsulfonyl)-1H-indol-5-ol (Intermediate 15, 2.0 g, 6.6 mmol), 1,1'-azobis(N,N-dimethylformamide) (2.3 g, 13 mmol), triphenylphosphine (3.5 g, 13 mmol), tert-butyl N-(2-hydroxy-ethyl)carbamate (2.1 g, 13 mmol) and DCM (40 mL) were added. The mixture was heated at 150° C. for 20 minutes in a microwave heater. The reaction mixture was allowed to cool to room temperature and TFA (30 mL) was added. The reaction mixture was allowed to stir at room temperature for 30 minutes. The solvent was removed under reduced pressure and the crude material was purified by flash chromatography on silica gel using 5% MeOH in DCM as the eluent to afford the title compound (2.53 g) MS m/z 347 [M+H]⁺.

Intermediate 33

N-(2-{[6-methoxy-1-(phenylsulfonyl)-1H-indol-5-yl]oxy}ethyl)acetamide

2-{[6-Methoxy-1-(phenylsulfonyl)-1H-indol-5-yl]oxy}ethanamine (Intermediate 32, 2.0 g, 5.8 mmol) in DCM (100 mL) was treated with triethylamine (2.4 mL, 17 mmol) and 4-dimethylaminopyridine (0.35 g, 2.9 mmol). The solution was cooled to 0° C. and acetyl chloride (0.82 mL, 12 mmol) was added. The mixture was stirred at room temperature for 1 hour, washed with aqueous saturated NaHCO₃ (20 mL) and 1 M HCl (2×20 mL). The organic phase was dried (MgSO₄) and concentrated in vacuo to give the title compound (1.2 g). MS m/z 389 [M+H]⁺.

Intermediate 34

6-Methoxy-1-methyl-8-(phenylsulfonyl)-3,8-dihydro-4H-[1,4]oxazepino[6,7-e]indole To N-(2-{[6-methoxy-1-(phenylsulfonyl)-1H-indol-5-yl]oxy}ethyl)acetamide (Intermediate 33, 0.10 g, 2.7 mmol) dissolved in acetonitrile (150 mL), phosphoryl chloride (2 mL) was added and the reaction mixture was heated at reflux for 5 days. The solvent was removed under reduced pressure and the crude product was purified by preparative HPLC (XTerra C18, 50 mM NH₄HCO₃ pH 10-CH₃CN) to give the title compound (0.010 g). MS m/z 371 [M+H]⁺.

Example 87

6-Methoxy-1-methyl-8-(phenylsulfonyl)-1,3,4,8-tetrahydro-2H-[1,4]oxazepino[6,7-e]indole To 6-methoxy-1-methyl-8-(phenylsulfonyl)-3,8-dihydro-4H-[1,4]oxazepino[6,7-e]indole (Intermediate 34, 0.010 g, 0.027 mmol) dissolved in EtOH (2 mL), NaCNBH₃ (3.5 mg, 0.054 mmol) was added and the reaction mixture was heated at 65° C. for 2 hours. The reaction was quenched by addition of water and the solvent was removed under reduced pressure. The crude product was purified by preparative HPLC (XTerra C18, 50 mM NH₄HCO₃ pH 10-CH₃CN) to give the title compound (3.7 mg). MS m/z 373 [M+H]⁺.

Intermediate 35

6-Methoxy-1-methyl-1,3,4,8-tetrahydro-2H-[1,4]oxazepino[6,7-e]indole

To 6-methoxy-1-methyl-8-(phenylsulfonyl)-1,3,4,8-tetrahydro-2H-[1,4]oxazepino[6,7-e]indole (Example 87, 0.12 g, 0.32 mmol) dissolved in EtOH (20 mL), 2 M NaOH (5 mL, 10 mmol) was added and the reaction mixture was heated at 80° C. for 2 hours. The reaction mixture was cooled and extracted with DCM (50 mL). The organic layer was collected, dried (MgSO₄) and evaporated to afford the title compound (72 mg). MS m/z 233 [M+H]⁺.

Intermediate 36 tert-Butyl 6-methoxy-1-methyl-1,3,4,8-tetrahydro-2H-[1,4]oxazepino[6,7-e]indole-2-carboxylate Di-tert-butyl dicarbonate (85 mg, 0.39 mmol) was added to a solution of 6-methoxy-1-methyl-1,3,4,8-tetrahydro-2H-[1,4]oxazepino[6,7-e]indole (Intermediate 35, 72 mg, 0.32 mmol) in DCM (10 mL). The reaction mixture was stirred at room temperature overnight. The reaction mixture was washed with 1 M NaOH (5 mL) and the organic layer was dried (MgSO₄) and evaporated to give the title compound (100 mg). MS m/z 333 [M+H]⁺.

Example 88

8-[(2-Chlorophenyl)sulfonyl]-6-methoxy-1-methyl-1,3,4,8-tetrahydro-2H-[1,4]oxazepino[6,7-e]indole trifluoroacetate tert-Butyl 6-methoxy-1-methyl-1,3,4,8-tetrahydro-2H-[1,4]oxazepino[6,7-e]indole-2-carboxylate (Intermediate 36, 25 mg, 0.059 mmol) was dissolved in DMF (1 mL) and sodium hydride (60% in mineral oil, 4.0 mg, 0.15 mmol) was added. The reaction mixture was stirred at room temperature for 15 minutes before 2-chlorobenzenesulfonyl chloride (24 mg, 0.11 mmol) was added. The reaction mixture was allowed to stir at room temperature overnight and a few drops of water were added. The crude product was purified by preparative HPLC (XTerra C18, 50 mM NH₄HCO₃ pH 10-CH₃CN) to give tert-butyl 8-[(2-chlorophenyl)sulfonyl]-6-methoxy-1-methyl-1,3,4,8-tetrahydro-2H-[1,4]oxazepino[6,7-e]indole-2-carboxylate (6 mg) which was dissolved in DCM (1 mL) and TFA (1 mL) was added. The reaction mixture was stirred at room temperature for 3 hours and evaporated to give the title compound (5.8 mg). MS m/z 407 [M+H]⁺.

Example 89

6-Methoxy-1-methyl-8-[(2-methylphenyl)sulfonyl]-1,3,4,8-tetrahydro-2H-[1,4]oxazepino[6,7-e]indole trifluoroacetate tert-Butyl 6-methoxy-1-methyl-1,3,4,8-tetrahydro-2H-[1,4]oxazepino[6,7-e]indole-2-carboxylate (Intermediate 36, 25 mg, 0.059 mmol) was dissolved in DMF (1 mL) and sodium hydride (60% in mineral oil, 4.0 mg, 0.15 mmol) was added. The reaction mixture was stirred at room temperature for 15 minutes before 2-methylbenzenesulfonyl chloride (22 mg, 0.113 mmol) was added. The reaction mixture was allowed to stir at room temperature overnight and a few drops of water were added. The crude product was purified by preparative HPLC (XTerra C18, 50 mM NH$_4$HCO$_3$ pH 10-CH$_3$CN) to give tert-butyl 6-methoxy-1-methyl-8-[(2-methylphenyl)sulfonyl]-1,3,4,8-tetrahydro-2H-[1,4]oxazepino[6,7-e]indole-2-carboxylate (3.3 mg) which was dissolved in DCM (1 mL) and TFA (1 mL) was added. The reaction mixture was stirred at room temperature for 3 hours and evaporated to give the title compound (3.4 mg). MS m/z 387 [M+H]$^+$.

Example 90

8-[(2,6-Difluorophenyl)sulfonyl]-6-methoxy-1-methyl-1,3,4,8-tetrahydro-2H-[1,4]oxazepino[6,7-e]indole trifluoroacetate tert-Butyl 6-methoxy-1-methyl-1,3,4,8-tetrahydro-2H-[1,4]oxazepino[6,7-e]indole-2-carboxylate (Intermediate 36, 25 mg, 0.059 mmol) was dissolved in DMF (1 mL) and sodium hydride (60% in mineral oil, 4.0 mg, 0.15 mmol) was added. The reaction mixture was stirred at room temperature for 15 minutes before 2,6-difluorobenzenesulfonyl chloride (24.0 mg, 0.113 mmol) was added. The reaction mixture was allowed to stir at room temperature overnight and a few drops of water were added. The crude product was purified by preparative HPLC (XTerra C18, 50 mM NH$_4$HCO$_3$ pH 10-CH$_3$CN) to give tert-butyl 8-[(2,6-difluorophenyl)sulfonyl]-6-methoxy-1-methyl-1,3,4,8-tetrahydro-2H-[1,4]oxazepino[6,7-e]indole-2-carboxylate (6.6 mg, 0.013 mmol) which was dissolved in DCM (1 mL) and TFA (1 mL) was added. The reaction mixture was stirred at room temperature for 3 hours and evaporated to give the title compound (6.8 mg). MS m/z 409 [M+H]$^+$.

Example 91

6-Methoxy-8-[(2-methoxy-5-methylphenyl)sulfonyl]-1-methyl-1,3,4,8-tetrahydro-2H-[1,4]oxazepino[6,7-e]indole trifluoroacetate tert-Butyl 6-methoxy-1-methyl-1,3,4,8-tetrahydro-2H-[1,4]oxazepino[6,7-e]indole-2-carboxylate (Intermediate 36, 25 mg, 0.059 mmol) was dissolved in DMF (1 mL) and sodium hydride (60% in mineral oil, 4.0 mg, 0.15 mmol) was added. The reaction mixture was stirred at room temperature for 15 minutes before 2-methoxy-5-methylbenzenesulfonyl chloride (24.0 mg, 0.113 mmol) was added. The reaction mixture was allowed to stir at room temperature overnight and a few drops of water were added. The crude product was purified by preparative HPLC (XTerra C18, 50 mM NH$_4$HCO$_3$ pH 10-CH$_3$CN) to give tert-butyl 6-methoxy-8-[(2-methoxy-5-methylphenyl)sulfonyl]-1-methyl-1,3,4,8-tetrahydro-2H-[1,4]oxazepino[6,7-e]indole-2-carboxylate (4.4 mg) which was dissolved in DCM (1 mL) and TFA (1 mL) was added. The reaction mixture was stirred at room temperature for 3 hours and evaporated to give the title compound (4.6 mg). MS m/z 417 [M+H]$^+$.

Example 92

8-[(2,4-Dichlorophenyl)sulfonyl]-6-methoxy-1-methyl-1,3,4,8-tetrahydro-2H-[1,4]oxazepino[6,7-e]indole trifluoroacetate tert-Butyl 6-methoxy-1-methyl-1,3,4,8-tetrahydro-2H-[1,4]oxazepino[6,7-e]indole-2-carboxylate (Intermediate 36, 25 mg, 0.059 mmol) was dissolved in DMF (1 mL) and sodium hydride (60% in mineral oil, 4.0 mg, 0.15 mmol) was added. The reaction mixture was stirred at room temperature for 15 minutes before 2,4-dichlorobenzenesulfonyl chloride (28 mg, 0.113 mmol) was added. The reaction mixture was allowed to stir at room temperature overnight and a few drops of water were added. The crude product was purified by preparative HPLC (XTerra C18, 50 mM NH$_4$HCO$_3$ pH 10-CH$_3$CN) to give tert-butyl 8-[(2,4-dichlorophenyl)sulfonyl]-6-methoxy-1-methyl-1,3,4,8-tetrahydro-2H-[1,4]oxazepino[6,7-e]indole-2-carboxylate (6 mg) which was dissolved in DCM (1 mL) and TFA (1 mL) was added. The reaction mixture was stirred at room temperature for 3 hours and evaporated to give the title compound (4.2 mg). MS m/z 442 [M+H]$^+$.

Intermediate 37

2-Methyl-N-(2-{[1-(phenylsulfonyl)-1H-indol-5-yl]oxy}ethyl)propanamide

2-{[1-(Phenylsulfonyl)-1H-indol-5-yl]oxy}ethanamine (Intermediate 24, 0.20 g, 0.63 mmol) in DCM (100 mL) was treated with triethylamine (0.27 mL, 1.9 mmol) and 4-dimethylaminopyridine (39 mg, 0.32 mmol). The solution was cooled to 0° C. and was treated with isobutyryl chloride (0.14 g, 0.13 mmol). The mixture was stirred at room temperature for 1 hour. The mixture was washed with saturated aqueous NaHCO$_3$ (50 mL) and 1 M HCl (2×40 mL). The organic phase was dried (MgSO$_4$) and concentrated in vacuo to give the title compound (133 mg). MS m/z 387 [M+H]$^+$.

Intermediate 38

1-Isopropyl-8-(phenylsulfonyl)-3,8-dihydro-4H-[1,4]oxazepino[6,7-e]indole

To 2-methyl-N-(2-{[1-(phenylsulfonyl)-1H-indol-5-yl]oxy}ethyl)propanamide (Intermediate 37, 0.13 g, 0.33 mmol) in acetonitrile (200 mL) was phosphoryl chloride (2.5 mL) added and the reaction mixture was heated at reflux for 20 hours. The reaction mixture was evaporated to give the title compound (120 mg). MS m/z 369 [M+H]$^+$.

Example 93

1-Isopropyl-8-(phenylsulfonyl)-1,3,4,8-tetrahydro-2H-[1,4]oxazepino[6,7-e]indole To 1-isopropyl-8-(phenylsulfonyl)-3,8-dihydro-4H-[1,4]oxazepino[6,7-e]indole (Intermediate 38, 120 mg, 0.330 mmol) dissolved in EtOH (5 mL), NaCNBH$_3$ (41 mg, 0.65 mmol) was added and the reaction mixture was heated at 70° C. for 30 minutes. The reaction was quenched by addition of water and the solvent was removed under reduced pressure. The crude product was purified by preparative HPLC (XTerra C18, 50 mM NH$_4$HCO$_3$ pH 10-CH$_3$CN) to give the title compound (35 mg). MS m/z 371 [M+H]$^+$.

Example 94

1-Isopropyl-2-methyl-8-(phenylsulfonyl)-1,3,4,8-tetrahydro-2H-[1,4]oxazepino[6,7-e]indole 1-Isopropyl-8-(phenylsulfonyl)-1,3,4,8-tetrahydro-2H-[1,4]oxazepino[6,7-e]indole (Example 93, 25 mg, 0.068 mmol) was dissolved in methanol (4 mL) and formaldehyde (37 wt. % in H$_2$O, 0.090 mL, 1.1 mmol) was added followed by sodium triacetoxyborohydride (72 mg, 0.34 mmol). The reaction mixture was allowed to stir at room temperature overnight, evaporated and the crude product was purified by preparative HPLC (XTerra C18, 50 mM $NH_4HCO_3$ pH 10-$CH_3CN$) to give the title compound (1.4 mg). MS m/z 385 $[M+H]^+$.

Example 95

1,2-Dimethyl-8-(phenylsulfonyl)-1,3,4,8-tetrahydro-2H-[1,4]oxazepino[6,7-e]indole trifluoroacetate 1-Methyl-8-(phenylsulfonyl)-1,3,4,8-tetrahydro-2H-[1,4]oxazepino[6,7-e]indole (Example 82, 15 mg, 0.044 mmol) was dissolved in THF (2 mL) and formaldehyde (37 wt. % in $H_2O$, 0.090 mL, 1.1 mmol) was added. The mixture was stirred for 10 minutes before sodium triacetoxyborohydride (0.010 g, 0.048 mmol) was added. The reaction was allowed to stir for 1 hour at room temperature, evaporated and purified by flash chromatography on silica gel using MeOH:DCM:$NEt_3$ (5:94:1) as the eluent to give the title compound (9.2 mg) as a colorless liquid. MS m/z 357 $[M+H]^+$.

Intermediate 39

N-(2-{[3-chloro-1-(phenylsulfonyl)-1H-indol-5-yl]oxy}ethyl)acetamide

N-chlorosuccinimide (0.42 g, 3.2 mmol) was added to a solution of N-(2-{[1-(phenylsulfonyl)-1H-indol-5-yl]oxy}ethyl)acetamide (Intermediate 25, 0.95 g, 2.6 mmol) in THF (20 ml) at room temperature. The reaction mixture was stirred at 40° C. for 6 hours. The reaction mixture was evaporated and the crude material was purified by flash chromatography on silica gel using 3% MeOH in DCM as the eluent to give the title compound (1.11 g) as a white solid. MS m/z 393 $[M+H]^+$.

Intermediate 40

10-chloro-1-methyl-3,8-dihydro-4H-[1,4]oxazepino[6,7-e]indole

N-(2-{[3-chloro-1-(phenylsulfonyl)-1H-indol-5-yl]oxy}ethyl)acetamide (Intermediate 39, 1.07 g, 2.73 mmol, ca 80% pure) in EtOH (25 ml) and 2 M NaOH (5 ml) were mixed and heated at 75° C. for 1 hour. The reaction mixture was cooled, diluted with water and extracted with DCM. The organic phase was dried ($MgSO_4$) and evaporated to give the crude material (0.287 g) as a colorless oil. The crude material (0.250 g, 0979 mmol) was dissolved in MeCN (20 ml) and $POCl_3$ was added. The reaction mixture was heated at 120° C. for 15 minutes in a microwave heater and evaporated. The crude material was purified by preparative HPLC (XTerra C18, 50 mM $NH_4HCO_3$ pH 10-$CH_3CN$) to give the title compound (99.7 mg) as a white solid. MS m/z 235 $[M+H]^+$.

Example 96

10-chloro-1-methyl-8-(phenylsulfonyl)-3,8-dihydro-4H-[1,4]oxazepino[6,7-e]indole Sodium hydride (60% in mineral oil, 38 mg, 0.95 mmol) was added to 10-chloro-1-methyl-3,8-dihydro-4H-[1,4]oxazepino[6,7-e]indole (Intermediate 40, 45 mg, 0.19 mmol) and benzensulfonyl chloride (74 µl, 0.58 mmol) in DMF (3 ml). The reaction mixture was stirred at room temperature for 10 minutes before water was added dropwise. The crude material was purified by preparative HPLC (XTerra C18, 50 mM $NH_4HCO_3$ pH 10-$CH_3CN$) to give the title compound (15 mg) as a red solid. MS m/z 375 $[M+H]^+$.

Intermediate 41 tert-Butyl 1-methyl-8-(phenylsulfonyl)-1,3,4,8-tetrahydro-2H-[1,4]oxazepino[6,7-e]indole-2-carboxylate Di-tert-butyl dicarbonate (3.5 g, 16 mmol) was added to a solution of 1-methyl-8-(phenylsulfonyl)-1,3,4,8-tetrahydro-2H-[1,4]oxazepino[6,7-e]indole (Example 82, 5.0 g, 15 mmol) in DCM (200 mL). The reaction mixture was stirred at room temperature overnight and washed with 1 M NaOH (100 mL). The solvent was removed under reduced pressure and the crude product was purified by preparative HPLC (XTerra C18, 50 mM $NH_4HCO_3$ pH 10-$CH_3CN$) to give the title compound (2.88 g). MS m/z 443 $[M+H]^+$.

Intermediate 42 tert-Butyl 1-methyl-1,3,4,8-tetrahydro-2H-[1,4]oxazepino[6,7-e]indole-2-carboxylate To tert-butyl 1-methyl-8-(phenylsulfonyl)-1,3,4,8-tetrahydro-2H-[1,4]oxazepino[6,7-e]indole-2-carboxylate (Intermediate 41, 1.5 g, 3.4 mmol) dissolved in EtOH (50 mL), 2 M NaOH (10 mL, 20 mmol) was added and the reaction mixture was heated at 70° C. for 2 hours. The EtOH was removed under reduced pressure and the water phase was extracted with DCM (2×100 mL). The organic layer was collected, dried ($MgSO_4$) and evaporated to afford the title compound (0.98 g) as a yellow solid. MS m/z 303 $[M+H]^+$.

Intermediate 43 tert-Butyl 10-chloro-1-methyl-1,3,4,8-tetrahydro-2H-[1,4]oxazepino[6,7-e]indole-2-carboxylate N-chlorosuccinimide (13 mg, 0.10 mmol) was added to a solution of tert-butyl 1-methyl-1,3,4,8-tetrahydro-2H-[1,4]oxazepino[6,7-e]indole-2-carboxylate (Intermediate 42, 0.030 g, 0.099 mmol) in THF (2 mL) and the reaction mixture was stirred at room temperature overnight. The solvent was evaporated and the crude material was purified by preparative HPLC (XTerra C18, 50 mM $NH_4HCO_3$ pH 10-$CH_3CN$) to give the title compound (17.5 mg) as a white solid. MS m/z 337 $[M+H]^+$.

Example 97

10-Chloro-1-methyl-8-(pyridin-3-ylsulfonyl)-1,3,4,8-tetrahydro-2H-[1,4]oxazepino[6,7-e]indole bis(trifluoroacetate)

tert-Butyl 10-chloro-1-methyl-1,3,4,8-tetrahydro-2H-[1,4]oxazepino[6,7-e]indole-2-carboxylate (Intermediate 43, 77 mg, 0.23 mmol) was dissolved in DCM (6 mL) and 2 M NaOH (0.25 mL, 0.50 mmol) tetrabutylammonium hydrogensulfate (15.5 mg, 0.046 mmol) and pyridine-3-sulfonyl chloride (98.0 mg, 0.458 mmol) were added and the mixture was stirred at room temperature overnight. The organic layer was separated and concentrated to ca 2 mL. TFA (3 mL) was added and the mixture was stirred at room temperature for 30 minutes and evaporated. The crude material was purified by preparative HPLC (ACE C8, 0.1% TFA-$CH_3CN$) to give the title compound as a brown oil (16.8 mg) in the form of the trifluoroacetate salt. MS m/z 378 [M+H]+.

Example 98

10-Chloro-1-methyl-8-(phenylsulfonyl)-1,3,4,8-tetrahydro-2H-[1,4]oxazepino[6,7-e]indole trifluoroacetate Sodium hydride (60% in mineral oil, 0.010 g, 0.42 mmol) was added to tert-butyl 10-chloro-1-methyl-1,3,4,8-tetrahydro-2H-[1,4]oxazepino[6,7-e]indole-2-carboxylate (Intermediate 43, 18 mg, 0.050 mmol) and benzenesulfonyl chloride (0.030 mL, 0.23 mmol) in DMF (2 mL). The mixture was was stirred at room temperature for 30 minutes. TFA (0.50 mL) was added to the reaction mixture and the solvent was evaporated. The residue was dissolved in DCM (1 mL) and TFA (1 mL) was added. The reaction mixture was stirred for 10 minutes and evaporated. The crude material was purified by preparative HPLC (ACE C8, 0.1% TFA-CH$_3$CN) to give the title compound as a white solid (16.8 mg) in the form of the trifluoroacetate salt. MS m/z 377 [M+H]+.

Example 99

10-Chloro-1,2-dimethyl-8-(phenylsulfonyl)-1,3,4,8-tetrahydro-2H-[1,4]oxazepino[6,7-e]indole 10-Chloro-1-methyl-8-(phenylsulfonyl)-1,3,4,8-tetrahydro-2H-[1,4]oxazepino[6,7-e]indole trifluoroacetate (Example 98, 59 mg, 0.15 mmol) in MeOH (1 mL) was converted to the free amine by PL-HCO$_3$ MP SPE (Polymer Laboratories) column. Formaldehyde (37 wt. % in H$_2$O, 0.20 mL, 2.4 mmol) was added to a solution of the free amine (0.15 mmol) in THF (1 mL). After stirring for 10 minutes at room temperature sodium triacetoxyborohydride (26 mg, 0.12 mmol) was added and the mixture was stirred for an additional 30 minutes and evaporated. The crude material was purified by preparative HPLC (Xterra C18, 10 mM NH$_4$HCO$_3$ (pH 10) —CH3CN) to give the title compound as a white solid (28.9 mg). MS m/z 391 [M+H]+.

Example 100

10-Chloro-8-[(2-methoxy-5-methylphenyl)sulfonyl]-1-methyl-1,3,4,8-tetrahydro-2H-[1,4]oxazepino[6,7-e]indole Sodium hydride (60% in mineral oil, 18 mg, 0.74 mmol) was added to a solution of 6-methoxy-m-toluensulfonyl chloride (98.3 mg, 0.445 mmol) and tert-butyl 10-chloro-1-methyl-1,3,4,8-tetrahydro-2H-[1,4]oxazepino[6,7-e]indole-2-carboxylate (Intermediate 43, 50.0 mg, 0.148 mmol) in DMF (2 mL) at room temperature. The mixture was stirred for 15 minutes before water (5 mL) was added and the aqueous layer was extracted with DCM. Most of the organic solvents were evaporated and the residue was dissolved in DCM (1 mL) and TFA (2 mL) was added. The reaction mixture was stirred at room temperature for 30 minutes. Solvents were evaporated and the crude product was purified by preparative HPLC (Xterra C18, 10 mM NH$_4$HCO$_3$ (pH 10) —CH3CN) to give the title compound as a white solid (16.8 mg). MS m/z 421 [M+H]+.

Example 101

10-Chloro-8-[(2-methoxy-5-methylphenyl)sulfonyl]-1,2-dimethyl-1,3,4,8-tetrahydro-2H-[1,4]oxazepino[6,7-e]indole trifluoroacetate Formaldehyde (37 wt. % in H$_2$O, 0.20 mL, 2.4 mmol) was added to a solution of 10-chloro-8-[(2-methoxy-5-methylphenyl)sulfonyl]-1-methyl-1,3,4,8-tetrahydro-2H-[1,4]oxazepino[6,7-e]indole (Example 100, 12 mg, 0.029 mmol) in THF (1 mL). After stirring for 10 minutes at room temperature sodium triacetoxyborohydride (9.2 mg, 0.043 mmol) was added and the mixture was stirred for an additional 30 minutes and evaporated. The crude material was purified by preparative HPLC (ACE C8, 0.1% TFA —CH$_3$CN) to give the title compound as a white solid (12.7 mg) in the form of the trifluoroacetate salt. MS m/z 435 [M+H]+.

Example 102

10-Chloro-8-[(2-fluorophenyl)sulfonyl]-1-methyl-1,3,4,8-tetrahydro-2H-[1,4]oxazepino[6,7-e]indole trifluoroacetate Sodium hydride (60% in mineral oil, 18 mg, 0.74 mmol) was added to a solution of 2-fluorobenzene-1-sulfonyl chloride (86.7 mg, 0.445 mmol) and tert-butyl 10-chloro-1-methyl-1,3,4,8-tetrahydro-2H-[1,4]oxazepino[6,7-e]indole-2-carboxylate (Intermediate 43, 50.0 mg, 0.15 mmol) in DMF (2 mL) at room temperature. The mixture was stirred for 15 minutes before water (5 mL) was added and the aqueous layer was extracted with DCM. Most of the organic solvents were evaporated and the residue was dissolved in DCM (1 mL) and TFA (2 mL) was added. The reaction mixture was stirred at room temperature for 30 minutes. Solvents were evaporated and the crude material was purified by preparative HPLC (ACE C8, 0.1% TFA-CH$_3$CN) to give the title compound as a white solid (18 mg) in the form of the trifluoroacetate salt. MS m/z 395 [M+H]+.

Example 103

10-Chloro-8-[(2-fluorophenyl)sulfonyl]-1,2-dimethyl-1,3,4,8-tetrahydro-2H-[1,4]oxazepino[6,7-e]indole trifluoroacetate 10-Chloro-8-[(2-fluorophenyl)sulfonyl]-1-methyl-1,3,4,8-tetrahydro-2H-[1,4]oxazepino[6,7-e]indole trifluoroacetate (Example 102, 12.5, 0.025 mmol) in MeOH (1 mL) was converted to free amine using a PL-HCO$_3$ MP SPE (Polymer Laboratories) column.
Formaldehyde (37 wt. % in H$_2$O, 0.20 mL, 2.4 mmol) was added to a solution of the free amine (0.025 mmol) in THF (1 mL). After stirring for 10 minutes at room temperature sodium triacetoxyborohydride (10 mg, 0.047 mmol) was added and the mixture was stirred for an additional 30 minutes and evaporated. The crude material was purified by preparative HPLC (ACE C8, 0.1% TFA-CH$_3$CN) to give the title compound as a colorless gum (11.2 mg) in the form of the trifluoroacetate salt. MS m/z 409 [M+H]+.

Example 104

10-Chloro-8-[(3-fluorophenyl)sulfonyl]-1-methyl-1,3,4,8-tetrahydro-2H-[1,4]oxazepino[6,7-e]indole trifluoroacetate Sodium hydride (60% in mineral oil, 18 mg, 0.74 mmol) was added to a solution of 3-fluorobenzene-1-sulfonyl chloride (86.7 mg, 0.445 mmol) and tert-butyl 10-chloro-1-methyl-1,3,4,8-tetrahydro-2H-[1,4]oxazepino[6,7-e]indole-2-carboxylate (Intermediate 43, 50.0 mg, 0.15 mmol) in DMF (2 mL) at room temperature. The mixture was stirred for 15 minutes before water (5 mL) was added and the aqueous layer was extracted with DCM. Most of the organic solvents were evaporated and the residue was dissolved in DCM (1 mL) and TFA (2 mL) was added. The reaction mixture was stirred at room temperature for 30 minutes. Solvents were evaporated and the crude material was purified by preparative HPLC (ACE C8, 0.1% TFA-CH$_3$CN) to give the title compound as a brown solid (18.5 mg) in the form of the trifluoroacetate salt. MS m/z 395 [M+H]$^+$.

Example 105

10-Chloro-8-[(3-fluorophenyl)sulfonyl]-1,2-dimethyl-1,3,4,8-tetrahydro-2H-[1,4]oxazepino[6,7-e]indole trifluoroacetate 10-Chloro-8-[(3-fluorophenyl)sulfonyl]-1-methyl-1,3,4,8-tetrahydro-2H-[1,4]oxazepino[6,7-e]indole trifluoroacetate (Example 104, 11.8 mg, 0.023 mmol) was converted to free amine using PL-HCO3 MP SPE column.

Formaldehyde (37 wt. % in H$_2$O, 0.20 mL, 2.4 mmol) was added to a solution of the free amine (0.023 mmol) in THF (1 mL). After stirring for 10 minutes at room temperature sodium triacetoxyborohydride (10 mg, 0.047 mmol) was added and the mixture was stirred for an additional 30 minutes and evaporated. The crude material was purified by preparative HPLC (ACE C8, 0.1% TFA-CH$_3$CN) to give the title compound as a colorless gum (8.2 mg) in the form of the trifluoroacetate salt. MS m/z 409 [M+H]$^+$.

Example 106

1-Methyl-8-(pyridin-3-ylsulfonyl)-1,3,4,8-tetrahydro-2H-[1,4]oxazepino[6,7-e]indole bis(trifluoroacetate)

To a solution of tert-butyl 1-methyl-1,3,4,8-tetrahydro-2H-[1,4]oxazepino[6,7-e]indole-2-carboxylate (Intermediate 42, 0.030 g (0.098 mmol) in DCM (2 mL), tetrabutyl ammonium hydrogensulphate, (6.4 mg, 0.020 mmol), 2 M NaOH (0.2 mL, 0.4 mmol) and pyridine-3-sulfonyl chloride hydrochloride (35 mg, 0.20 mmol) were added. The reaction mixture was stirred vigorously at room temperature for one hour. More 2 M NaOH (1 mL, 2 mmol) was added to the mixture, followed by the sulfonyl chloride (17 mg, 0.10 mmol) every hour for four hours (a total of 103 mg). Water (10 mL) was added and the aqueous phase was washed with CHCl$_3$ (2×) and the combined organics were evaporated under reduced pressure. To the resulting oil was added TFA/DCM 50/50 (1 mL) and the mixture was stirred at room temperature overnight. The solvent was removed under reduced pressure and the material was purified by preparative HPLC (ACE C8, 0.1% TFA-CH$_3$CN) to give the title compound (7.4 mg) in the form of the trifluoroacetate salt. MS m/z 344 [M+H]$^+$.

Example 107

8-[(2-Chlorophenyl)sulfonyl]-1-methyl-1,3,4,8-tetrahydro-2H-[1,4]oxazepino[6,7-e]indole trifluoroacetate tert-Butyl 1-methyl-1,3,4,8-tetrahydro-2H-[1,4]oxazepino[6,7-e]indole-2-carboxylate (Intermediate 42, 25 mg, 0.083 mmol) was dissolved in DMF (1 mL) and sodium hydride (60% in mineral oil, 4.0 mg, 0.17 mmol) was added. The reaction mixture was stirred at room temperature for 15 minutes before 2-chlorobenzenesulfonyl chloride (26.0 mg, 0.125 mmol) was added. The reaction mixture was allowed to stir at room temperature overnight. The reaction was quenched by addition of water and the crude product was purified by preparative HPLC (XTerra C18, 50 mM NH$_4$HCO$_3$ pH 10-CH$_3$CN) to give the boc-protected intermediate as a white solid (23 mg) which was dissolved in DCM (1 mL) and TFA (1 mL) was added. The reaction mixture was stirred at room temperature for 1 hour and the solvent was removed under reduced pressure. The crude material was purified by preparative HPLC (ACE C8, 0.1% TFA-CH$_3$CN) to give the title compound as a white solid (0.010 g) in the form of the trifluoroacetate salt. MS m/z 377 [M+H]$^+$.

Example 108

1-Methyl-8-[(2-methylphenyl)sulfonyl]-1,3,4,8-tetrahydro-2H-[1,4]oxazepino[6,7-e]indole tert-Butyl 1-methyl-1,3,4,8-tetrahydro-2H-[1,4]oxazepino[6,7-e]indole-2-carboxylate (Intermediate 42, 25 mg, 0.083 mmol) was dissolved in DMF (1 mL) and sodium hydride (60% in mineral oil, 4.0 mg, 0.17 mmol) was added. The reaction mixture was stirred at room temperature for 15 minutes before 2-methylbenzenesulfonyl chloride (22 mg, 0.11 mmol) was added. The reaction mixture was allowed to stir at room temperature overnight. The reaction was quenched by addition of water and the crude product was purified by preparative HPLC (XTerra C18, 50 mM NH$_4$HCO$_3$ pH 10-CH$_3$CN) to give tert-butyl 1-methyl-8-[(2-methylphenyl)sulfonyl]-1,3,4,8-tetrahydro-2H-[1,4]oxazepino[6,7-e]indole-2-carboxylate (21 mg) which was dissolved in DCM (1 mL) and TFA (1 mL) was added. The reaction mixture was stirred at room temperature for 1 hour and the solvent was removed under reduced pressure. The crude material was purified by preparative HPLC (ACE C8, 0.1% TFA-CH$_3$CN) to give the title compound (1.1 mg) as a white solid. MS m/z 357 [M+H]$^+$.

Example 109

8-[(2,6-Difluorophenyl)sulfonyl]-1-methyl-1,3,4,8-tetrahydro-2H-[1,4]oxazepino[6,7-e]indole tert-Butyl 1-methyl-1,3,4,8-tetrahydro-2H-[1,4]oxazepino[6,7-e]indole-2-carboxylate (Intermediate 42, 25 mg, 0.083 mmol) was dissolved in DMF (1 mL) and sodium hydride (60% in mineral oil, 4.0 mg, 0.17 mmol) was added. The reaction mixture was stirred at room temperature for 15 minutes before 2,6-difluorobenzenesulfonyl chloride (26 mg, 0.11 mmol) was added. The reaction mixture was allowed to stir at room temperature overnight. The reaction was quenched by addition of water and the crude product was purified by preparative HPLC (XTerra C18, 50 mM NH$_4$HCO$_3$ pH 10-CH$_3$CN) to give tert-butyl 8-[(2,6-difluorophenyl)sulfonyl]-1-methyl-1,3,4,8-tetrahydro-2H-[1,4]oxazepino[6,7-e]indole-2-carboxylate (17 mg) which was dissolved in DCM (1 mL) and TFA (1 mL) was added. The reaction mixture was stirred at room temperature for 1 hour and the solvent was removed under reduced pressure. The crude material was purified by preparative HPLC (XTerra C18, 50 mM NH$_4$HCO$_3$ pH 10-CH$_3$CN) to give the title compound (6 mg). MS m/z 379 [M+H]$^+$.

Example 110

8-[(2,4-Dichlorophenyl)sulfonyl]-1-methyl-1,3,4,8-tetrahydro-2H-[1,4]oxazepino[6,7-e]indole tert-Butyl 1-methyl-1,3,4,8-tetrahydro-2H-[1,4]oxazepino[6,7-e]indole-2-carboxylate (Intermediate 42, 25 mg, 0.083 mmol) was dissolved in DMF (1 mL) and sodium hydride (60% in mineral oil, 4.0 mg, 0.17 mmol) was added. The reaction mixture was stirred at room temperature for 15 minutes before 2,4-dichlorobenzenesulfonyl chloride (28 mg, 0.11 mmol) was added. The reaction mixture was allowed to stir at room temperature overnight. The reaction was quenched by addition of water and the crude product was purified by preparative HPLC (XTerra C18, 50 mM NH$_4$HCO$_3$ pH 10-CH$_3$CN) to give tert-butyl 8-[(2,4-dichlorophenyl)sulfonyl]-1-methyl-1,3,4,8-tetrahydro-2H-[1,4]oxazepino[6,7-e]indole-2-carboxylate (2 mg) which was dissolved in DCM (1 mL) and TFA (1 mL) was added. The reaction mixture was stirred at room temperature for 1 hour and the solvent was removed under reduced pressure. The crude material was purified by preparative HPLC (XTerra C18, 50 mM NH$_4$HCO$_3$ pH 10-CH$_3$CN) to give the title compound (0.7 mg). MS m/z 412 [M+H]$^+$.

Example 111

8-[(2-Methoxy-5-methylphenyl)sulfonyl]-1-methyl-1,3,4,8-tetrahydro-2H-[1,4]oxazepino[6,7-e]indole tert-Butyl 1-methyl-1,3,4,8-tetrahydro-2H-[1,4]oxazepino[6,7-e]indole-2-carboxylate (Intermediate 42, 25 mg, 0.083 mmol) was dissolved in DMF (1 mL) and sodium hydride (60% in mineral oil, 4.0 mg, 0.17 mmol) was added. The reaction mixture was stirred at room temperature for 15 minutes before 2-methoxy-5-methylbenzenesulfonyl chloride (25 mg, 0.11 mmol) was added and the reaction mixture was stirred overnight. The reaction was quenched by addition of water and the crude product was purified by preparative HPLC (XTerra C18, 50 mM NH$_4$HCO$_3$ pH 10-CH$_3$CN) to give tert-butyl 8-[(2-methoxy-5-methylphenyl)sulfonyl]-1-methyl-1,3,4,8-tetrahydro-2H-[1,4]oxazepino[6,7-e]indole-2-carboxylate (7 mg) which was dissolved in DCM (1 mL) and TFA (1 mL) was added. The reaction mixture was stirred at room temperature for 1 hour and the solvent was removed under reduced pressure. The crude material was purified by preparative HPLC (XTerra C18, 50 mM NH$_4$HCO$_3$ pH 10-CH$_3$CN) to give the title compound (2 mg). MS m/z 387 [M+H]$^+$.

Example 112

8-[(2-Methoxy-4-methylphenyl)sulfonyl]-1-methyl-1,3,4,8-tetrahydro-2H-[1,4]oxazepino[6,7-e]indole tert-Butyl 1-methyl-1,3,4,8-tetrahydro-2H-[1,4]oxazepino[6,7-e]indole-2-carboxylate (Intermediate 42, 25 mg, 0.083 mmol) was dissolved in DMF (1 mL) and sodium hydride (60% in mineral oil, 4.0 mg, 0.17 mmol) was added. The reaction mixture was stirred at room temperature for 15 minutes before 2-methoxy-4-methylbenzenesulfonyl chloride (25 mg, 0.11 mmol) was added. The reaction mixture was allowed to stir at room temperature overnight. The reaction was quenched by addition of water and the crude product was purified by preparative HPLC (XTerra C18, 50 mM NH$_4$HCO$_3$ pH 10-CH$_3$CN) to give tert-butyl 8-[(2-methoxy-4-methylphenyl)sulfonyl]-1-methyl-1,3,4,8-tetrahydro-2H-[1,4]oxazepino[6,7-e]indole-2-carboxylate (21 mg) which was dissolved in DCM (1 mL) and TFA (1 mL) was added. The reaction mixture was stirred at room temperature for 1 hour and the solvent was removed under reduced pressure. The crude material was purified by preparative HPLC (XTerra C18, 50 mM NH$_4$HCO$_3$ pH 10-CH$_3$CN) to give the title compound (7 mg). MS m/z 387 [M+H]$^+$.

Example 113

8-[(2,5-Dimethyl-3-thienyl)sulfonyl]-1-methyl-1,3,4,8-tetrahydro-2H-[1,4]oxazepino[6,7-e]indole tert-Butyl 1-methyl-1,3,4,8-tetrahydro-2H-[1,4]oxazepino[6,7-e]indole-2-carboxylate (Intermediate 42, 25 mg, 0.083 mmol) was dissolved in DMF (1 mL) and sodium hydride (60% in mineral oil, 4.0 mg, 0.17 mmol) was added. The reaction mixture was stirred at room temperature for 15 minutes before 2,5-dimethyl-3-thienyl sulfonyl chloride (24 mg, 0.11 mmol) was added. The reaction mixture was allowed to stir at room temperature overnight. The reaction was quenched by addition of water and the crude product was purified by preparative HPLC (XTerra C18, 50 mM NH$_4$HCO$_3$ pH 10-CH$_3$CN) to give tert-butyl 8-[(2,5-dimethyl-3-thienyl)sulfonyl]-1-methyl-1,3,4,8-tetrahydro-2H-[1,4]oxazepino[6,7-e]indole-2-carboxylate (6 mg) which was dissolved in DCM (1 mL) and TFA (1 mL) was added. The reaction mixture was stirred at room temperature for 1 hour and the solvent was removed under reduced pressure. The crude material was purified by preparative HPLC (XTerra C18, 50 mM NH$_4$HCO$_3$ pH 10-CH$_3$CN) to give the title compound (4 mg). MS m/z 377 [M+H]$^+$.

Example 114

8-[(2,5-Dimethyl-3-furyl)sulfonyl]-1-methyl-1,3,4,8-tetrahydro-2H-[1,4]oxazepino[6,7-e]indole tert-Butyl 1-methyl-1,3,4,8-tetrahydro-2H-[1,4]oxazepino[6,7-e]indole-2-carboxylate (Intermediate 42, 25 mg, 0.083 mmol) was dissolved in DMF (1 mL) and sodium hydride (60% in mineral oil, 4.0 mg, 0.17 mmol) was added. The reaction mixture was stirred at room temperature for 15 minutes before 2,5-dimethyl-3-furansulfonyl chloride (22 mg, 0.11 mmol) was added. The reaction mixture was allowed to stir at room temperature overnight. The reaction was quenched by addition of water and the crude product was purified by preparative HPLC (XTerra C18, 50 mM NH$_4$HCO$_3$ pH 10-CH$_3$CN) to give tert-butyl 8-[(2,5-dimethyl-3-furyl)sulfonyl]-1-methyl-1,3,4,8-tetrahydro-2H-[1,4]oxazepino[6,7-e]indole-2-carboxylate (19 mg) which was dissolved in DCM (1 mL) and TFA (1 mL) was added. The reaction mixture was stirred at room temperature for 1 hour and the solvent was removed under reduced pressure. The crude material was purified by preparative HPLC (XTerra C18, 50 mM NH$_4$HCO$_3$ pH 10-CH$_3$CN) to give the title compound (2 mg). MS m/z 361 [M+H]$^+$.

Example 115

1-Methyl-8-(2-thienylsulfonyl)-1,3,4,8-tetrahydro-2H-[1,4]oxazepino[6,7-e]indole tert-Butyl 1-methyl-1,3,4,8-tetrahydro-2H-[1,4]oxazepino[6,7-e]indole-2-carboxylate (Intermediate 42, 25 mg, 0.083 mmol) was dissolved in DMF (1 mL) and sodium hydride (60% in mineral oil, 4.0 mg, 0.17 mmol) was added. The reaction mixture was stirred at room temperature for 15 minutes before 2-thiophenesulfonyl chloride (21 mg, 0.11 mmol) was added. The reaction mixture was allowed to stir at room temperature overnight. The reaction was quenched by addition of water and the crude product was purified by preparative HPLC (XTerra C18, 50 mM NH$_4$HCO$_3$ pH 10-CH$_3$CN) to give tert-butyl 1-methyl-8-(2-thienylsulfonyl)-1,3,4,8-tetrahydro-2H-[1,4]oxazepino[6,7-e]indole-2-carboxylate (14 mg) which was dissolved in DCM (1 mL) and TFA (1 mL) was added. The reaction mixture was stirred at room temperature for 1 hour and the solvent was removed under reduced pressure. The crude material was purified by preparative preparative HPLC (XTerra C18, 50 mM NH$_4$HCO$_3$ pH 10-CH$_3$CN) to give the title compound (5 mg). MS m/z 349 [M+H]$^+$.

Example 116

1-Methyl-8-[(5-methylisoxazol-4-yl)sulfonyl]-1,3,4,8-tetrahydro-2H-[1,4]oxazepino[6,7-e]indole tert-Butyl 1-methyl-1,3,4,8-tetrahydro-2H-[1,4]oxazepino[6,7-e]indole-2-carboxylate (Intermediate 42, 25 mg, 0.083 mmol) was dissolved in DMF (1 mL) and sodium hydride (60% in mineral oil, 4.0 mg, 0.17 mmol) was added. The reaction mixture was stirred at room temperature for 15 minutes before 5-methyl-4-isoxazolesulfonyl chloride (21 mg, 0.11 mmol) was added. The reaction mixture was allowed to stir at room temperature overnight. The reaction was quenched by addition of water and the crude product was purified by preparative HPLC (XTerra C18, 50 mM NH$_4$HCO$_3$ pH 10-CH$_3$CN) to give tert-butyl 1-methyl-8-[(5-methylisoxazol-4-yl)sulfonyl]-1,3,4,8-tetrahydro-2H-[1,4]oxazepino[6,7-e]indole-2-carboxylate (0.010 g) which was dissolved in DCM (1 mL) and TFA (1 mL) was added. The reaction mixture was stirred at room temperature for 1 hour and the solvent was removed under reduced pressure. The crude material was purified by preparative HPLC (XTerra C18, 50 mM NH$_4$HCO$_3$ pH 10-CH$_3$CN) to give the title compound (1 mg). MS m/z 348 [M+H]$^+$.

Example 117

8-[(1,2-Dimethyl-1H-imidazol-4-yl)sulfonyl]-1-methyl-1,3,4,8-tetrahydro-2H-[1,4]oxazepino[6,7-e]indole tert-Butyl 1-methyl-1,3,4,8-tetrahydro-2H-[1,4]oxazepino[6,7-e]indole-2-carboxylate (Intermediate 42, 25 mg, 0.083 mmol) was dissolved in DMF (1 mL) and sodium hydride (60% in mineral oil, 4.0 mg, 0.17 mol) was added. The reaction mixture was stirred at room temperature for 15 minutes before 1,2-dimethylimidazole-4-sulfonyl chloride (22 mg, 0.11 mmol) was added. The reaction mixture was allowed to stir at room temperature overnight. The reaction was quenched by addition of water and the crude product was purified by preparative HPLC (XTerra C18, 50 mM NH$_4$HCO$_3$ pH 10-CH$_3$CN) to give tert-butyl 8-[(1,2-dimethyl-1H-imidazol-4-yl)sulfonyl]-1-methyl-1,3,4,8-tetrahydro-2H-[1,4]oxazepino[6,7-e]indole-2-carboxylate (5 mg) which was dissolved in DCM (1 mL) and TFA (1 mL) was added. The reaction mixture was stirred at room temperature for 1 hour and the solvent was removed under reduced pressure. The crude material was purified by preparative HPLC (XTerra C18, 50 mM NH$_4$HCO$_3$ pH 10-CH$_3$CN) to give the title compound (2 mg). MS m/z 361 [M+H]$^+$.

Biological Tests

The ability of a compound according to the invention to bind to a 5-HT$_6$ receptor, and to be pharmaceutically useful, can be determined using in vivo and in vitro assays known in the art.

(a) 5-HT$_6$ Receptor Binding Assay

Binding affinity experiments for the human 5-HT$_6$ receptor are performed in HEK293 cells transfected with 5-HT$_6$ receptor using [$^3$H]-LSD as labeled ligand according to the general method as described by Boess F. G et al. Neuropharmacology 36(4/5) 713-720, 1997.

Materials

Cell Culture

The HEK-293 cell line transfected with the human 5-HT$_6$ receptor was cultured in Dulbeccos Modified Eagles Medium containing 5% dialyzed foetal bovine serum, (Gibco BRL 10106-169), 0.5 mM sodium pyruvate and 400 µg/ml Geneticin (G-418) (Gibco BRL10131-019). The cells were passaged 1:10, twice a week.

Chemicals

The radioligand [$^3$H] LSD 60-240 Ci/mmol, obtained from Amersham Pharmacia Biotech, (Buckinghamshire, England) was in ethanol and stored at −20° C. The compounds were dissolved in 100% DMSO and diluted with binding buffer.

Disposable

Compounds were diluted in Costar 96 well V-bottom polypropylene plates (Corning Inc. Costar, N.Y., USA). Samples were incubated in Packard Optiplate (Packard Instruments B.V., Groningen, The Netherlands). The total amount of added radioligand was measured in Packard 24-well Barex plates (Packard Instruments B.V., Groningen, The Netherlands) in the presence of Microscint™ 20 scintillation fluid (Packard Bioscience, Meriden, Conn., USA).

Buffer

The binding buffer consisted of 20 mM HEPES, 150 mM NaCl, 10 mM MgCl$_2$, and 1 mM, EDTA, pH 7.4.

Methods

Membrane Preparation

Cells were grown to approximately 90% confluence on 24.5×24.5 mm culture dishes. The medium was aspirated, and after rinsing with ice-cold PBS, the cells were scraped off using 25 ml Tris buffer (50 mM Tris-HCl, 1 mM EDTA, 1 mM EGTA, pH 7.4) and a window scraper. The cells were then broken with a Polytron homogeniser, and remaining particulate matter was removed by low-speed centrifugation, 1000×g for 5 min. Finally, the membranes were collected by high-speed centrifugation (20000×g), suspended in binding buffer, and frozen in aliquots at −70° C.

Radioligand Binding

Frozen cell membranes were thawed, immediately rehomogenized with a Polytron homogenizer, and coupled to SPA wheat germ agglutinin beads (Amersham Life Sciences, Cardiff, England) for 30 min under continuous shaking of the tubes. After coupling, the beads were centrifuged for 10 minutes at 1000 g, and subsequently suspended in 20 ml of binding buffer per 96-well plate The binding reaction was then initiated by adding radioligand and test compounds to the bead-membrane suspension. Following incubation at room temperature, the assay plates were subjected to scintillation counting.

The original SPA method was followed except for that membranes were prepared from HEK293 cells expressing the human 5-HT$_6$ receptor instead of from HeLa cells (Dinh D M, Zaworski P G, Gill G S, Schlachter S K, Lawson C F, Smith M W. Validation of human 5-HT$_6$ receptors expressed in HeLa cell membranes: saturation binding studies, pharmacological profiles of standard CNS agents and SPA development. (The Upjohn Company Technical Report 7295-95-064 1995; 27 December). The specific binding of [$^3$H]-LSD was saturable, while the non-specific binding increased linearly with the concentration of added radioligand. [$^3$H]-LSD bound with high affinity to 5-HT$_6$ receptors. The K$_d$ value was estimated to 2.6±0.2 nM based on four separate experiments.

The total binding at 3 nM of [$^3$H]-LSD, the radioligand concentration used in the competition experiments, was typically 6000 dpm, and the specific binding more than 70%. 5-HT caused a concentration dependent inhibition of [$^3$H]-LSD binding with an over all average Ki value of 236 nM when tested against two different membrane preparations. The inter assay variability over three experiments showed a CV of 10% with an average K$_i$ values of 173 nM (SD 30) and a Hill coefficient of 0.94 (SD 0.09). The intra assay variation was 3% (n=4). All unlabelled ligands displaced the specific binding of [$^3$H]-LSD in a concentration-dependent manner, albeit at different potencies. The rank order of affinity for the 5-HT$_6$ receptor of reference compounds was methiothepin (Ki 2 nM)>mianserin (190 nM)≈5-HT (236 nM)>methysergide (482 nM)>mesulergine (1970 nM).

Protein Determination

Protein concentrations were determined with BioRad Protein Assay (Bradford M M. A rapid and sensitive method for the quantitation of microgram quantities of protein utilizing the principle of protein-dye binding. Anal. Biochem. 1976; 72:248-54). Bovine serum albumin was used as standard.

Scintillation Counting

The radioactivity was determined in a Packard Top-Count™ scintillation counter (Packard Instruments, Meriden, Conn., USA) at a counting efficiency of approximately 20%. The counting efficiency was determined in separate sets of experiments.

Saturation Experiments

At least 6 concentrations in duplicates of radioligand (0.1-20 nM of [$^3$H]-LSD) were used in saturation experiments. The specific binding was calculated as the difference between total binding and non-specific binding, which was determined as the binding of radioligand in the presence of 5 µM lisuride. B$_{max}$ and the dissociation constant, K$_d$, were determined from the non-linear regression analysis using equation 1. L$_u$ is the unbound concentration of radioligand, and is y is the amount bound.

$$y = \frac{B_{max} \cdot Lu}{Lu + Kd} \quad \text{(equation 1)}$$

Competition Experiments

Total- and non-specific binding of radioligand was defined in eight replicates of each. Samples containing test compound were run in duplicate at 11 concentrations. Incubations were carried out at room temperature for 3 hours. The IC$_{50}$ value, i.e. the concentration of test compound that inhibited 50% of the specific binding of radioligand, was determined with non linear regression analysis and the K$_i$ value was calculated using equation 2 [Cheng Y. C. Biochem. Pharmacol. 22, 3099-3108, 1973].

$$Ki = \frac{IC_{50}}{1 + \frac{L}{K_d}} \quad \text{(equation 2)}$$

L=concentration of radioligand
K$_d$=Affinity of radioligand (b) 5-HT$_6$ Intrinsic Activity Assay Antagonists to the human 5-HT$_6$ receptor were characterized by measuring inhibition of 5-HT induced increase in cAMP in HEK 293 cells expressing the human 5-HT$_6$ receptor (see Boess et al. (1997) Neuropharmacology 36: 713-720). Briefly, HEK293/5-HT$_6$ cells were seeded in polylysine coated 96-well plates at a density of 25,000/well and grown in DMEM (Dulbecco's Modified Eagle Medium) (without phenol-red) containing 5% dialyzed Foetal Bovine Serum for 48 h at 37° C. in a 5% CO$_2$ incubator. The medium was then aspirated and replaced by 0.1 ml assay medium (Hanks Balance Salt Solution containing 20 mM HEPES, 1.5 mM isobutylmethylxanthine and 1 mg/ml bovine serum albumin). After addition of test substances, 50 µl dissolved in assay medium, the cells were incubated for 10 min at 37° C. in a 5% CO$_2$ incubator. The medium was again aspirated and the cAMP content was determined using a radioactive cAMP kit (Amersham Pharmacia Biotech, BIOTRAK RPA559). The potency of antagonists was quantified by determining the concentration that caused 50% inhibition of 5-HT (at [5-HT]=8 times EC$_{50}$) evoked increase in cAMP, using the formula IC$_{50,corr}$=IC$_{50}$/(1+[5HT]/EC$_{50}$).

The compounds in accordance with the invention have a selective affinity to human 5-HT$_6$ receptors with K$_i$ and IC$_{50,coor}$ values between 0.5 nM and 5 µM or display a % inhibition of [$^3$H]-LSD≧20% at 50 nM and are antagonists, agonists or partial agonists at the human 5-HT$_6$ receptor (see Tables II and III). The compounds show good selectivity over human 5-HT$_{1a}$, 5-HT$_{1b}$, 5-HT$_{2a}$, 5-HT$_{2b}$, and 5-HT$_{2c}$ receptors.

TABLE II

Binding affinity (K$_i$) at the human 5-HT$_6$ receptor

| Example | K$_i$ (nM) |
| --- | --- |
| 5 | 2 |
| 10 | 1 |
| 49 | 2 |

TABLE III

Antagonist potency at the human 5-HT$_6$ receptor. (fKi = IC$_{50,corr}$).

| Example | fK$_i$ (nM) |
| --- | --- |
| 5 | 3 |
| 10 | 1 |
| 49 | 5 |

(c) In vivo Assay of Reduction of Food Intake

For a review on serotonin and food intake, see Blundell, J. E. and Halford, J. C. G. (1998) Serotonin and Appetite Regulation. Implications for the Pharmacological Treatment of Obesity. CNS Drugs 9:473-495.

Obese (ob/ob) mouse is selected as the primary animal model for screening as this mutant mouse consumes high amounts of food resulting in a high signal to noise ratio. To further substantiate and compare efficacy data, the effect of the compounds on food consumption is also studied in wild type (C57BL/6J) mice. The amount of food consumed during 15 hours of infusion of compounds is recorded.

Male mice (obese C57BL/6JBom-Lep$^{ob}$ and lean wild-type C57BL/6JBom; Bomholtsgaard, Denmark) 8-9 weeks with an average body weight of 50 g (obese) and 25 g (lean) are used in all the studies. The animals are housed singly in cages at 23±1° C., 40-60% humidity and have free access to water and standard laboratory chow. The 12/12-h light/dark cycle is set to lights off at 5 p.m. The animals are conditioned for at least one week before start of study.

The test compounds are dissolved in solvents suitable for each specific compound such as cyclodextrin, cyclodextrin/methane sulphonic acid, polyethylene glycol/methane sulphonic acid, saline. Fresh solutions are made for each study. Doses of 30, 50 and 100 mg kg$^{-1}$day$^{-1}$ are used. The purity of the test compounds is of analytical grade.

The animals are weighed at the start of the study and randomized based on body weight. Alzet osmotic minipumps (Model 2001D; infusion rate 8 µl/h) are used and loaded essentially as recommended by the Alzet technical information manual (Alza Scientific Products, 1997; Theeuwes, F. and Yam, S. I. Ann. Biomed. Eng. 4(4). 343-353, 1976). Continuous subcutaneous infusion with 24 hours duration is used. The minipumps are either filled with different concentrations of test compounds dissolved in vehicle or with only vehicle solution and maintained in vehicle pre-warmed to 37° C. (approx. 1 h). The minipumps are implanted subcutaneously in the neck/back region under short acting anesthesia (metofane/enflurane). This surgical procedure lasts approximately 5 min.

The weight of the food pellets are measured at 5 p.m. and at 8 p.m. for two days before (baseline) and one day after the implantation of the osmotic minipumps. The weigh-in is performed with a computer assisted Mettler Toledo PR 5002 balance. Occasional spillage is corrected for. At the end of the study the animals are killed by neck dislocation and trunk blood sampled for later analysis of plasma drug concentrations.

The plasma sample proteins are precipitated with methanol, centrifuged and the supernatant is transferred to HPLC vials and injected into the liquid chromatography/mass spectrometric system. The mass spectrometer is set for electrospray positive ion mode and Multiple Reaction Monitoring. A linear regression analysis of the standards forced through the origin is used to calculate the concentrations of the unknown samples.

Food consumption for 15 hours is measured for the three consecutive days and the percentage of basal level values is derived for each animal from the day before and after treatment. The values are expressed as mean±SD and ±SEM from eight animals per dose group. Statistical evaluation is performed by Kruskal-Wallis one-way ANOVA using the percent basal values. If statistical significance is reached at the level of p<0.05, Mann-Whitney U-test for statistical comparison between control and treatment groups is performed.

The invention claimed is:
1. The compound of the formula (I):

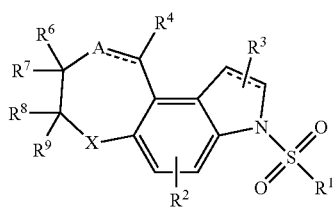

(I)

wherein:
⸗ represents a single bond or a double bond;
A is N or NR$^5$;
X is O, S, N—H or N—C$_{1-6}$-alkyl;
R$^1$ is a group selected from:

(a) C$_{1-6}$-alkyl,
(b) C$_{3-7}$-cycloalkyl,
(c) C$_{3-6}$-alkenyl,
(d) aryl,
(e) aryl-C$_{2-6}$-alkenyl,
(f) aryl-C$_{1-6}$-alkyl,
(g) heteroaryl,
(h) heteroaryl-C$_{2-6}$-alkenyl, and
(i) heteroaryl-C$_{1-6}$-alkyl,
wherein any heteroaryl or aryl residue, alone or as part of another group, is optionally independently substituted in one or more positions with a substituent selected from:
(a) halogen,
(b) C$_{1-6}$-alkyl,
(c) fluoro-C$_{1-6}$-alkyl,
(d) C$_{3-7}$-cycloalkyl,
(e) methyl-C$_{3-7}$-cycloalkyl,
(f) fluoro-C$_{3-7}$-cycloalkyl,
(g) C$_{2-6}$-alkenyl,
(h) fluoro-C$_{2-6}$-alkenyl,
(i) ethynyl;
(j) hydroxy-C$_{1-4}$-alkyl,
(k) hydroxy,
(l) C$_{1-6}$-alkoxy
(m) fluoro-C$_{1-6}$-alkoxy
(n) C$_{3-7}$-cycloalkoxy
(o) methyl-C$_{3-7}$-cycloalkoxy
(p) fluoro-C$_{3-7}$-cycloalkoxy
(q) —SCF$_3$,
(r) —SCF$_2$H,
(s) —SO$_2$NR$^{10}$R$^{10}$,
(t) —S(O)$_e$R$^{11}$, wherein e is 0, 1, 2 or 3,
(u) —CN,
(v) —NR$^{10}$R$^{10}$,
(w) —NHSO$_2$R$^{11}$,
(x) —NR$^{12}$COR$^{11}$,
(y) —NO$_2$,
(z) —CONR$^{10}$R$^{10}$,
(aa) —CO—R$^{11}$,
(bb) —COOH,
(cc) C$_{1-6}$-alkoxycarbonyl,
(dd) aryl,
(ee) heteroaryl,
(ff) aryloxy, and
(gg) heteroaryloxy,
wherein any (dd) aryl or (ee) heteroaryl, alone or as part of another group, is optionally substituted in one or more positions with a substituent selected from:
(a) halogen,
(b) C$_{1-4}$-alkyl,
(c) C$_{1-4}$-alkylthio,
(d) C$_{1-4}$-alkoxy,
(e) —CF$_3$,
(f) —CN, and
(g) hydroxymethyl;
R$^2$ is a group selected from:
(a) hydrogen
(b) halogen,
(c) C$_{1-6}$-alkyl,
(d) fluoro-C$_{1-6}$-alkyl,
(e) C$_{3-7}$-cycloalkyl,
(f) methyl-C$_{3-7}$-cycloalkyl,
(g) fluoro-C$_{3-7}$-cycloalkyl,
(h) C$_{2-6}$-alkenyl,
(i) fluoro-C$_{2-6}$-alkenyl,
(j) ethynyl,
(k) hydroxy-C$_{1-4}$-alkyl, (l) hydroxy,
(m) $C_{1-6}$-alkoxy,
(n) fluoro-$C_{1-6}$-alkoxy,
(o) $C_{3-7}$-cycloalkoxy,
(p) methyl-$C_{3-7}$-cycloalkoxy,
(q) fluoro-$C_{3-7}$-cycloalkoxy,
(r) —$SCF_3$,
(s) —$SCF_2H$,
(t) —$SO_2NR^{10}R^{10}$,
(u) —$S(O)_eR^{11}$, wherein e is 0, 1, 2 or 3,
(v) —CN,
(w) —$NR^{10}R^{10}$,
(x) —$NR^{12}SO_2R^{11}$,
(y) —$NR^{12}COR^{11}$,
(z) —$NO_2$,
(aa) —$CONR^{10}R^{10}$,
(bb) —$OCONR^{10}R^{10}$,
(cc) —CO—$R^{11}$,
(dd) —COOH, and
(ee) $C_{1-6}$-alkoxycarbonyl;
$R^3$ is a group selected from:
(a) hydrogen,
(b) halogen,
(c) $C_{1-6}$-alkyl,
(d) $C_{3-7}$-cycloalkyl,
(e) hydroxy-$C_{1-4}$-alkyl,
(f) $C_{3-7}$-cycloalkyl-hydroxy-$C_{1-4}$-alkyl
(g) $C_{1-2}$-alkoxy-$C_{1-4}$-alkyl
(h) —$COOR^{12}$,
(i) —$CONR^{10}R^{10}$,
(j) —CO—$R^{11}$,
(k) —CN,
(l) aryl, and
(m) heteroaryl,
wherein any heteroaryl or aryl residue is optionally independently substituted in one or more positions with a substituent selected from:
(a) halogen,
(b) $C_{1-4}$-alkyl,
(c) $C_{1-4}$-alkylthio,
(d) $C_{1-4}$-alkoxy,
(e) —$CF_3$,
(f) —CN, and
(g) hydroxymethyl;
$R^4$ is a group selected from:
(a) hydrogen,
(b) $C_{1-4}$-alkyl,
(c) fluoro-$C_{1-4}$-alkyl,
(d) $C_{3-5}$-cycloalkyl,
(e) fluoro-$C_{3-5}$-cycloalkyl,
(f) hydroxy-$C_{1-4}$-alkyl, and
(g) cyano;
$R^5$ is a group selected from:
(a) hydrogen,
(b) $C_{1-4}$-alkyl,
(c) fluoro-$C_{1-4}$-alkyl,
(d) 2-cyanoethyl,
(e) hydroxy-$C_{2-4}$-alkyl,
(f) $C_{3-4}$-alkenyl,
(g) $C_{3-4}$-alkynyl,
(h) $C_{3-7}$-cycloalkyl,
(i) methyl-$C_{3-7}$-cycloalkyl,
(j) fluoro-$C_{3-7}$-cycloalkyl,
(k) $C_{3-4}$-cycloalkyl-$C_{1-4}$-alkyl, and
(l) $C_{1-4}$-alkoxy-$C_{2-4}$-alkyl, or $R^5$ and one of $R^6$, $R^7$, $R^8$, or $R^9$ groups together with the atoms to which they are attached form a heterocyclic ring and the other three of $R^6$, $R^7$, $R^8$ or $R^9$ are hydrogen;
$R^6$, $R^7$, $R^8$, and $R^9$ are each independently selected from:
(a) hydrogen,
(b) $C_{1-6}$-alkyl,
(c) fluoro-$C_{1-6}$-alkyl,
(d) $C_{3-7}$-cycloalkyl, and
(e) hydroxy-$C_{1-4}$-alkyl,
with the proviso that three of $R^6$, $R^7$, $R^8$ and $R^9$ are hydrogen unless at least two of $R^6$, $R^7$, $R^8$ and $R^9$ are methyl and the remainder of them are hydrogen,
two of the $R^6$, $R^7$, $R^8$, or $R^9$ groups together with the atoms to which they are attached form a carbocyclic or heterocyclic ring and the other two of $R^6$, $R^7$, $R^8$ or $R^9$ are hydrogen, or
one of $R^6$, $R^7$, $R^8$, or $R^9$ groups and $R^5$ together with the atoms to which they are attached form a heterocyclic ring and the other three of $R^6$, $R^7$, $R^8$ or $R^9$ are hydrogen;
$R^{10}$ is each independently a group selected from:
(a) hydrogen,
(b) $C_{1-6}$-alkyl,
(c) fluoro-$C_{2-6}$-alkyl, and
(d) $C_{3-7}$-cycloalkyl, or
two $R^{10}$ groups together with the nitrogen to which they are attached form a heterocyclic ring optionally substituted with methyl;
$R^{11}$ is each independently a group selected from:
(a) hydrogen,
(b) $C_{1-6}$-alkyl,
(c) fluoro-$C_{1-6}$-alkyl,
(d) $C_{3-7}$-cycloalkyl,
(e) methyl-$C_{3-7}$-cycloalkyl,
(f) aryl, and
(g) heteroaryl,
wherein any heteroaryl or aryl residue is optionally independently substituted in one or more positions with a substituent selected from:
(a) halogen,
(b) $C_{1-4}$-alkyl,
(c) $C_{1-4}$-alkylthio,
(d) $C_{1-4}$-alkoxy,
(e) —$CF_3$,
(f) —CN, and
(g) hydroxymethyl,
$R^{12}$ is each independently a group selected from:
(a) hydrogen,
(b) $C_{1-6}$-alkyl,
(c) fluoro-$C_{1-6}$-alkyl,
(d) $C_{3-7}$-cycloalkyl, and
(e) hydroxy-$C_{1-4}$-alkyl,
or $R^{11}$ and $R^{12}$ together with the atoms to which they are attached form a lactam ring when present in the group $NR^{12}COR^{11}$, or $R^{11}$ and $R^{12}$ together with the atoms to which they are attached form a sultam ring when present in the group $NR^{12}SO_2R^{11}$;
or a pharmaceutically acceptable salt, geometrical isomer, tautomer, or an optical isomer thereof.

2. The compound according to claim 1, which is of formula (II):

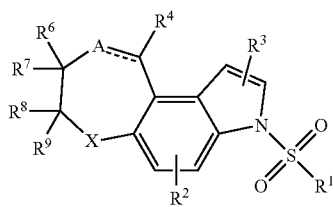

wherein
⸻ represents a single bond or a double bond;
A is N or $NR^5$;
X is O, S, N—H or N—$C_{1-6}$-alkyl;
$R^1$ is a group selected from:
  (a) $C_{1-6}$-alkyl,
  (b) $C_{3-7}$-cycloalkyl,
  (c) $C_{3-6}$-alkenyl,
  (d) aryl,
  (e) aryl-$C_{2-6}$-alkenyl,
  (f) aryl-$C_{1-6}$-alkyl,
  (g) heteroaryl,
  (h) heteroaryl-$C_{2-6}$-alkenyl, and
  (i) heteroaryl-$C_{1-6}$-alkyl,
wherein any heteroaryl or aryl residue, alone or as part of another group, is optionally independently substituted in one or more positions with a substituent selected from:
  (a) halogen,
  (b) $C_{1-6}$-alkyl,
  (c) fluoro-$C_{1-6}$-alkyl,
  (d) $C_{3-7}$-cycloalkyl,
  (e) methyl-$C_{3-7}$-cycloalkyl,
  (f) fluoro-$C_{3-7}$-cycloalkyl,
  (g) $C_{2-6}$-alkenyl,
  (h) fluoro-$C_{2-6}$-alkenyl,
  (i) ethynyl;
  (j) hydroxy-$C_{1-4}$-alkyl,
  (k) hydroxy,
  (l) $C_{1-6}$-alkoxy
  (m) fluoro-$C_{1-6}$-alkoxy
  (n) $C_{3-7}$-cycloalkoxy
  (o) methyl-$C_{3-7}$-cycloalkoxy
  (p) fluoro-$C_{3-7}$-cycloalkoxy
  (q) —$SCF_3$,
  (r) —$SCF_2H$,
  (s) —$SO_2NR^{10}R^{10}$,
  (t) —$S(O)_eR^{11}$, wherein e is 0, 1, 2 or 3,
  (u) —CN,
  (v) —$NR^{10}R^{10}$,
  (w) —$NHSO_2R^{11}$,
  (x) —$NR^{12}COR^{11}$,
  (y) —$NO_2$,
  (z) —$CONR^{10}R^{10}$,
  (aa) —CO—$R^{11}$,
  (bb) —COOH,
  (cc) $C_{1-6}$-alkoxycarbonyl,
  (dd) aryl,
  (ee) heteroaryl,
  (ff) aryloxy, and
  (gg) heteroaryloxy,
wherein any (dd) aryl or (ee) heteroaryl, alone or as part of another group, is optionally substituted in one or more positions with a substituent selected from:
  (a) halogen,
  (b) $C_{1-4}$-alkyl,
  (c) $C_{1-4}$-alkylthio,
  (d) $C_{1-4}$-alkoxy,
  (e) —$CF_3$,
  (f) —CN, and
  (g) hydroxymethyl;
$R^2$ is a group selected from:
  (a) hydrogen
  (b) halogen,
  (c) $C_{1-6}$-alkyl,
  (d) fluoro-$C_{1-6}$-alkyl,
  (e) $C_{3-7}$-cycloalkyl,
  (f) methyl-$C_{3-7}$-cycloalkyl,
  (g) fluoro-$C_{3-7}$-cycloalkyl,
  (h) $C_{2-6}$-alkenyl,
  (i) fluoro-$C_{2-6}$-alkenyl,
  (j) ethynyl,
  (k) hydroxy-$C_{1-4}$-alkyl,
  (l) hydroxy,
  (m) $C_{1-6}$-alkoxy,
  (n) fluoro-$C_{1-6}$-alkoxy,
  (o) $C_{3-7}$-cycloalkoxy,
  (p) methyl-$C_{3-7}$-cycloalkoxy,
  (q) fluoro-$C_{3-7}$-cycloalkoxy,
  (r) —$SCF_3$,
  (s) —$SCF_2H$,
  (t) —$SO_2NR^{10}R^{10}$,
  (u) —$S(O)_eR^{11}$, wherein e is 0, 1, 2 or 3,
  (v) —CN,
  (w) —$NR^{10}R^{10}$,
  (x) —$NR^{12}SO_2R^{11}$,
  (y) —$NR^{12}COR^{11}$,
  (z) —$NO_2$,
  (aa) —$CONR^{10}R^{10}$,
  (bb) —$CONR^{10}R^{10}$,
  (cc) —CO—$R^{11}$,
  (dd) —COOH, and
  (ee) $C_{1-6}$-alkoxycarbonyl;
$R^3$ is a group selected from:
  (a) hydrogen,
  (b) halogen,
  (c) $C_{1-6}$-alkyl,
  (d) $C_{3-7}$-cycloalkyl,
  (e) hydroxy-$C_{1-4}$-alkyl,
  (f) $C_{3-7}$-cycloalkyl-hydroxy-$C_{1-4}$-alkyl
  (g) $C_{1-2}$-alkoxy-$C_{1-4}$-alkyl
  (h) —$COOR^{12}$,
  (i) —$CONR^{10}R^{10}$,
  (j) —CO—$R^{11}$,
  (k) —CN,
  (l) aryl, and
  (m) heteroaryl,
wherein any heteroaryl or aryl residue is optionally independently substituted in one or more positions with a substituent selected from:
  (a) halogen,
  (b) $C_{1-4}$-alkyl,
  (c) $C_{1-4}$-alkylthio,
  (d) $C_{1-4}$-alkoxy,
  (e) —$CF_3$,
  (f) —CN, and
  (g) hydroxymethyl;
$R^4$ is a group selected from:
  (a) hydrogen,
  (b) $C_{1-4}$-alkyl,
  (c) fluoro-$C_{1-4}$-alkyl, (d) $C_{3-5}$-cycloalkyl,
(e) fluoro-$C_{3-5}$-cycloalkyl,
(f) hydroxy-$C_{1-4}$-alkyl, and
(g) cyano;

$R^5$ is a group selected from:
(a) hydrogen,
(b) $C_{1-4}$-alkyl,
(c) fluoro-$C_{1-4}$-alkyl,
(d) 2-cyanoethyl,
(e) hydroxy-$C_{2-4}$-alkyl,
(f) $C_{3-4}$-alkenyl,
(g) $C_{3-4}$-alkynyl,
(h) $C_{3-7}$-cycloalkyl,
(i) methyl-$C_{3-7}$-cycloalkyl
(j) fluoro-$C_{3-7}$-cycloalkyl,
(k) $C_{3-4}$-cycloalkyl-$C_{1-4}$-alkyl, and
(l) $C_{1-4}$-alkoxy-$C_{2-4}$-alkyl, or
$R^5$ and one of $R^6$, $R^7$, $R^8$, or $R^9$ groups together with the atoms to which they are attached form a heterocyclic ring and the other three of $R^6$, $R^7$, $R^8$ or $R^9$ are hydrogen;

$R^6$, $R^7$, $R^8$, and $R^9$ are each independently selected from:
(a) hydrogen,
(b) $C_{1-6}$-alkyl,
(c) fluoro-$C_{1-6}$-alkyl,
(d) $C_{3-7}$-cycloalkyl, and
(e) hydroxy-$C_{1-4}$-alkyl,
with the proviso that three of $R^6$, $R^7$, $R^8$ and $R^9$ are hydrogen unless at least two of $R^6$, $R^7$, $R^8$ and $R^9$ are methyl and the remainder of them are hydrogen,
two of the $R^6$, $R^7$, $R^8$, or $R^9$ groups together with the atoms to which they are attached form a carbocyclic or heterocyclic ring and the other two of $R^6$, $R^7$, $R^8$ or $R^9$ are hydrogen, or
one of $R^6$, $R^7$, $R^8$, or $R^9$ groups and $R^5$ together with the atoms to which they are attached form a heterocyclic ring and the other three of $R^6$, $R^7$, $R^8$ or $R^9$ are hydrogen;

$R^{10}$ is each independently a group selected from:
(a) hydrogen,
(b) $C_{1-6}$-alkyl,
(c) fluoro-$C_{2-6}$-alkyl, and
(d) $C_{3-7}$-cycloalkyl, or
two $R^{10}$ groups together with the nitrogen to which they are attached form a heterocyclic ring optionally substituted with methyl;

$R^{11}$ is each independently a group selected from:
(a) hydrogen,
(b) $C_{1-6}$-alkyl,
(c) fluoro-$C_{1-6}$-alkyl,
(d) $C_{3-7}$-cycloalkyl,
(e) methyl-$C_{3-7}$-cycloalkyl,
(f) aryl, and
(g) heteroaryl,
wherein any heteroaryl or aryl residue is optionally independently substituted in one or more positions with a substituent selected from:
(a) halogen,
(b) $C_{1-4}$-alkyl,
(c) $C_{1-4}$-alkylthio,
(d) $C_{1-4}$-alkoxy,
(e) —$CF_3$,
(f) —CN, and
(g) hydroxymethyl, $R^{12}$ is each independently a group selected from:
(a) hydrogen,
(b) $C_{1-6}$-alkyl, (c) fluoro-$C_{1-6}$-alkyl,
(d) $C_{3-7}$-cycloalkyl, and
(e) hydroxy-$C_{1-4}$-alkyl,
or $R^{11}$ and $R^{12}$ together with the atoms to which they are attached form a lactam ring when present in the group $NR^{12}COR^{11}$, or $R^{11}$ and $R^{12}$ together with the atoms to which they are attached form a sultam ring when present in the group $NR^{12}SO_2R^{11}$.

3. The compound according to claim 2, wherein:
X=O;
$R^1$ is selected from aryl and heteroaryl, wherein any heteroaryl or aryl residue is optionally independently substituted in one or more positions with a substituent selected from:
(a) halogen,
(b) $C_{1-3}$-alkyl,
(c) trifluoromethyl,
(d) methoxy,
(e) trifluoromethoxy,
(f) methylsulfonyl,
(g) —CN, and
(h) phenyl;

$R^2$ is a group selected from:
(a) hydrogen
(b) halogen,
(c) $C_{1-6}$-alkyl, and
(d) $C_{1-6}$ alkoxy;

$R^3$ is a group selected from:
(a) hydrogen,
(b) halogen,
(c) $C_{1-6}$-alkyl,
(d) hydroxy-$C_{1-4}$-alkyl,
(e) $C_{3-7}$-cycloalkyl-hydroxy-$C_{1-4}$-alkyl, and
(f) —CO—$C_{1-6}$-alkyl;

$R^4$ is a group selected from hydrogen and $C_{1-4}$-alkyl;
$R^5$ is selected from hydrogen, $C_{1-3}$-alkyl and fluoro-$C_{1-3}$-alkyl; or
$R^5$ and one of $R^6$ and $R^8$ together with the nitrogen and carbon atoms to which they are attached form a pyrrolidine ring, provided that $R^7$ and $R^9$ both are hydrogen;
$R^6$ is hydrogen, or together with $R^5$ and the nitrogen and carbon atoms to which they are attached form a pyrrolidine ring, provided that $R^7$ and $R^9$ both are hydrogen;
$R^7$ is selected from hydrogen and methyl:
$R^8$ is hydrogen, or together with $R^5$ and the nitrogen and carbon atoms to which they are attached together form a pyrrolidine ring, provided that $R^7$ and $R^9$ both are hydrogen;
$R^9$ is selected from hydrogen and methyl.

4. The compound according to claim 3, wherein:
$R^1$ is selected from phenyl, naphthyl, pyridinyl, isoxazolyl, imidazolyl, 1,4-benzodioxinyl, benzofuranyl, furanyl, 1,3-benzothiazolyl, chromanyl, thienyl and benzothienyl, each of which is optionally independently substituted in one or two positions with a substituent selected from
(a) fluorine
(b) chlorine,
(c) $C_{1-3}$-alkyl,
(d) trifluoromethyl,
(e) methoxy,
(f) trifluoromethoxy,
(g) methylsulfonyl,
(h) —CN, and
(i) phenyl
$R^2$ is hydrogen, fluoro, methyl or methoxy;

R³ is hydrogen, chloro, methyl, 1-hydroxy-ethyl, 1-hydroxy-1-methyl-ethyl, acetyl, isobutyryl or cyclopropyl-hydroxymethyl;

R⁴ is selected from hydrogen, methyl and isopropyl;

R⁵ is selected from hydrogen, methyl, ethyl, isopropyl, and 2-fluoroeth-1-yl; or R⁵ and one of R⁶ and R⁸ together with the nitrogen and carbon atoms to which they are attached form a pyrrolidine ring, provided that R⁷ and R⁹ both are hydrogen;

R⁶ is hydrogen or R⁶ together with R⁵ and the nitrogen and carbon atoms to which they are attached form a pyrrolidine ring, provided that R⁷ and R⁹ both are hydrogen;

R⁷ is selected from hydrogen and methyl;

R⁸ is hydrogen or together with R⁵ and the nitrogen and carbon atoms to which they are attached together form a pyrrolidine ring, provided that R⁷ and R⁹ both are hydrogen;

R⁹ is selected from hydrogen and methyl.

5. The compound according to claim 4, wherein
R¹ is selected from phenyl, 1-naphthyl, 2-naphthyl, 3-pyridinyl, 4-isoxazolyl, 4-imidazolyl, 1,4-benzodioxin-6-yl, 2-benzofuranyl, 3-furyl, 1,3-benzothiazol-6-yl, 6-chromenyl, 2-thienyl, 3-thienyl, 2-benzothienyl, and 3-benzothienyl each of which is optionally independently substituted in one or two positions with a substituent selected from
    (a) fluorine,
    (b) chlorine,
    (c) methyl,
    (d) propyl,
    (e) isopropyl,
    (f) trifluoromethyl,
    (g) methoxy,
    (h) trifluoromethoxy,
    (i) methylsulfonyl,
    (j) —CN, and
    (k) phenyl.

6. The compound according to claim 5, which is selected from:
   2,5-methylene-9-(phenylsulfonyl)-1,2,3,4,5,9-hexahydro[1,5]oxazocino[3,2-e]indole;
   2,4-dimethyl-8-(phenylsulfonyl)-1,3,4,8-tetrahydro-2H-[1,4]oxazepino[6,7-e]indole;
   2-isopropyl-8-(phenylsulfonyl)-1,3,4,8-tetrahydro-2H-[1,4]oxazepino[6,7-e]indole;
   2-ethyl-8-(phenylsulfonyl)-1,3,4,8-tetrahydro-2H-[1,4]oxazepino[6,7-e]indole;
   2-methyl-8-(phenylsulfonyl)-1,3,4,8-tetrahydro-2H-[1,4]oxazepino[6,7-e]indole;
   8-(2,3-dihydro-1,4-benzodioxin-6-ylsulfonyl)-2-methyl-1,3,4,8-tetrahydro-2H-[1,4]oxazepino[6,7-e]indole;
   8-[(3,4-dimethoxyphenyl)sulfonyl]-2-methyl-1,3,4,8-tetrahydro-2H-[1,4]oxazepino[6,7-e]indole;
   8-(1-benzofuran-2-ylsulfonyl)-2-methyl-1,3,4,8-tetrahydro-2H-[1,4]oxazepino[6,7-e]indole;
   8-[(2,5-dimethyl-3-furyl)sulfonyl]-2-methyl-1,3,4,8-tetrahydro-2H-[1,4]oxazepino[6,7-e]indole;
   8-(1,3-benzothiazol-6-ylsulfonyl)-2-methyl-1,3,4,8-tetrahydro-2H-[1,4]oxazepino[6,7-e]indole;
   2-methyl-8-{1[4-(methylsulfonyl)phenyl]sulfonyl}-1,3,4,8-tetrahydro-2H-[1,4]oxazepino[6,7-e]indole;
   8-[(4-isopropylphenyl)sulfonyl]-2-methyl-1,3,4,8-tetrahydro-2H-[1,4]oxazepino[6,7-e]indole;
   8-[(2,2-dimethyl-3,4-dihydro-2H-chromen-6)sulfonyl]-2-methyl-1,3,4,8-tetrahydro-2H[1,4]oxazepino[6,7-e]indole;
   8-[(2-chloro-4-fluorophenyl)sulfonyl]-2-methyl-1,3,4,8-tetrahydro-2H-[1,4]oxazepino[6,7-e]indole;
   8-[(3,4-dichlorophenyl)sulfonyl]-2-methyl-1,3,4,8-tetrahydro-2H-[1,4]oxazepino[6,7-e]indole,
   8-[(4-fluorophenyl)sulfonyl]-2-methyl-1,3,4,8-tetrahydro-2H-[1,4]oxazepino[6,7-e]indole;
   8-[(2,6-difluorophenyl)sulfonyl]-2-methyl-1,3,4,8-tetrahydro-2H[1,4]oxazepino[6,7-e]indole;
   2-methyl-8-{[4-(trifluoromethoxy)phenyl]sulfonyl}-1,3,4,8-tetrahydro-2H-[1,4]oxazepino[6,7-e]indole;
   2-methyl-8-(2-naphthylsulfonyl)-1,3,4,8-tetrahydro-2H-[1,4]oxazepino[6,7-e]indole;
   8-[(3-chloro-4-methylphenyl)sulfonyl]-2-methyl-1,3,4,8-tetrahydro-2H-[1,4]oxazepino[6,7-e]indole;
   8-[(4,5-dichloro-2-thienyl)sulfonyl]-2-methyl-1,3,4,8-tetrahydro-2H-[1,4]oxazepino[6,7-e]indole;
   8-[(5-chloro-3-methyl-1-benzothien-2-yl)sulfonyl]-2-methyl-1,3,4,8-tetrahydro-2H-[1,4]oxazepino[6,7-e]indole;
   8-[(2,4-dichlorophenyl)sulfonyl]-2-methyl-1,3,4,8-tetrahydro-2H-[1,4]oxazepino[6,7-e]indole;
   8-1[4-fluoro-3-(trifluoromethyl)phenyl]sulfonyl1-2-methyl-1,3,4,8-tetrahydro-2H-[1,4]oxazepino[6,7-e]indole;
   2-methyl-8-(2-thienylsulfonyl)-1,3,4,8-tetrahydro-2H-[1,4]oxazepino[6,7-e]indole;
   2-methyl-8-[(4-methylphenyl)sulfonyl]-1,3,4,8-tetrahydro-2H-[1,4]oxazepino[6,7-e]indole;
   8-[(2-methoxy-5-methylphenyl)sulfonyl]-2-methyl-1,3,4,8-tetrahydro-2H-[1,4]oxazepino[6,7-e]indole;
   8-[(3-fluoro-4-methylphenyl)sulfonyl]-2-methyl-1,3,4,8-tetrahydro-2H-[1,4]oxazepino[6,7-e]indole;
   8-(1-benzothien-3-ylsulfonyl)-2-methyl-1,3,4,8-tetrahydro-2H-[1,4]oxazepino[6,7-e]indole;
   8-[(4-methoxyphenyl)sulfonyl]-2-methyl-1,3,4,8-tetrahydro-2H-[1,4]oxazepino[6,7-e]indole;
   2-methyl-8-{[4-(trifluoromethyl)phenyl]sulfonyl}-1,3,4,8-tetrahydro-2H-[1,4]oxazepino[6,7-e]indole;
   2-methyl-8-[(4-propylphenyl)sulfonyl]-1,3,4,8-tetrahydro-2H-[1,4]oxazepino[6,7-e]indole;
   3-chloro-4-[(2-methyl-1,2,3,4-tetrahydro-8H-[1,4]oxazepino[6,7-e]indol-8-yl)sulfonyl]benzonitrile;
   8-[(2,5-dimethyl-3-thienyl)sulfonyl]-2-methyl-1,3,4,8-tetrahydro-2H-[1,4]oxazepino[6,7-e]indole;
   2[(2-methyl-1,2,3,4-tetrahydro-8H-[1,4]oxazepino[6,7-e]indol-8-yl)sulfonyl]benzonitrile;
   2-methyl-1[2-methyl-8-(phenylsulfonyl)-1,3,4,8-tetrahydro-2H-[1,4]oxazepino[6,7-e]indol-9-yl]propan-1-one;
   1-[2-methyl-8-(phenylsulfonyl)-1,3,4,8-tetrahydro-2H-[1,4]oxazepino[6,7-e]indol-9-yl]ethanone;
   9-chloro-2-methyl-8-(phenylsulfonyl)-1,3,4,8-tetrahydro-2H-[1,4]oxazepino[6,7-e]indole;
   2[2-methyl-8-(phenylsulfonyl)-1,3,4,8-tetrahydro-2H-[1,4]oxazepino[6,7-e]indol-9-yl]propan-2-ol ;
   cyclopropyl[2-methyl-8-(phenylsulfonyl)-1,3,4,8-tetrahydro-2H-[1,4]oxazepino[6,7-e]indol-9-yl]methanol;
   1-[2-methyl-8-(phenylsulfonyl)-1,3,4,8-tetrahydro-2H-[1,4]oxazepino[6,7-e]indol-9-yl]ethanol ;
   10-chloro-2-methyl-8-(phenylsulfonyl)-1,3,4,8-tetrahydro-2H-[1,4]oxazepino[6,7-e]indole;
   (7aR)-3-(phenylsulfonyl)-3,7a,8,9,10,12-hexahydro-7H-pyrrolo[2',1':3,4][1,4]oxazepino[6,7-e]indole;
   (7aS)-3-(phenylsulfonyl)-3,7a,8,9,10,12-hexahydro-7H-pyrrolo[2',1':3,4][1,4]oxazepino[6,7-e]indole;
   (3S)-3-methyl-8-(phenylsulfonyl)-1,3,4,8-tetrahydro-2H-[1,4]oxazepino[6,7-e]indole;

(3S)-2,3-dimethyl-8-(phenylsulfonyl)-1,3,4,8-tetrahydro-2H[1,4]oxazepino[6,7-e]indole;
2,7-dimethyl-8-(phenylsulfonyl)-1,3,4,8-tetrahydro-2H-[1,4]oxazepino[6,7-e]indole;
6-methoxy-2-methyl-8-(phenylsulfonyl)-1,3,4,8-tetrahydro-2H-[1,4]oxazepino[6,7-e]indole;
8-(phenylsulfonyl)-1,3,4,8-tetrahydro-2H-[1,4]oxazepino[6,7-e]indole;
2-(2-fluoroethyl)-8-(phenylsulfonyl)-1,3,4,8-tetrahydro-2H-[1,4]oxazepino[6,7-e]indole;
8-[(2-methoxy-5-methylphenyl)sulfonyl]-1,3,4,8-tetrahydro-2H-[1,4]oxazepino[6,7-e]indole;
8[(2,4-dichlorophenyl)sulfonyl]-1,3,4,8-tetrahydro-2H-[1,4]oxazepino[6,7-e]indole;
8-{[3-(trifluoromethyl)phenyl]sulfonyl}-1,3,4,8-tetrahydro-2H-[1,4]oxazepino[6,7-e]indole;
8[(3,4-dimethoxyphenyl)sulfonyl]-1,3,4,8-tetrahydro-2H-[1,4]oxazepino[6,7-e]indole;
8-(2-naphthylsulfonyl)-1,3,4,8-tetrahydro-2H-[1,4]oxazepino[6,7-e]indole;
8[(2-methoxy-4-methylphenyl)sulfonyl]-1,3,4,8-tetrahydro-2H-[1,4]oxazepino[6,7-e]indole;
8[(4-propylphenyl)sulfonyl]-1,3,4,8-tetrahydro-2H-[1,4]oxazepino[6,7-e]indole;
8[(4-isopropylphenyl)sulfonyl]-1,3,4,8-tetrahydro-2H-[1,4]oxazepino[6,7-e]indole;
8-(1-benzofuran-2-ylsulfonyl)-1,3,4,8-tetrahydro-2H-[1,4]oxazepino[6,7-e]indole;
8[(2,5-dimethyl-3-thienyl)sulfonyl]-1,3,4,8-tetrahydro-2H-[1,4]oxazepino[6,7-e]indole;
8[(3-fluoro-4-methylphenyl)sulfonyl]-1,3,4,8-tetrahydro-2H-[1,4]oxazepino[6,7-e]indole;
8[(4-methoxyphenyl)sulfonyl]-1,3,4,8-tetrahydro-2H-[1,4]oxazepino[6,7-e]indole;
8[(2,5-dimethyl-3-furyl)sulfonyl]-1,3,4,8-tetrahydro-2H-[1,4]oxazepino[6,7-e]indole;
8[(2-methylphenyl)sulfonyl]-1,3,4,8-tetrahydro-2H-[1,4]oxazepino[6,7-e]indole;
8[(4-methylphenyl)sulfonyl]-1,3,4,8-tetrahydro-2H-[1,4]oxazepino[6,7-e]indole;
8-(2-thienylsulfonyl)-1,3,4,8-tetrahydro-2H-[1,4]oxazepino[6,7-e]indole;
8-{[2-(trifluoromethoxy)phenyl]sulfonyl}-1,3,4,8-tetrahydro-2H-[1,4]oxazepino[6,7-e]indole;
8-(biphenyl-3-ylsulfonyl)-1,3,4,8-tetrahydro-2H-[1,4]oxazepino[6,7-e]indole;
8-{[2-(trifluoromethyl)phenyl]sulfonyl}-1,3,4,8-tetrahydro-2H-[1,4]oxazepino[6,7-e]indole;
8-(1-benzothien-2-ylsulfonyl)-1,3,4,8-tetrahydro-2H-[1,4]oxazepino[6,7-e]indole;
8-(1-naphthylsulfonyl)-1,3,4,8-tetrahydro-2H-[1,4]oxazepino[6,7-e]indole;
8-[(5-fluoro-2-methylphenyl)sulfonyl]-1,3,4,8-tetrahydro-2H-[1,4]oxazepino[6,7-e]indole;
(3R)-3-methyl-8-(phenylsulfonyl)-1,3,4,8-tetrahydro-2H-[1,4]oxazepino[6,7-e]indole;
(3R)-2,3-dimethyl-8-(phenylsulfonyl)-1,3,4,8-tetrahydro-2H-[1,4]oxazepino[6,7-e]indole;
6-methoxy-8-(phenylsulfonyl)-1,3,4,8-tetrahydro-2H-[1,4]oxazepino[6,7-e]indole;
9-methyl-8-(phenylsulfonyl)-1,3,4,8-tetrahydro-2H-[1,4]oxazepino[6,7-e]indole;
10-chloro-8-(phenylsulfonyl)-1,3,4,8-tetrahydro-2H-[1,4]oxazepino[6,7-e]indole;
10-chloro-8-[(4-fluorophenyl)sulfonyl]-1,3,4,8-tetrahydro-2H-[1,4]oxazepino[6,7-e]indole;
3-[(10-chloro-1,2,3,4-tetrahydro-8H-[1,4]oxazepino[6,7-e]indol-8-yl)sulfonyl]benzonitrile;
10-chloro-8-(pyridin-3-ylsulfonyl)-1,3,4,8-tetrahydro-2H-[1,4]oxazepino[6,7-e]indole;
8-[(2-chlorophenyl)sulfonyl]-1,3,4,8-tetrahydro-2H-[1,4]oxazepino[6,7-e]indole;
1-methyl-8-(phenylsulfonyl)-1,3,4,8-tetrahydro-2H-[1,4]oxazepino[6,7-e]indole;
(1S)-1-methyl-8-(phenylsulfonyl)-1,3,4,8-tetrahydro-2H-[1,4]oxazepino[6,7-e]indole;
(1R)-1-methyl-8-(phenylsulfonyl)-1,3,4,8-tetrahydro-2H-[1,4]oxazepino[6,7-e]indole;
1-methyl-8-(phenylsulfonyl)-3,8-dihydro-4H-[1,4]oxazepino[6,7-e]indole;
6-fluoro-1-methyl-8-(phenylsulfonyl)-1,3,4,8-tetrahydro-2H-[1,4]oxazepino[6,7-e]indole;
6-methoxy-1-methyl-8-(phenylsulfonyl)-1,3,4,8-tetrahydro-2H-[1,4]oxazepino[6,7-e]indole;
8-[(2-chlorophenyl)sulfonyl]-6-methoxy-1-methyl-1,3,4,8-tetrahydro-2H-[1,4]oxazepino[6,7-e]indole;
6-methoxy-1-methyl-8-[(2-methylphenyl)sulfonyl]-1,3,4,8-tetrahydro-2H-[1,4]oxazepino[6,7-e]indole;
8-[(2,6-difluorophenyl)sulfonyl]-6-methoxy-1-methyl-1,3,4,8-tetrahydro-2H-[1,4]oxazepino[6,7-e]indole;
6-methoxy-8-[(2-methoxy-5-methylphenyhsulfonyl]-1-methyl-1,3,4,8-tetrahydro-2H-[1,4]oxazepino[6,7-e]indole;
8-[(2,4-dichlorophenyl)sulfonyl]-6-methoxy-1-methyl-1,3,4,8-tetrahydro-2H-[1,4]oxazepino[6,7-e]indole;
1-isopropyl-8-(phenylsulfonyl)-1,3,4,8-tetrahydro-2H-[1,4]oxazepino[6,7-e]indole;
1-isopropyl-2-methyl-8-(phenylsulfonyl-1,3,4,8-tetrahydro-2H-[1,4]oxazepino[6,7-e]indole;
1,2-dimethyl-8-(phenylsulfonyl)-1,3,4,8-tetrahydro-2H-[1,4]oxazepino[6,7-e]indole;
10-chloro-1-methyl-8-(phenylsulfonyl)-3,8-dihydro-4H-[1,4]oxazepino[6,7-e]indole;
10-chloro-1-methyl-8-(pyridin-3-ylsulfonyl)-1,3,4,8-tetrahydro-2H[1,4]oxazepino[6,7-e]indole;
10-chloro-1-methyl-8-(phenylsulfonyl-1,3,4,8-tetrahydro-2H-[1,4]oxazepino[6,7-e]indole;
10-chloro-1,2-dimethyl-8-(phenylsulfonyl)-1,3,4,8-tetrahydro-2H-[1,4]oxazepino[6,7-e]indole;
10-chloro-8-[(2-methoxy-5-methylphenyhsulfonyl]-1-methyl-1,3,4,8-tetrahydro-2H-[1,4]oxazepino[6,7-e]indole;
10-chloro-8-[(2-methoxy-5-methylphenyhsulfonyl]-1,2-dimethyl-1,3,4,8-tetrahydro-2H-[1,4]oxazepino[6,7-e]indole;
10-chloro-8-[(2-fluorophenyhsulfonyl]-1-methyl-1,3,4,8-tetrahydro-2H-[1,4]oxazepino[6,7-e]indole;
10-chloro-8-[(2-fluorophenyhsulfonyl]-1,2-dimethyl-1,3,4,8-tetrahydro-2H-[1,4]oxazepino[6,7-e]indole;
10-chloro-8-[(3-fluorophenyl)sulfonyl]-1-methyl-1,3,4,8-tetrahydro-2H-[1,4]oxazepino[6,7-e]indole;
10-chloro-8-[(3-fluorophenyl)sulfonyl]-1,2-dimethyl-1,3,4,8-tetrahydro-2H-[1,4]oxazepino[6,7-e]indole;
1-methyl-8-(pyridin-3-ylsulfonyl)-1,3,4,8-tetrahydro-2H-[1,4]oxazepino[6,7-e]indole;
8-[(2-chlorophenyl)sulfonyl]-1-methyl-1,3,4,8-tetrahydro-2H-[1,4]oxazepino[6,7-e]indole;
1-methyl-8[(2-methylphenyl)sulfonyl]-1,3,4,8-tetrahydro-2H-[1,4]oxazepino[6,7-e]indole;
8[(2,6-difluorophenyl)sulfonyl]-1-methyl-1,3,4,8-tetrahydro-2H-[1,4]oxazepino[6,7-e]indole;
8[(2,4-dichlorophenyl)sulfonyl]-1-methyl-1,3,4,8-tetrahydro-2H-[1,4]oxazepino[6,7-e]indole;

8[(2-methoxy-5-methylphenyl)sulfonyl]-1-methyl-1,3,4,
8-tetrahydro-2H-[1,4]oxazepino[6,7-e]indole;
8[(2-methoxy-4-methylphenyl)sulfonyl]-1-methyl-1,3,4,
8-tetrahydro-2H-[1,4]oxazepino[6,7-e]indole;
8[(2,5-dimethyl-3-thienyl)sulfonyl]-1-methyl-1,3,4,8-tetrahydro-2H-[1,4]oxazepino[6,7-e]indole;
8[(2,5-dimethyl-3-furyl)sulfonyl]-1-methyl-1,3,4,8-tetrahydro-2H-[1,4]oxazepino[6,7-e]indole;
1-methyl-8-(2-thienylsulfonyl)-1,3,4,8-tetrahydro-2H-[1,4]oxazepino[6,7-e]indole;
1-methyl-8-[(5-methylisoxazol-4-yl)sulfonyl]-1,3,4,8-tetrahydro-2H-[1,4]oxazepino[6,7-e]indole; or
8[(1,2-dimethyl-1H-imidazol-4-yl)sulfonyl]-1-methyl-1,3,4,8-tetrahydro-2H-[1,4]oxazepino[6,7-e]indole.

7. A method for amelioration of a disorder in a subject comprising administration to the subject of a composition comprising a compound according to claim 1, wherein the disorder is obesity.

8. A method for making a composition comprising combining a compound according to claim 1 with a pharmaceutically acceptable diluent or carrier.

9. A method for the amelioration of a 5-$HT_6$ receptor-related disorder, comprising administering to a mammal in need of such treatment an effective amount of a compound according to claim 1, wherein the disorder is obesity.

10. A pharmaceutical formulation containing a compound according to claim 1 as active ingredient in combination with a pharmaceutically acceptable diluent or carrier.

11. The pharmaceutical formulation according to claim 10 further comprising an additional therapeutic agent.

12. The pharmaceutical formulation according to claim 10 wherein the compound according to claim 1 is useful in the reduction of body weight or reduction of body weight gain.

13. A cosmetic composition comprising a compound according to claim 1 as active ingredient, in combination with a diluent, excipient or carrier adapted for oral administration.

14. The cosmetic composition according to claim 13, further comprising an additional active ingredient.

* * * * *